US010259858B2

(12) United States Patent
Landgraf et al.

(10) Patent No.: US 10,259,858 B2
(45) Date of Patent: Apr. 16, 2019

(54) INSERTABLE VARIABLE FRAGMENTS OF ANTIBODIES AND MODIFIED α1-α2 DOMAINS OF NKG2D LIGANDS, AND NON-NATURAL NKG2D LIGANDS THAT BIND NON-NATURAL NKG2D RECEPTORS

(71) Applicant: AvidBiotics Corp., South San Francisco, CA (US)

(72) Inventors: Kyle Landgraf, Alameda, CA (US); Daniel P. Steiger, San Francisco, CA (US); Tarah Baron, Daly City, CA (US); Dana Gebhart, San Francisco, CA (US)

(73) Assignee: XYPHOS BIOSCIENCES INC., Lewes, DE (US)

( * ) Notice: Subject to any disclaimer, the term of this patent is extended or adjusted under 35 U.S.C. 154(b) by 108 days.

(21) Appl. No.: 15/228,718

(22) Filed: Aug. 4, 2016

(65) Prior Publication Data
US 2018/0134765 A1 May 17, 2018

Related U.S. Application Data

(60) Provisional application No. 62/200,949, filed on Aug. 4, 2015.

(51) Int. Cl.
*C07K 14/705* (2006.01)
*C07K 16/28* (2006.01)
*C07K 16/30* (2006.01)

(52) U.S. Cl.
CPC .......... *C07K 14/7056* (2013.01); *C07K 16/28* (2013.01); *C07K 16/2863* (2013.01); *C07K 16/30* (2013.01); *C07K 2317/622* (2013.01); *C07K 2317/94* (2013.01); *C07K 2319/00* (2013.01); *C07K 2319/03* (2013.01); *C07K 2319/21* (2013.01); *C07K 2319/33* (2013.01); *C07K 2319/74* (2013.01)

(58) Field of Classification Search
CPC .................. C07K 14/705–14/70596
See application file for complete search history.

(56) References Cited

U.S. PATENT DOCUMENTS

2015/0165065 A1  6/2015  Landgraf et al.

FOREIGN PATENT DOCUMENTS

WO    WO 2016090278    6/2016

OTHER PUBLICATIONS

Wittenbrink et al., Eur J Immunol 39:1642-51 (Year: 2009).*
International Search Report (with Written Opinion) for PCT/US2015/045550 dated Oct. 27, 2016.

Culpepper et al., "Systematic mutation and thermodynamic analysis of central tyrosine pairs in polyspecific NKG2D receptor interactions", Molecular Immunology, 48:516-523 (2011).
VanSeggelen et al., "T Cells Engineered With Chimeric Antigen Receptors Targeting NKG2D Ligands Display Lethal Toxicity in Mice", The American Society of Gene and Cell Therapy, 23(10):1600-1610 (2015).
Sentman et al., "NKG2D CARs as cell therapy for cancer", Cancer J., 20(2):156-159 (2014).
Gill et al., "Going viral: chimeric antigen receptor T-cell therapy for hematological malignancies", Immunological Reviews, 263:68-89 (2015).
Amorette Barber et al. "Chimeric NKG2D T cells require both T cell- and host-derived cytokine secretion and perforin expression to increase tumor antigen presentation and systemic immunity" Journal of Immunology vol. 183, No. 4, 2009 (pp. 2365-2372).
Adelheid Cerwenka et al. "Ectopic expression of retinoic acid early inducible-1 gene (RAE-1) permits natural killer cell-mediated rejection of a MHC class I-bearing tumor in vivo" Proceedings of the National Academy of Sciences of the United States of America vol. 98 No. 20; Sep. 25, 2001 (pp. 11521-11526).
Yu-Hsiang Chang et al. "A chimeric receptor with NKG2D specificity enhances natural killer cell activation and killing of tumor cells" Cancer Research vol. 73, No. 6, Mar. 15, 2013 (pp. 1777-1786).
Min Cheng et al. "NK cell-based immunotherapy for malignant diseases" Cellular & Molecular Immunology vol. 10, 2013 (pp. 230-252).
Hyun-Mi Cho et al. "Delivery of NKG2D ligand using an anti-HER2 antibody-NKG2D ligand fusion protein results in an enhanced innate and adaptive antitumor response" Cancer Research vol. 70, No. 24, Dec. 15, 2010 (pp. 10121-10130).
Andreas Diefenbach et al. "Rae1 and H60 ligands of the NKG2D receptor stimulate tumor immunity" Nature; vol. 413, No. 6852, 2001 (pp. 165-171).
Dr. Alfred L. Garfall et al. "Chimeric Antigen Receptor T Cells against CD19 for Multiple Myeloma" The New England Journal of Medicine vol. 373, No. 11, Sep. 10, 2015 (pp. 1040-1047).
Wolfgang Glienke et al. "Advantages and applications of CAR-expressing natural killer cells" Frontiers in Pharmacology, vol. 6, Article 21; Feb. 12, 2015 (7 pages total).
Samuel Henager et al. "Combining different design strategies for rational affinity maturation of the MICA-NKG2D interface" Protein Science vol. 21, 2012 (pp. 1396-1402).
Christian Kellner et al. "Enhancing natural killer cell-mediated lysis of lymphoma cells by combining therapeutic antibodies with CD20-specific immunoligands engaging NKG2D or NKp30" OncoImmunology vol. 5, No. 1, Jan. 2016 (12 pages total).
C. Kellner et al. "Fusion proteins between ligands for NKG2D and CD20-directed single-chain variable fragments sensitize lymphoma cells for natural killer cell-mediated lysis and enhance antibody-dependent cellular cytotoxicity" Leukemia, vol. 26, 2012 (pp. 830-834).

(Continued)

*Primary Examiner* — Jessica H Roark
(74) *Attorney, Agent, or Firm* — Sughrue Mion, PLLC

(57) ABSTRACT

This application relates generally to the production of polypeptides having specific antigen-binding properties of Fv domains, for example, insertable variable fragments of antibodies, and modified α1-α2 domains of NKG2D ligands.

23 Claims, 26 Drawing Sheets
(26 of 26 Drawing Sheet(s) Filed in Color)

Specification includes a Sequence Listing.

(56) References Cited

OTHER PUBLICATIONS

Candace S.E. Lengyel et al. "Mutations designed to destabilize the receptor-bound conformation increase MICA-NKG2D association rate and affinity" The Journal of Biological Chemistry vol. 282 No. 42, Oct. 19, 2007 (pp. 30658-30666).
Benjamin J. McFarland et al. "Symmetry recognizing asymmetry: analysis of the interactions between the C-type lectin-like immunoreceptor NKG2D and MHC class I-like ligands" Structure vol. 11, Apr. 2003 (pp. 411-422).
Benjamin J. McFarland et al. "Thermodynamic analysis of degenerate recognition by the NKG2D immunoreceptor: not induced fit but rigid adaptation" Immunity, vol. 19, Dec. 2003 (pp. 803-812).
Matthias Peipp et al. "HER2-specific immunoligands engaging NKp30 or NKp80 trigger NK-cell-mediated lysis of tumor cells and enhance antibody-dependent cell-mediated cytotoxicity" Oncotarget vol. 6 No. 31, Sep. 15, 2015 (pp. 32075-32088).
Kamalakannan Rajasekaran et al. "Functional dichotomy between NKG2D and CD28-mediated co-stimulation in human CD8$^+$ T cells" PLoS One, vol. 5, Issue. 9, Sep. 2010 (10 pages total).
Aaron P. Rapoport et al. "NY-ESO-1-specific TCR-engineered T-cells mediate sustained antigen-specific antitumor effects in myeloma" Nature Medicine vol. 21, No. 8, Aug. 2015 (pp. 914-921).
David T. Rodgers et al. "Switch-mediated activation and retargeting of CAR-T cells for B-cell malignancies" Proceedings of the National Academy of Sciences of the United States of America vol. 113, Jan. 12, 2016 (pp. E459-E468).
Kole T. Roybal et al. "Precision Tumor Recognition by T Cells With Combinatorial Antigen-Sensing Circuits" Cell vol. 164, No. 4, Feb. 11, 2016 (pp. 770-779).
De-Gang Song et al. "Chimeric NKG2D CAR-expressing T cell-mediated attack of human ovarian cancer is enhanced by histone deacetylase inhibition" Human Gene Therapy vol. 24, Mar. 2013 (pp. 295-305).
Paul Spear et al. "NKG2D CAR Tcell therapy inhibits the growth of NKG2D ligand heterogeneous tumors" Immunology Cell Biology vol. 91, No. 6, Jul. 2013 (pp. 435-440).
Paul Spear et al. "NKG2D ligands as therapeutic targets" Cancer Immunity vol. 13, May 1, 2013 (14 pages total).
Elke Pogge von Strandmann et al. "A novel bispecific protein (ULBP2-BB4) targeting the NKG2D receptor on natural killer (NK) cells and CD138 activates NK cells and has potent antitumor activity against human multiple myeloma in vitro and in vivo" Blood vol. 107 No. 5, Mar. 1, 2006 (pp. 1955-1962).
Chia-Yung Wu et al. "Remote control of therapeutic T cells through a small molecule-gated chimeric receptor" Science vol. 350, No. 6258, Oct. 16, 2015 (21 pages total).
Wei Xie et al. "VEGFR2 targeted antibody fused with MICA stimulates NKG2D mediated immunosurveillance and exhibits potent anti-tumor activity against breast cancer" Oncotarget vol. 7 No. 13, Feb. 19, 2016 (pp. 16455-16471).
Tong Zhang et al. "Cancer immunotherapy using a bi-specific NK receptor-fusion protein that engages both T cells and tumor cells" Cancer Research vol. 71, No. 6, Mar. 15 2011 (pp. 2066-2076).
Pingwei Li et al. "Complex structure of the activating immunoreceptor NKG2D and its MHC class I-like ligand MICA" Nature immunology vol. 2, No. 5, May 2001 (pp. 443-451).
Klebanoff et al. "Prospects for gene-engineered T cell immunotherapy for solid cancers" Nat. Med., vol. 22, No. 1, Jan. 2016, pp. 26-36.
Wang, et al., "A bispecific protein rG7S-MICA recruits natural killer cells and enhances NKG2D-mediated immunosurveillance against hepatocellular carcinoma", Cancer Letters 372, pp. 166-178, 2016.

* cited by examiner

FIGURE 4
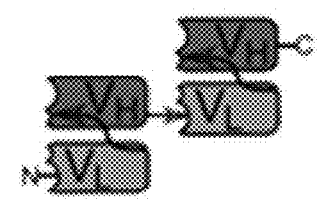
tandem di-scFv
diabody
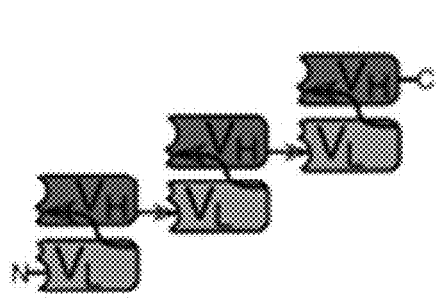
tandem tri-scFv
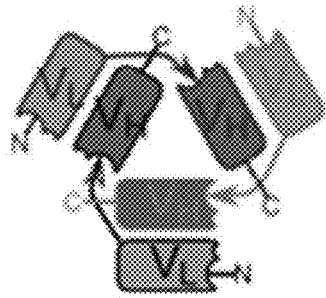
tri(a)body

FIGURE 10

FIGURE 19
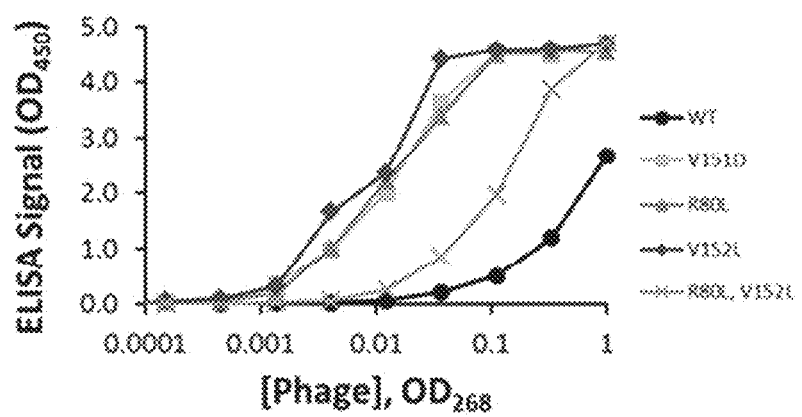
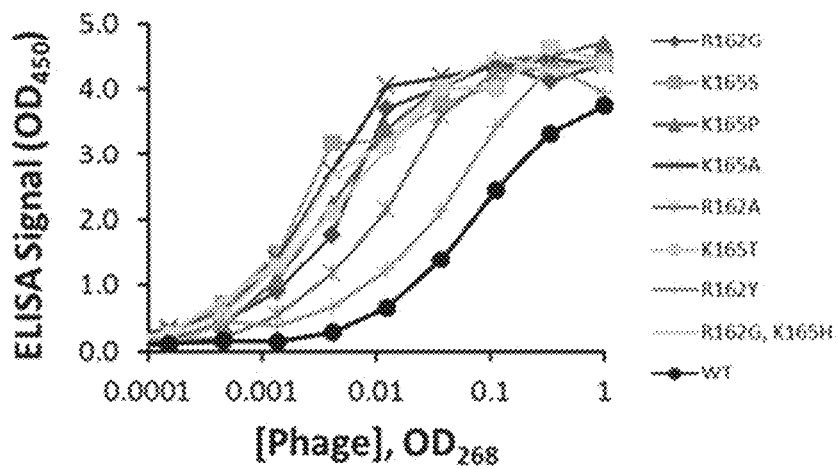

FIGURE 20

```
MICA  HSLRYNLTVLSGDGSVQSGFLAEVHLDGQPFLRCDRQKCRAKPQGQWAEDVLGNKTWDRE
ULBP4 HSLCFNFTIKSLSRPGQPWCEAQVFLNKNLFLQYNSDNNMVKPLGLLGKKVYATSTWGEL
ULBP3 HSLWYNFTIIHLPRHGQQWCEVQSQVDQKNFLSYDCGSDKVLSMGHLEEQLYATDAWGKQ
ULBP1 HCLCYDFIITPKSRPEPQWCEVQGLVDERPFLHYDCVNHKAKAFASLGKKVNVTKTWEEQ
ULBP5 HSLCYDITVIPKFRPGPRWCAVQGQVDEKTFLHYDCGSKTVTPVSPLGKKLNVTTAWKAQ
ULBP2 HSLCYDITVI........CAVQGQVDEKTFLHYDCGNKTVTPVSPLGKKLNVTTAWKAQ
ULBP6 HSLCYDITVIPKFRPGPRWCAVQGQVDEKTFLHYDCGNKTVTPVSPLGKKLNVTTAWKAQ
       * *                     **                 *

MICA  TRDLTGNGKDLRMTLAHIKDQ---KEGLHSLQEIRVCEIHEDNSTRSSQHFYYDGELFLS
ULBP4 TQTLGEVGRDLRMLLCDIKP-QIKTSDPSTLQVEMFCQREAERCTGASWQFATNGEKSLL
ULBP3 L............A.TELEDFTPSGPLTLQVRMSCECEADGYIRGSWQFSFDGRKF.L
ULBP1 TETLRDVVDFLKGQLLDIQVENLIPIEPLTLQARMSCEHEAHGHGRGSWQFLFNGQKFLL
ULBP5 NPVLREVVDILTEQLLDIQLENYIPKEPLTLQARMSCEQKAEGHSGSWQLSFDGQIFLL
ULBP2 N..............QLENYTPKEPLTLQARMSCEQKAEGHSSGSWQFSFDGQIF..
ULBP6 NPVLREVVDILTEQLLDIQLENYTPKEPLTLQARMSCEQKAEGHSSGSWQFSIDGQTFLL
           *       *            **   *         *      *   *

MICA  QNLETEEWTMPQSSRAQTLAMNVRNFLKEDAMKTKTHYHAMHADCLQELRRYLK
ULBP4 FDAMNMTWTVINHEASKIKE----TWKKDRGLE-KYFRKLSKGDCDHWLREFLG
ULBP3 ........T.VHAGARRMKE----KWEK............C..WLRDFLM
ULBP1 FDSNNRKWTALHPGAKKMTE----KWEKNRDVT-MFFQKISLGDCKMWLEEFLM
ULBP5 FDSENRMWTTVHPGARKMKE----KWENDKDMT-MSFHYISMGDCTGWLEDFLM
ULBP2 ............VHPGARKMKE----........MSFHYISMGDC..WLEDFLM
ULBP6 FDSEKRMWTTVHPGARKMKE----KWENDKDVA-MSFHYISMGDCIGWLEDFLM
               **                             **   *   *
```

SEQUENCE LISTING

```
<160> NUMBER OF SEQ ID NOS: 105

<210> SEQ ID NO 1
<211> LENGTH: 1126
<212> TYPE: DNA
<213> ORGANISM: Artificial Sequence
<220> FEATURE:
<223> OTHER INFORMATION: Synthetic polynucleotide, encoding alpha3-iFv.1

<400> SEQUENCE: 1 cccccatgg tgcaagttac ccgcagcgag gcctcaggag atcgcgtaac tatcacttgc      60
agagcttctc aggacgtgtc caccgcggtt gcttggtacc agcaaaagcc tggaaaggcg    120
```

```
ccgaagctgc tgatctactc cgcctcattc ttgtactcag gagtgcccag tcgatttagt    180
ggtagcggtt ctggtactga tttcacccct taccatcagca gtctccagcc cgaggatttc    240
gctacttatt actgccagca gtcatacacc actcctccca ctttcggcca aggtaccaag    300
gtcgagatta aggcggaag ctctaggtcc tctagctccg gaggaggtgg ctctggcggc    360
ggcggagaag tccaactggt ggagagcgga ggcggactgg tgcagccagg cggatccttg    420
agacttagct gtgcggcttc gggttttacc tttacttcta ctggcatcag ttgggtcaga    480
caagcgcctg gcaagggact ggaatgggtt ggacgtatct accccactaa tggttcgacg    540
aactatgcgg atagtgtgaa aggtagattc acgatatctg ctgacacctc gaagaatacc    600
gcttaccttc aaatgaatag tttgcgtgcc gaagatactg ctgtctacta ttgcgccaga    660
acctatggaa tatacgacct ttatgtggac tacaccgagt acgtcatgga ttattggggc    720
cagggtacgt tggtgacagt gtcgagtggc ggaagctcta ggtcctctag ctccggagga    780
ggtggctctg gcggcggcgg agacattcag atgactcagt ctcccagttc tcttagtgcc    840
tctggccaaa ttaccgtcac gtgtcgtgct agcggcttct acccgtggaa tatcaccctg    900
agctggcgcc aagacggtgt tagcctgagc cacgacaccc aacaatgggg cgacgtgttg    960
ccagatggca aggtaccta ccagacgtgg gttgccaccc gtatttccca gggtgaagag   1020
cagcgtttta cctgctatat ggaacacagc ggccaacata gcacgcatcc ggtgccgagc   1080
ggtaaaggta gccaccatca tcaccaccat tagtaggaat tccgga               1126

<210> SEQ ID NO 2
<211> LENGTH: 1144
<212> TYPE: DNA
<213> ORGANISM: Artificial Sequence
<220> FEATURE:
<223> OTHER INFORMATION: Synthetic polynucleotide, encoding alpha3-iFv.2

<400> SEQUENCE: 2 cccccccatgg tgcaagttac ccgcagcgag gcctcaggcg gaagcggaga tcgcgtaact    60
atcacttgca gagcttctca ggacgtgtcc accgcggttg cttggtacca gcaaaagcct    120
ggaaaggcgc cgaagctgct gatctactcc gcctcattct tgtactcagg agtgcccagt    180
cgatttagtg gtagcggttc tggtactgat ttcacccctta ccatcagcag tctccagccc    240
gaggatttcg ctacttatta ctgccagcag tcatacacca ctcctcccac tttcggccaa    300
ggtaccaagg tcgagattaa aggcggaagc tctaggtcct ctagctccgg aggaggtggc    360
tctggcggcg gcggagaagt ccaactggtg gagagcggag gcggactggt gcagccaggc    420
ggatccttga gacttagctg tgcggcttcg ggttttacct ttacttctac tggcatcagt    480
tgggtcagac aagcgcctgg caagggactg gaatgggttg gacgtatcta ccccactaat    540
ggttcgacga actatgcgga tagtgtgaaa ggtagattca cgatatctgc tgacacctcg    600
aagaataccg cttaccttca aatgaatagt ttgcgtgccg aagatactgc tgtctactat    660
tgcgccagaa cctatggaat atacgacctt tatgtggact acaccgagta cgtcatggat    720
tattggggcc agggtacgtt ggtgacagtg tcgagtggcg gaagctctag gtcctctagc    780
tccggaggag gtggctctgg cggcggcgga gacattcaga tgactcagtc tcccagttct    840
cttagtgcct ctggcggaag cggccaaatt accgtcacgt gtcgtgctag cggcttctac    900
ccgtggaata tcaccctgag ctggcgccaa gacggtgtta gcctgagcca cgacacccaa    960
caatggggca cgtgttgcc agatggccaa ggtacctacc agacgtgggt tgccacccgt   1020
atttcccagg gtgaagagca gcgttttacc tgctatatgg aacacagcgg ccaacatagc   1080
```

```
acgcatccgg tgccgagcgg taaaggtagc caccatcatc accaccatta gtaggaattc    1140
cgga                                                                 1144
```

<210> SEQ ID NO 3
<211> LENGTH: 269
<212> TYPE: PRT
<213> ORGANISM: Artificial Sequence
<220> FEATURE:
<223> OTHER INFORMATION: Synthetic peptide iFv (fgfr3)

<400> SEQUENCE: 3

```
Gly Asp Arg Val Thr Ile Thr Cys Arg Ala Ser Gln Asp Val Ser Thr
1               5                   10                  15

Ala Val Ala Trp Tyr Gln Gln Lys Pro Gly Lys Ala Pro Lys Leu Leu
            20                  25                  30

Ile Tyr Ser Ala Ser Phe Leu Tyr Ser Gly Val Pro Ser Arg Phe Ser
        35                  40                  45

Gly Ser Gly Ser Gly Thr Asp Phe Thr Leu Thr Ile Ser Ser Leu Gln
    50                  55                  60

Pro Glu Asp Phe Ala Thr Tyr Tyr Cys Gln Gln Ser Tyr Thr Thr Pro
65                  70                  75                  80

Pro Thr Phe Gly Gln Gly Thr Lys Val Glu Ile Lys Gly Gly Ser Ser
                85                  90                  95

Arg Ser Ser Ser Gly Gly Gly Ser Gly Gly Gly Glu Val
            100                 105                 110

Gln Leu Val Glu Ser Gly Gly Leu Val Gln Pro Gly Gly Ser Leu
            115                 120                 125

Arg Leu Ser Cys Ala Ala Ser Gly Phe Thr Phe Thr Ser Thr Gly Ile
    130                 135                 140

Ser Trp Val Arg Gln Ala Pro Gly Lys Gly Leu Glu Trp Val Gly Arg
145                 150                 155                 160

Ile Tyr Pro Thr Asn Gly Ser Thr Asn Tyr Ala Asp Ser Val Lys Gly
                165                 170                 175

Arg Phe Thr Ile Ser Ala Asp Thr Ser Lys Asn Thr Ala Tyr Leu Gln
            180                 185                 190

Met Asn Ser Leu Arg Ala Glu Asp Thr Ala Val Tyr Tyr Cys Ala Arg
        195                 200                 205

Thr Tyr Gly Ile Tyr Asp Leu Tyr Val Asp Tyr Thr Glu Tyr Val Met
    210                 215                 220

Asp Tyr Trp Gly Gln Gly Thr Leu Val Thr Val Ser Ser Gly Gly Ser
225                 230                 235                 240

Ser Arg Ser Ser Ser Gly Gly Gly Gly Ser Gly Gly Gly Gly Asp
                245                 250                 255

Ile Gln Met Thr Gln Ser Pro Ser Ser Leu Ser Ala Ser
            260                 265
```

<210> SEQ ID NO 4
<211> LENGTH: 807
<212> TYPE: DNA
<213> ORGANISM: Artificial Sequence
<220> FEATURE:
<223> OTHER INFORMATION: Synthetic polynucleotide, encoding iFv (fgfr3)

<400> SEQUENCE: 4

```
ggagatcgcg taactatcac ttgcagagct tctcaggacg tgtccaccgc ggttgcttgg    60
taccagcaaa agcctggaaa ggcgccgaag ctgctgatct actccgcctc attcttgtac    120
```

```
tcaggagtgc ccagtcgatt tagtggtagc ggttctggta ctgatttcac ccttaccatc    180
agcagtctcc agcccgagga tttcgctact tattactgcc agcagtcata ccactcct     240 cccactttcg gccaaggtac caaggtcgag attaaaggcg aagctctag gtcctctagc    300 tccgaggag gtggctctgg cggcggcgga gaagtccaac tggtggagag cggaggcgga    360
ctggtgcagc caggcggatc cttgagactt agctgtgcgg cttcgggttt tacctttact   420
tctactggca tcagttgggt cagacaagcg cctggcaagg actggaatg ggttggacgt    480 atctacccca ctaatggttc gacgaactat gcggatagtg tgaaaggtag attcacgata   540
tctgctgaca cctcgaagaa taccgcttac cttcaaatga atagtttgcg tgccgaagat   600
actgctgtct actattgcgc cagaacctat ggaatatacg acctttatgt ggactacacc   660
gagtacgtca tggattattg gggccagggt acgttggtga cagtgtcgag tggcggaagc   720
tctaggtcct ctagctccgg aggaggtggc tctggcggcg gcggagacat tcagatgact   780
cagtctccca gttctcttag tgcctct                                       807
```

```
<210> SEQ ID NO 5
<211> LENGTH: 18
<212> TYPE: PRT
<213> ORGANISM: Artificial Sequence
<220> FEATURE:
<223> OTHER INFORMATION: Synthetic peptide linker region

<400> SEQUENCE: 5

Gly Gly Ser Ser Arg Ser Ser Ser Gly Gly Gly Gly Ser Gly Gly
1               5                   10                  15

Gly Gly

<210> SEQ ID NO 6
<211> LENGTH: 370
<212> TYPE: PRT
<213> ORGANISM: Artificial Sequence
<220> FEATURE:
<223> OTHER INFORMATION: Synthetic peptide alpha3-iFv.1

<400> SEQUENCE: 6

Pro Pro Met Val Gln Val Thr Arg Ser Glu Ala Ser Gly Asp Arg Val
1               5                   10                  15

Thr Ile Thr Cys Arg Ala Ser Gln Asp Val Ser Thr Ala Val Ala Trp
            20                  25                  30

Tyr Gln Gln Lys Pro Gly Lys Ala Pro Lys Leu Leu Ile Tyr Ser Ala
        35                  40                  45

Ser Phe Leu Tyr Ser Gly Val Pro Ser Arg Phe Ser Gly Ser Gly Ser
    50                  55                  60

Gly Thr Asp Phe Thr Leu Thr Ile Ser Ser Leu Gln Pro Glu Asp Phe
65                  70                  75                  80

Ala Thr Tyr Tyr Cys Gln Gln Ser Tyr Thr Thr Pro Pro Thr Phe Gly
                85                  90                  95

Gln Gly Thr Lys Val Glu Ile Lys Gly Gly Ser Ser Arg Ser Ser Ser
            100                 105                 110

Ser Gly Gly Gly Gly Ser Gly Gly Gly Gly Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Thr Phe Thr Ser Thr Gly Ile Ser Trp Val Arg
145                 150                 155                 160
```

```
Gln Ala Pro Gly Lys Gly Leu Glu Trp Val Gly Arg Ile Tyr Pro Thr
                165                 170                 175

Asn Gly Ser Thr Asn Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ala Arg Thr Tyr Gly Ile
    210                 215                 220

Tyr Asp Leu Tyr Val Asp Tyr Thr Glu Tyr Val Met Asp Tyr Trp Gly
225                 230                 235                 240

Gln Gly Thr Leu Val Thr Val Ser Ser Gly Gly Ser Ser Arg Ser Ser
                245                 250                 255

Ser Ser Gly Gly Gly Gly Ser Gly Gly Gly Asp Ile Gln Met Thr
            260                 265                 270

Gln Ser Pro Ser Ser Leu Ser Ala Ser Gly Gln Ile Thr Val Thr Cys
        275                 280                 285

Arg Ala Ser Gly Phe Tyr Pro Trp Asn Ile Thr Leu Ser Trp Arg Gln
    290                 295                 300

Asp Gly Val Ser Leu Ser His Asp Thr Gln Gln Trp Gly Asp Val Leu
305                 310                 315                 320

Pro Asp Gly Gln Gly Thr Tyr Gln Thr Trp Val Ala Thr Arg Ile Ser
                325                 330                 335

Gln Gly Glu Glu Gln Arg Phe Thr Cys Tyr Met Glu His Ser Gly Gln
        340                 345                 350

His Ser Thr His Pro Val Pro Ser Gly Lys Ser His His His
    355                 360                 365

His His
   370

<210> SEQ ID NO 7
<211> LENGTH: 376
<212> TYPE: PRT
<213> ORGANISM: Artificial Sequence
<220> FEATURE:
<223> OTHER INFORMATION: Synthetic peptide alpha3-iFv.2

<400> SEQUENCE: 7

Pro Pro Met Val Gln Val Thr Arg Ser Glu Ala Ser Gly Gly Ser Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Gly Ser Ser Arg
            100                 105                 110

Ser Ser Ser Ser Gly Gly Gly Ser Gly Gly Gly Glu Val Gln
        115                 120                 125

Leu Val Glu Ser Gly Gly Gly Leu Val Gln Pro Gly Gly Ser Leu Arg
    130                 135                 140
```

-continued

```
Leu Ser Cys Ala Ala Ser Gly Phe Thr Phe Thr Ser Thr Gly Ile Ser
145                 150                 155                 160

Trp Val Arg Gln Ala Pro Gly Lys Gly Leu Glu Trp Val Gly Arg Ile
                165                 170                 175

Tyr Pro Thr Asn Gly Ser Thr Asn Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ala Arg Thr
    210                 215                 220

Tyr Gly Ile Tyr Asp Leu Tyr Val Asp Tyr Thr Glu Tyr Val Met Asp
225                 230                 235                 240

Tyr Trp Gly Gln Gly Thr Leu Val Thr Val Ser Ser Gly Gly Ser Ser
                245                 250                 255

Arg Ser Ser Ser Gly Gly Gly Ser Gly Gly Gly Gly Asp Ile
            260                 265                 270

Gln Met Thr Gln Ser Pro Ser Ser Leu Ser Ala Ser Gly Gly Ser Gly
                275                 280                 285

Gln Ile Thr Val Thr Cys Arg Ala Ser Gly Phe Tyr Pro Trp Asn Ile
        290                 295                 300

Thr Leu Ser Trp Arg Gln Asp Gly Val Ser Leu Ser His Asp Thr Gln
305                 310                 315                 320

Gln Trp Gly Asp Val Leu Pro Asp Gly Gln Gly Thr Tyr Gln Thr Trp
                325                 330                 335

Val Ala Thr Arg Ile Ser Gln Gly Glu Glu Gln Arg Phe Thr Cys Tyr
            340                 345                 350

Met Glu His Ser Gly Gln His Ser Thr His Pro Val Pro Ser Gly Lys
        355                 360                 365

Gly Ser His His His His His His
        370                 375

<210> SEQ ID NO 8
<211> LENGTH: 368
<212> TYPE: PRT
<213> ORGANISM: Artificial Sequence
<220> FEATURE:
<223> OTHER INFORMATION: Synthetic peptide alpha3-iFv.3(CD20)

<400> SEQUENCE: 8

Pro Pro Met Val Gln Val Thr Arg Ser Glu Ala Ser Gly Gly Ser Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Gly Gly Ser Ser Arg Ser
            100                 105                 110

Ser Ser Gly Gly Gly Ser Gly Gly Gly Gln Val Gln Leu
        115                 120                 125
```

```
Gln Gln Pro Gly Ala Glu Leu Val Lys Pro Gly Ala Ser Val Lys Met
        130                 135                 140
Ser Cys Lys Ala Ser Gly Tyr Thr Phe Thr Ser Tyr Asn Met His Trp
145                 150                 155                 160
Val Lys Gln Thr Pro Gly Arg Gly Leu Glu Trp Ile Gly Ala Ile Tyr
                165                 170                 175
Pro Gly Asn Gly Asp Thr Ser Tyr Asn Gln Lys Phe Lys Gly Lys Ala
            180                 185                 190
Thr Leu Thr Ala Asp Lys Ser Ser Thr Ala Tyr Met Gln Leu Ser
        195                 200                 205
Ser Leu Thr Ser Glu Asp Ser Ala Val Tyr Tyr Cys Ala Arg Ser Thr
    210                 215                 220
Tyr Tyr Gly Gly Asp Trp Tyr Phe Asn Val Trp Gly Ala Gly Thr Thr
225                 230                 235                 240
Val Thr Val Ser Ala Gly Gly Ser Ser Arg Ser Ser Ser Gly Gly
                245                 250                 255
Gly Gly Ser Gly Gly Gly Gly Gln Ile Val Leu Ser Gln Ser Pro Ala
            260                 265                 270
Ile Leu Ser Ala Ser Gly Gly Ser Gln Ile Thr Val Thr Cys Arg Ala
        275                 280                 285
Ser Gly Phe Tyr Pro Trp Asn Ile Thr Leu Ser Trp Arg Gln Asp Gly
    290                 295                 300
Val Ser Leu Ser His Asp Thr Gln Gln Trp Gly Asp Val Leu Pro Asp
305                 310                 315                 320
Gly Gln Gly Thr Tyr Gln Thr Trp Val Ala Thr Arg Ile Ser Gln Gly
                325                 330                 335
Glu Glu Gln Arg Phe Thr Cys Tyr Met Glu His Ser Gly Gln His Ser
            340                 345                 350
Thr His Pro Val Pro Ser Gly Lys Gly Ser His His His His His
        355                 360                 365

<210> SEQ ID NO 9
<211> LENGTH: 561
<212> TYPE: DNA
<213> ORGANISM: Artificial Sequence
<220> FEATURE:
<223> OTHER INFORMATION: Synthetic polynucleotide, encoding ULBP1
      alpha1-alpha2

<400> SEQUENCE: 9
gctgctgagc cccactgtct ctgctacgac tttattataa ctcctaagtc aagaccagag      60
cctcagtggt gcgaagtaca aggtttggtt gacgaaaggc ctttccttca ctacgattgt     120
gtgaaccata aggcaaaggc tttcgccagc ctgggtaaga aggtaaacgt tactaagacg     180
tgggaggagc agacggaaac cctccgtgat gtggttgact ttcttaaggg tcagctcctc     240
gatatccaag tggagaattt aatccctatc gaaccgctca ctctgcaggc cagaatgtca     300
tgcgaacatg aagcacacgg tcatggaaga ggtagttggc aatttttatt taacggtcaa     360
aaattcctgc tgttcgactc aaacaaccgc aaatggactg cgctgcaccc tggagctaag     420
aagatgactg aaaaatggga gaagaacaga gacgttacca tgttcttcca gaagatttcc     480
ctgggagatt gtaagatgtg gttagaggag ttcttaatgt actgggaaca gatgctggac     540
cccacaaaac cccccatggt g                                                561

<210> SEQ ID NO 10
<211> LENGTH: 567
```

```
<212> TYPE: DNA
<213> ORGANISM: Artificial Sequence
<220> FEATURE:
<223> OTHER INFORMATION: Synthetic polynucleotide, encoding ULBP2
      alpha1-alpha2

<400> SEQUENCE: 10
gctgctgagc cccatagtct gtgttacgac atcacagtta ttcccaagtt caggcccgga      60
ccgcgctggt gtgccgtgca aggacaagtc gacgaaaaaa cctttcttca ttacgattgc     120
ggaaataaga ctgtaacgcc agtctctcct ttaggtaaga agttaaacgt cactacggcg     180
tggaaggcac aaaaccccgt cctgcgcgag gtcgtcgaca tcctgactga acaattgcgc     240
gacatccagc tcgagaatta cactccaaag gagcctctta ccctgcaggc tagaatgtct     300
tgcgagcaaa aggcagaggg ccactcctcc ggcagctggc agttcagttt cgacggacaa     360
atctttctgt tattcgattc agagaagaga atgtggacta cagttcaccc cggtgcccgt     420
aaaatgaagg agaagtggga aaacgacaaa gtggtggcga tgtcattcca ctatttctcg     480
atgggagact gcatcggttg gctggaagat ttcctcatgg gtatggactc cactttggag     540
ccatcggctg gtgcccccccc catggtg                                        567

<210> SEQ ID NO 11
<211> LENGTH: 561
<212> TYPE: DNA
<213> ORGANISM: Artificial Sequence
<220> FEATURE:
<223> OTHER INFORMATION: Synthetic polynucleotide, encoding ULBP3
      alpha1-alpha2

<400> SEQUENCE: 11
gctgctgagc cccacagctt gtggtacaac ttcaccatta tccacttgcc gagacatggc      60
cagcagtggt gcgaagtgca atcgcaagtc gaccaaaaaa acttcttatc atacgactgc     120
ggcagcgata aggtcttatc tatgggtcat ttggaggaac agctctacgc gaccgacgcc     180
tggggtaaac agctcgagat gctccgtgag gttggacaga ggctgagact ggaactggct     240
gacactgagc tggaagattt cacacctagt ggtccactca cattgcaagt acgcatgagc     300
tgcgagtgtg aggccgatgg atacattagg ggcagctggc agtttagctt cgacggaagg     360
aaattcctgc tcttcgacag taacaatagg aagtggactg ttgtgcatgc tggtgcgcgc     420
agaatgaagg aaaagtggga aaagatagc ggcctgacga ccttcttcaa gatggtgtct     480
atgcgtgact gtaagagctg gctcagagat ttcctcatgc atcgcaagaa gaggttagaa     540
cctaccgctc ccccccatgg tg                                              561

<210> SEQ ID NO 12
<211> LENGTH: 561
<212> TYPE: DNA
<213> ORGANISM: Artificial Sequence
<220> FEATURE:
<223> OTHER INFORMATION: Synthetic polynucleotide, encoding ULBP4
      alpha1-alpha2

<400> SEQUENCE: 12
gctgctgagc cccactctct ttgcttcaac ttcaccatta aatccctgag caggcctggt      60
cagccgtggt gtgaggcgca ggtctttctt aacaagaatc tcttcctcca atacaactct     120
gataacaaca tggtaaagcc actgggtctc ctgggtaaaa agtctatgc tacgagcact     180 tggggagaac tcacccagac tcttggcgag gtaggaagag acctgcgcat gctcctctgc     240
gatataaagc cccaaattaa gaccagtgat ccgtccactt tacaagtcga aatgttctgc     300
```

```
caaagggagg ctgaacgctg caccggagcc tcttggcagt tcgcgaccaa tggcgaaaag      360
tccctcttgt tcgatgccat gaatatgacc tggaccgtga tcaatcatga ggcctctaag      420
atcaaggaga cgtggaaaaa ggaccgcggc cttgaaaagt actttaggaa gttgtctaaa      480
ggagactgcg accattggtt acgcgagttc ctcggccatt gggaagcgat gcccgagcca      540
acggttagcc cccccatggt g                                                561

<210> SEQ ID NO 13
<211> LENGTH: 567
<212> TYPE: DNA
<213> ORGANISM: Artificial Sequence
<220> FEATURE:
<223> OTHER INFORMATION: Synthetic polynucleotide, encoding ULBP6
      alpha1-alpha2

<400> SEQUENCE: 13
gctgctgagc cccactcctt atgctatgat atcaccgtga ttccaaagtt ccgaccagga       60
ccccgatggt gcgccgtaca gggacaggtc gacgaaaaga cttttttaca ttacgactgc      120
ggtaacaaga cagtcacacc ggtaagtcct ttgggaaaaa agttaaacgt aaccactgct      180
tggaaggccc agaaccccgt ccttcgagaa gtagtggata ttttgactga acagctgctt      240
gacatccagc tggaaaacta cacacccaaa gagcccctga ctcttcaagc gcgtatgtcg      300
tgtgagcaaa aggccgaagg cacacagctcc ggatcctggc agttcagtat cgacggtcag      360
accttcctcc tcttcgattc agaaaagcgc atgtggacta ctgtgcaccc cggcgctcgt      420
aagatgaagg aaaagtggga gaatgataag gacgttgcca tgagttttca ttacattagt      480
atgggagatt gcatcggttg gctggaagac ttcctgatgg gtatggatag tacccttgaa      540
cctagtgccg gagctccccc catggtg                                          567

<210> SEQ ID NO 14
<211> LENGTH: 483
<212> TYPE: DNA
<213> ORGANISM: Artificial Sequence
<220> FEATURE:
<223> OTHER INFORMATION: Synthetic polynucleotide, encoding OMCP
      alpha1-alpha2

<400> SEQUENCE: 14
gctgctgctg agccccacaa gcttgcgttc aacttcaatc tggaaataaa cggttcagat       60
acccattcaa ccgtggacgt ttatttagac gattcgcaga taatcacctt tgacggcaag      120
gacatccgcc caactatccc gttcatgata ggtgacgaaa tcttccttcc tttttataag      180
aatgtgttct ctgagttctt cagtttgttc cgccgcgtcc ctacctcaac cccctacgaa      240
gacttgactt atttctatga atgcgactac ccgacaacaa atctacattt cgatcaattc      300
tacctgtaca cggtgaagaa gtacaccgtg aagactcaag aggctactaa caagaacatg      360
tggctgacca cttccgagtt cagactgaag aagtggttcg acggcgagga ctgtatcatg      420
caccttagaa gtttagtgag gaaaatggaa gatagcaaga gaagaacagt gccccccatg      480
gtg                                                                    483

<210> SEQ ID NO 15
<211> LENGTH: 187
<212> TYPE: PRT
<213> ORGANISM: Artificial Sequence
<220> FEATURE:
<223> OTHER INFORMATION: Synthetic peptide ULBP1 alpha1-alpha2
```

```
<400> SEQUENCE: 15

Ala Ala Glu Pro His Cys Leu Cys Tyr Asp Phe Ile Ile Thr Pro Lys
1               5                   10                  15

Ser Arg Pro Glu Pro Gln Trp Cys Glu Val Gln Gly Leu Val Asp Glu
            20                  25                  30

Arg Pro Phe Leu His Tyr Asp Cys Val Asn His Lys Ala Lys Ala Phe
        35                  40                  45

Ala Ser Leu Gly Lys Lys Val Asn Val Thr Lys Thr Trp Glu Glu Gln
    50                  55                  60

Thr Glu Thr Leu Arg Asp Val Val Asp Phe Leu Lys Gly Gln Leu Leu
65                  70                  75                  80

Asp Ile Gln Val Glu Asn Leu Ile Pro Ile Glu Pro Leu Thr Leu Gln
                85                  90                  95

Ala Arg Met Ser Cys Glu His Glu Ala His Gly His Gly Arg Gly Ser
            100                 105                 110

Trp Gln Phe Leu Phe Asn Gly Gln Lys Phe Leu Leu Phe Asp Ser Asn
        115                 120                 125

Asn Arg Lys Trp Thr Ala Leu His Pro Gly Ala Lys Lys Met Thr Glu
    130                 135                 140

Lys Trp Glu Lys Asn Arg Asp Val Thr Met Phe Gln Lys Ile Ser
145                 150                 155                 160

Leu Gly Asp Cys Lys Met Trp Leu Glu Glu Phe Leu Met Tyr Trp Glu
                165                 170                 175

Gln Met Leu Asp Pro Thr Lys Pro Pro Met Val
            180                 185

<210> SEQ ID NO 16
<211> LENGTH: 189
<212> TYPE: PRT
<213> ORGANISM: Artificial Sequence
<220> FEATURE:
<223> OTHER INFORMATION: Synthetic peptide ULBP2 alpha1-alpha2

<400> SEQUENCE: 16

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Arg
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
        115                 120                 125

Lys Arg Met Trp Thr Thr Val His Pro Gly Ala Arg Lys Met Lys Glu
    130                 135                 140

Lys Trp Glu Asn Asp Lys Val Val Ala Met Ser Phe His Tyr Phe Ser
145                 150                 155                 160

Met Gly Asp Cys Ile Gly Trp Leu Glu Asp Phe Leu Met Gly Met Asp
```

Ser Thr Leu Glu Pro Ser Ala Gly Ala Pro Pro Met Val
                180                 185

<210> SEQ ID NO 17
<211> LENGTH: 187
<212> TYPE: PRT
<213> ORGANISM: Artificial Sequence
<220> FEATURE:
<223> OTHER INFORMATION: Synthetic peptide ULBP3 alpha1-alpha2

<400> SEQUENCE: 17

Ala Ala Glu Pro His Ser Leu Trp Tyr Asn Phe Thr Ile Ile His Leu
1               5                   10                  15

Pro Arg His Gly Gln Gln Trp Cys Glu Val Gln Ser Gln Val Asp Gln
                20                  25                  30

Lys Asn Phe Leu Ser Tyr Asp Cys Gly Ser Asp Lys Val Leu Ser Met
            35                  40                  45

Gly His Leu Glu Glu Gln Leu Tyr Ala Thr Asp Ala Trp Gly Lys Gln
        50                  55                  60

Leu Glu Met Leu Arg Glu Val Gly Gln Arg Leu Arg Leu Glu Leu Ala
65                  70                  75                  80

Asp Thr Glu Leu Glu Asp Phe Thr Pro Ser Gly Pro Leu Thr Leu Gln
                85                  90                  95

Val Arg Met Ser Cys Glu Ser Glu Ala Asp Gly Tyr Ile Arg Gly Ser
                100                 105                 110

Trp Gln Phe Ser Phe Asp Gly Arg Lys Phe Leu Leu Phe Asp Ser Asn
            115                 120                 125

Asn Arg Lys Trp Thr Val Val His Ala Gly Ala Arg Arg Met Lys Glu
        130                 135                 140

Lys Trp Glu Lys Asp Ser Gly Leu Thr Thr Phe Phe Lys Met Val Ser
145                 150                 155                 160

Met Arg Asp Cys Lys Ser Trp Leu Arg Asp Phe Leu Met His Arg Lys
                165                 170                 175

Lys Arg Leu Glu Pro Thr Ala Pro Pro Met Val
                180                 185

<210> SEQ ID NO 18
<211> LENGTH: 187
<212> TYPE: PRT
<213> ORGANISM: Artificial Sequence
<220> FEATURE:
<223> OTHER INFORMATION: Synthetic peptide ULBP4 alpha1-alpha2

<400> SEQUENCE: 18

Ala Ala Glu Pro His Ser Leu Cys Phe Asn Phe Thr Ile Lys Ser Leu
1               5                   10                  15

Ser Arg Pro Gly Gln Pro Trp Cys Glu Ala Gln Val Phe Leu Asn Lys
                20                  25                  30

Asn Leu Phe Leu Gln Tyr Asn Ser Asp Asn Asn Met Val Lys Pro Leu
            35                  40                  45

Gly Leu Leu Gly Lys Lys Val Tyr Ala Thr Ser Thr Trp Gly Glu Leu
        50                  55                  60

Thr Gln Thr Leu Gly Glu Val Gly Arg Asp Leu Arg Met Leu Leu Cys
65                  70                  75                  80

Asp Ile Lys Pro Gln Ile Lys Thr Ser Asp Pro Ser Thr Leu Gln Val
                85                  90                  95

```
Glu Met Phe Cys Gln Arg Glu Ala Glu Arg Cys Thr Gly Ala Ser Trp
                100                 105                 110

Gln Phe Ala Thr Asn Gly Glu Lys Ser Leu Leu Phe Asp Ala Met Asn
            115                 120                 125

Met Thr Trp Thr Val Ile Asn His Glu Ala Ser Lys Ile Lys Glu Thr
130                 135                 140

Trp Lys Lys Asp Arg Gly Leu Glu Lys Tyr Phe Arg Lys Leu Ser Lys
145                 150                 155                 160

Gly Asp Cys Asp His Trp Leu Arg Glu Phe Leu Gly His Trp Glu Ala
                165                 170                 175

Met Pro Glu Pro Thr Val Ser Pro Pro Met Val
            180                 185

<210> SEQ ID NO 19
<211> LENGTH: 189
<212> TYPE: PRT
<213> ORGANISM: Artificial Sequence
<220> FEATURE:
<223> OTHER INFORMATION: Synthetic peptide ULBP6 alpha1-alpha2

<400> SEQUENCE: 19

Ala Ala Glu Pro His Ser Leu Cys Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45

Ser Pro Leu Gly Lys Lys Leu Asn Val Thr Thr Ala Trp Lys Ala Gln
50                  55                  60

Asn Pro Val Leu Arg Glu Val Val Asp Ile Leu Thr Glu Gln Leu Leu
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
                100                 105                 110

Trp Gln Phe Ser Ile Asp Gly Gln Thr Phe Leu Leu Phe Asp Ser Glu
            115                 120                 125

Lys Arg Met Trp Thr Thr Val His Pro Gly Ala Arg Lys Met Lys Glu
130                 135                 140

Lys Trp Glu Asn Asp Lys Asp Val Ala Met Ser Phe His Tyr Ile Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro Pro Met Val
            180                 185

<210> SEQ ID NO 20
<211> LENGTH: 161
<212> TYPE: PRT
<213> ORGANISM: Artificial Sequence
<220> FEATURE:
<223> OTHER INFORMATION: Synthetic peptide OMCP alpha1-alpha2

<400> SEQUENCE: 20

Ala Ala Ala Glu Pro His Lys Leu Ala Phe Asn Phe Asn Leu Glu Ile
1               5                   10                  15

Asn Gly Ser Asp Thr His Ser Thr Val Asp Val Tyr Leu Asp Asp Ser
            20                  25                  30
```

```
Gln Ile Ile Thr Phe Asp Gly Lys Asp Ile Arg Pro Thr Ile Pro Phe
         35                  40                  45

Met Ile Gly Asp Glu Ile Phe Leu Pro Phe Tyr Lys Asn Val Phe Ser
 50                  55                  60

Glu Phe Phe Ser Leu Phe Arg Arg Val Pro Thr Ser Thr Pro Tyr Glu
 65                  70                  75                  80

Asp Leu Thr Tyr Phe Tyr Glu Cys Asp Tyr Thr Asp Asn Lys Ser Thr
                 85                  90                  95

Phe Asp Gln Phe Tyr Leu Tyr Asn Gly Glu Glu Tyr Thr Val Lys Thr
            100                 105                 110

Gln Glu Ala Thr Asn Lys Asn Met Trp Leu Thr Thr Ser Glu Phe Arg
            115                 120                 125

Leu Lys Lys Trp Phe Asp Gly Glu Asp Cys Ile Met His Leu Arg Ser
130                 135                 140

Leu Val Arg Lys Met Glu Asp Ser Lys Arg Thr Val Pro Pro Met
145                 150                 155                 160

Val
```

<210> SEQ ID NO 21
<211> LENGTH: 580
<212> TYPE: PRT
<213> ORGANISM: Artificial Sequence
<220> FEATURE:
<223> OTHER INFORMATION: Synthetic peptide ULBP1-alpha3-iFv.2

<400> SEQUENCE: 21

```
Met Gly Leu Gly Pro Val Phe Leu Leu Leu Ala Gly Ile Phe Pro Phe
  1               5                  10                  15

Ala Pro Pro Gly Ala Ala Ala Glu Pro His Cys Leu Cys Tyr Asp Phe
             20                  25                  30

Ile Ile Thr Pro Lys Ser Arg Pro Glu Pro Gln Trp Cys Glu Val Gln
         35                  40                  45

Gly Leu Val Asp Glu Arg Pro Phe Leu His Tyr Asp Cys Val Asn His
 50                  55                  60

Lys Ala Lys Ala Phe Ala Ser Leu Gly Lys Lys Val Asn Val Thr Lys
 65                  70                  75                  80

Thr Trp Glu Glu Gln Thr Glu Thr Leu Arg Asp Val Val Asp Phe Leu
                 85                  90                  95

Lys Gly Gln Leu Leu Asp Ile Gln Val Glu Asn Leu Ile Pro Ile Glu
            100                 105                 110

Pro Leu Thr Leu Gln Ala Arg Met Ser Cys Glu His Glu Ala His Gly
            115                 120                 125

His Gly Arg Gly Ser Trp Gln Phe Leu Phe Asn Gly Gln Lys Phe Leu
            130                 135                 140

Leu Phe Asp Ser Asn Asn Arg Lys Trp Thr Ala Leu His Pro Gly Ala
145                 150                 155                 160

Lys Lys Met Thr Glu Lys Trp Glu Lys Asn Arg Asp Val Thr Met Phe
                165                 170                 175

Phe Gln Lys Ile Ser Leu Gly Asp Cys Lys Met Trp Leu Glu Glu Phe
            180                 185                 190

Leu Met Tyr Trp Glu Gln Met Leu Asp Pro Thr Lys Pro Pro Met Val
            195                 200                 205

Gln Val Thr Arg Ser Glu Ala Ser Gly Gly Ser Gly Asp Arg Val Thr
            210                 215                 220
```

```
Ile Thr Cys Arg Ala Ser Gln Asp Val Ser Thr Ala Val Ala Trp Tyr
225                 230                 235                 240

Gln Gln Lys Pro Gly Lys Ala Pro Lys Leu Leu Ile Tyr Ser Ala Ser
                245                 250                 255

Phe Leu Tyr Ser Gly Val Pro Ser Arg Phe Ser Gly Ser Gly Ser Gly
            260                 265                 270

Thr Asp Phe Thr Leu Thr Ile Ser Ser Leu Gln Pro Glu Asp Phe Ala
        275                 280                 285

Thr Tyr Tyr Cys Gln Gln Ser Tyr Thr Thr Pro Pro Thr Phe Gly Gln
    290                 295                 300

Gly Thr Lys Val Glu Ile Lys Gly Gly Ser Ser Arg Ser Ser Ser Ser
305                 310                 315                 320

Gly Gly Gly Gly Ser Gly Gly Gly Glu Val Gln Leu Val Glu Ser
                325                 330                 335

Gly Gly Gly Leu Val Gln Pro Gly Gly Ser Leu Arg Leu Ser Cys Ala
            340                 345                 350

Ala Ser Gly Phe Thr Phe Ser Thr Gly Ile Ser Trp Val Arg Gln
    355                 360                 365

Ala Pro Gly Lys Gly Leu Glu Trp Val Gly Arg Ile Tyr Pro Thr Asn
370                 375                 380

Gly Ser Thr Asn Tyr Ala Asp Ser Val Lys Gly Arg Phe Thr Ile Ser
385                 390                 395                 400

Ala Asp Thr Ser Lys Asn Thr Ala Tyr Leu Gln Met Asn Ser Leu Arg
                405                 410                 415

Ala Glu Asp Thr Ala Val Tyr Tyr Cys Ala Arg Thr Tyr Gly Ile Tyr
            420                 425                 430

Asp Leu Tyr Val Asp Tyr Thr Glu Tyr Val Met Asp Tyr Trp Gly Gln
        435                 440                 445

Gly Thr Leu Val Thr Val Ser Ser Gly Gly Ser Ser Arg Ser Ser Ser
    450                 455                 460

Ser Gly Gly Gly Gly Ser Gly Gly Gly Asp Ile Gln Met Thr Gln
465                 470                 475                 480

Ser Pro Ser Ser Leu Ser Ala Ser Gly Gly Ser Gly Gln Ile Thr Val
                485                 490                 495

Thr Cys Arg Ala Ser Gly Phe Tyr Pro Trp Asn Ile Thr Leu Ser Trp
            500                 505                 510

Arg Gln Asp Gly Val Ser Leu Ser His Asp Thr Gln Gln Trp Gly Asp
        515                 520                 525

Val Leu Pro Asp Gly Gln Gly Thr Tyr Gln Thr Trp Val Ala Thr Arg
    530                 535                 540

Ile Ser Gln Gly Glu Glu Gln Arg Phe Thr Cys Tyr Met Glu His Ser
545                 550                 555                 560

Gly Gln His Ser Thr His Pro Val Pro Ser Gly Lys Gly Ser His His
                565                 570                 575

His His His His
        580

<210> SEQ ID NO 22
<211> LENGTH: 582
<212> TYPE: PRT
<213> ORGANISM: Artificial Sequence
<220> FEATURE:
<223> OTHER INFORMATION: Synthetic peptide ULBP2-alpha3-iFv.2

<400> SEQUENCE: 22
```

-continued

```
Met Gly Leu Gly Pro Val Phe Leu Leu Ala Gly Ile Phe Pro Phe
1               5                   10                  15

Ala Pro Pro Gly Ala Ala Glu Pro His Ser Leu Cys Tyr Asp Ile
            20                  25                  30

Thr Val Ile Pro Lys Phe Arg Pro Gly Pro Arg Trp Cys Ala Val Gln
            35                  40                  45

Gly Gln Val Asp Glu Lys Thr Phe Leu His Tyr Asp Cys Gly Asn Lys
    50                  55                  60

Thr Val Thr Pro Val Ser Pro Leu Gly Lys Lys Leu Asn Val Thr Thr
65                  70                  75                  80

Ala Trp Lys Ala Gln Asn Pro Val Leu Arg Glu Val Val Asp Ile Leu
                85                  90                  95

Thr Glu Gln Leu Arg Asp Ile Gln Leu Glu Asn Tyr Thr Pro Lys Glu
            100                 105                 110

Pro Leu Thr Leu Gln Ala Arg Met Ser Cys Glu Gln Lys Ala Glu Gly
            115                 120                 125

His Ser Ser Gly Ser Trp Gln Phe Ser Phe Asp Gly Gln Ile Phe Leu
    130                 135                 140

Leu Phe Asp Ser Glu Lys Arg Met Trp Thr Thr Val His Pro Gly Ala
145                 150                 155                 160

Arg Lys Met Lys Glu Lys Trp Glu Asn Asp Lys Val Val Ala Met Ser
                165                 170                 175

Phe His Tyr Phe Ser Met Gly Asp Cys Ile Gly Trp Leu Glu Asp Phe
            180                 185                 190

Leu Met Gly Met Asp Ser Thr Leu Glu Pro Ser Ala Gly Ala Pro Pro
            195                 200                 205

Met Val Gln Val Thr Arg Ser Glu Ala Ser Gly Gly Ser Gly Asp Arg
    210                 215                 220

Val Thr Ile Thr Cys Arg Ala Ser Gln Asp Val Ser Thr Ala Val Ala
225                 230                 235                 240

Trp Tyr Gln Gln Lys Pro Gly Lys Ala Pro Lys Leu Leu Ile Tyr Ser
                245                 250                 255

Ala Ser Phe Leu Tyr Ser Gly Val Pro Ser Arg Phe Ser Gly Ser Gly
            260                 265                 270

Ser Gly Thr Asp Phe Thr Leu Thr Ile Ser Ser Leu Gln Pro Glu Asp
            275                 280                 285

Phe Ala Thr Tyr Tyr Cys Gln Gln Ser Tyr Thr Thr Pro Pro Thr Phe
    290                 295                 300

Gly Gln Gly Thr Lys Val Glu Ile Lys Gly Gly Ser Ser Arg Ser Ser
305                 310                 315                 320

Ser Ser Gly Gly Gly Gly Ser Gly Gly Gly Gly Glu Val Gln Leu Val
                325                 330                 335

Glu Ser Gly Gly Gly Leu Val Gln Pro Gly Gly Ser Leu Arg Leu Ser
            340                 345                 350

Cys Ala Ala Ser Gly Phe Thr Phe Thr Ser Thr Gly Ile Ser Trp Val
            355                 360                 365

Arg Gln Ala Pro Gly Lys Gly Leu Glu Trp Val Gly Arg Ile Tyr Pro
    370                 375                 380

Thr Asn Gly Ser Thr Asn Tyr Ala Asp Ser Val Lys Gly Arg Phe Thr
385                 390                 395                 400

Ile Ser Ala Asp Thr Ser Lys Asn Thr Ala Tyr Leu Gln Met Asn Ser
                405                 410                 415

Leu Arg Ala Glu Asp Thr Ala Val Tyr Tyr Cys Ala Arg Thr Tyr Gly
```

```
                420             425             430
Ile Tyr Asp Leu Tyr Val Asp Tyr Thr Glu Tyr Val Met Asp Tyr Trp
            435                 440                 445
Gly Gln Gly Thr Leu Val Thr Val Ser Ser Gly Gly Ser Ser Arg Ser
        450                 455                 460
Ser Ser Ser Gly Gly Gly Gly Ser Gly Gly Gly Gly Asp Ile Gln Met
465                 470                 475                 480
Thr Gln Ser Pro Ser Ser Leu Ser Ala Ser Gly Gly Ser Gly Gln Ile
                485                 490                 495
Thr Val Thr Cys Arg Ala Ser Gly Phe Tyr Pro Trp Asn Ile Thr Leu
            500                 505                 510
Ser Trp Arg Gln Asp Gly Val Ser Leu Ser His Asp Thr Gln Gln Trp
        515                 520                 525
Gly Asp Val Leu Pro Asp Gly Gln Gly Thr Tyr Gln Thr Trp Val Ala
        530                 535                 540
Thr Arg Ile Ser Gln Gly Glu Glu Gln Arg Phe Thr Cys Tyr Met Glu
545                 550                 555                 560
His Ser Gly Gln His Ser Thr His Pro Val Pro Ser Gly Lys Gly Ser
                565                 570                 575
His His His His His His
            580

<210> SEQ ID NO 23
<211> LENGTH: 580
<212> TYPE: PRT
<213> ORGANISM: Artificial Sequence
<220> FEATURE:
<223> OTHER INFORMATION: Synthetic peptide ULBP3-alpha3-iFv.2

<400> SEQUENCE: 23

Met Gly Leu Gly Pro Val Phe Leu Leu Leu Ala Gly Ile Phe Pro Phe
1               5                   10                  15
Ala Pro Pro Gly Ala Ala Ala Glu Pro His Ser Leu Trp Tyr Asn Phe
            20                  25                  30
Thr Ile Ile His Leu Pro Arg His Gly Gln Gln Trp Cys Glu Val Gln
        35                  40                  45
Ser Gln Val Asp Gln Lys Asn Phe Leu Ser Tyr Asp Cys Gly Ser Asp
    50                  55                  60
Lys Val Leu Ser Met Gly His Leu Glu Glu Gln Leu Tyr Ala Thr Asp
65                  70                  75                  80
Ala Trp Gly Lys Gln Leu Glu Met Leu Arg Glu Val Gly Gln Arg Leu
                85                  90                  95
Arg Leu Glu Leu Ala Asp Thr Glu Leu Glu Asp Phe Thr Pro Ser Gly
            100                 105                 110
Pro Leu Thr Leu Gln Val Arg Met Ser Cys Glu Cys Glu Ala Asp Gly
        115                 120                 125
Tyr Ile Arg Gly Ser Trp Gln Phe Ser Phe Asp Gly Arg Lys Phe Leu
    130                 135                 140
Leu Phe Asp Ser Asn Asn Arg Lys Trp Thr Val Val His Ala Gly Ala
145                 150                 155                 160
Arg Arg Met Lys Glu Lys Trp Glu Lys Asp Ser Gly Leu Thr Thr Phe
                165                 170                 175
Phe Lys Met Val Ser Met Arg Asp Cys Lys Ser Trp Leu Arg Asp Phe
            180                 185                 190
Leu Met His Arg Lys Lys Arg Leu Glu Pro Thr Ala Pro Pro Met Val
```

```
            195                 200                 205
Gln Val Thr Arg Ser Glu Ala Ser Gly Gly Ser Gly Asp Arg Val Thr
210                 215                 220

Ile Thr Cys Arg Ala Ser Gln Asp Val Ser Thr Ala Val Ala Trp Tyr
225                 230                 235                 240

Gln Gln Lys Pro Gly Lys Ala Pro Lys Leu Leu Ile Tyr Ser Ala Ser
                245                 250                 255

Phe Leu Tyr Ser Gly Val Pro Ser Arg Phe Ser Gly Ser Gly Ser Gly
            260                 265                 270

Thr Asp Phe Thr Leu Thr Ile Ser Ser Leu Gln Pro Glu Asp Phe Ala
            275                 280                 285

Thr Tyr Tyr Cys Gln Gln Ser Tyr Thr Thr Pro Pro Thr Phe Gly Gln
290                 295                 300

Gly Thr Lys Val Glu Ile Lys Gly Gly Ser Arg Ser Ser Ser Ser Ser
305                 310                 315                 320

Gly Gly Gly Gly Ser Gly Gly Gly Glu Val Gln Leu Val Glu Ser
                325                 330                 335

Gly Gly Gly Leu Val Gln Pro Gly Gly Ser Leu Arg Leu Ser Cys Ala
            340                 345                 350

Ala Ser Gly Phe Thr Phe Thr Ser Thr Gly Ile Ser Trp Val Arg Gln
            355                 360                 365

Ala Pro Gly Lys Gly Leu Glu Trp Val Gly Arg Ile Tyr Pro Thr Asn
370                 375                 380

Gly Ser Thr Asn Tyr Ala Asp Ser Val Lys Gly Arg Phe Thr Ile Ser
385                 390                 395                 400

Ala Asp Thr Ser Lys Asn Thr Ala Tyr Leu Gln Met Asn Ser Leu Arg
                405                 410                 415

Ala Glu Asp Thr Ala Val Tyr Tyr Cys Ala Arg Thr Tyr Gly Ile Tyr
            420                 425                 430

Asp Leu Tyr Val Asp Tyr Thr Glu Tyr Val Met Asp Tyr Trp Gly Gln
            435                 440                 445

Gly Thr Leu Val Thr Val Ser Ser Gly Gly Ser Ser Arg Ser Ser Ser
450                 455                 460

Ser Gly Gly Gly Gly Ser Gly Gly Gly Gly Asp Ile Gln Met Thr Gln
465                 470                 475                 480

Ser Pro Ser Ser Leu Ser Ala Ser Gly Gly Ser Gly Gln Ile Thr Val
                485                 490                 495

Thr Cys Arg Ala Ser Gly Phe Tyr Pro Trp Asn Ile Thr Leu Ser Trp
            500                 505                 510

Arg Gln Asp Gly Val Ser Leu Ser His Asp Thr Gln Gln Trp Gly Asp
            515                 520                 525

Val Leu Pro Asp Gly Gln Gly Thr Tyr Gln Thr Trp Val Ala Thr Arg
530                 535                 540

Ile Ser Gln Gly Glu Glu Gln Arg Phe Thr Cys Tyr Met Glu His Ser
545                 550                 555                 560

Gly Gln His Ser Thr His Pro Val Pro Ser Gly Lys Gly Ser His His
                565                 570                 575

His His His His
            580

<210> SEQ ID NO 24
<211> LENGTH: 580
<212> TYPE: PRT
<213> ORGANISM: Artificial Sequence
```

<220> FEATURE:
<223> OTHER INFORMATION: Synthetic peptide ULBP4-alpha3-iFv.2

<400> SEQUENCE: 24

```
Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Cys Phe Asn Phe
                20                  25                  30

Thr Ile Lys Ser Leu Ser Arg Pro Gly Gln Pro Trp Cys Glu Ala Gln
            35                  40                  45

Val Phe Leu Asn Lys Asn Leu Phe Leu Gln Tyr Asn Ser Asp Asn Asn
        50                  55                  60

Met Val Lys Pro Leu Gly Leu Leu Gly Lys Lys Val Tyr Ala Thr Ser
65                  70                  75                  80

Thr Trp Gly Glu Leu Thr Gln Thr Leu Gly Glu Val Gly Arg Asp Leu
                85                  90                  95

Arg Met Leu Leu Cys Asp Ile Lys Pro Gln Ile Lys Thr Ser Asp Pro
            100                 105                 110

Ser Thr Leu Gln Val Glu Met Phe Cys Gln Arg Glu Ala Glu Arg Cys
        115                 120                 125

Thr Gly Ala Ser Trp Gln Phe Ala Thr Asn Gly Glu Lys Ser Leu Leu
    130                 135                 140

Phe Asp Ala Met Asn Met Thr Trp Thr Val Ile Asn His Glu Ala Ser
145                 150                 155                 160

Lys Ile Lys Glu Thr Trp Lys Lys Asp Arg Gly Leu Glu Lys Tyr Phe
                165                 170                 175

Arg Lys Leu Ser Lys Gly Asp Cys Asp His Trp Leu Arg Glu Phe Leu
            180                 185                 190

Gly His Trp Glu Ala Met Pro Glu Pro Thr Val Ser Pro Pro Met Val
        195                 200                 205

Gln Val Thr Arg Ser Glu Ala Ser Gly Gly Ser Gly Asp Arg Val Thr
    210                 215                 220

Ile Thr Cys Arg Ala Ser Gln Asp Val Ser Thr Ala Val Ala Trp Tyr
225                 230                 235                 240

Gln Gln Lys Pro Gly Lys Ala Pro Lys Leu Leu Ile Tyr Ser Ala Ser
                245                 250                 255

Phe Leu Tyr Ser Gly Val Pro Ser Arg Phe Ser Gly Ser Gly Ser Gly
            260                 265                 270

Thr Asp Phe Thr Leu Thr Ile Ser Ser Leu Gln Pro Glu Asp Phe Ala
        275                 280                 285

Thr Tyr Tyr Cys Gln Gln Ser Tyr Thr Thr Pro Pro Thr Phe Gly Gln
    290                 295                 300

Gly Thr Lys Val Glu Ile Lys Gly Gly Ser Arg Ser Ser Ser Ser Ser
305                 310                 315                 320

Gly Gly Gly Gly Ser Gly Gly Gly Glu Val Gln Leu Val Glu Ser
                325                 330                 335

Gly Gly Gly Leu Val Gln Pro Gly Gly Ser Leu Arg Leu Ser Cys Ala
            340                 345                 350

Ala Ser Gly Phe Thr Phe Thr Ser Thr Gly Ile Ser Trp Val Arg Gln
        355                 360                 365

Ala Pro Gly Lys Gly Leu Glu Trp Val Gly Arg Ile Tyr Pro Thr Asn
    370                 375                 380

Gly Ser Thr Asn Tyr Ala Asp Ser Val Lys Gly Arg Phe Thr Ile Ser
385                 390                 395                 400
```

Ala Asp Thr Ser Lys Asn Thr Ala Tyr Leu Gln Met Asn Ser Leu Arg
            405                 410                 415

Ala Glu Asp Thr Ala Val Tyr Tyr Cys Ala Arg Thr Tyr Gly Ile Tyr
        420                 425                 430

Asp Leu Tyr Val Asp Tyr Thr Glu Tyr Val Met Asp Tyr Trp Gly Gln
    435                 440                 445

Gly Thr Leu Val Thr Val Ser Ser Gly Gly Ser Ser Arg Ser Ser Ser
450                 455                 460

Ser Gly Gly Gly Gly Ser Gly Gly Gly Asp Ile Gln Met Thr Gln
465                 470                 475                 480

Ser Pro Ser Ser Leu Ser Ala Ser Gly Gly Ser Gly Gln Ile Thr Val
                485                 490                 495

Thr Cys Arg Ala Ser Gly Phe Tyr Pro Trp Asn Ile Thr Leu Ser Trp
        500                 505                 510

Arg Gln Asp Gly Val Ser Leu Ser His Asp Thr Gln Gln Trp Gly Asp
    515                 520                 525

Val Leu Pro Asp Gly Gln Gly Thr Tyr Gln Thr Trp Val Ala Thr Arg
530                 535                 540

Ile Ser Gln Gly Glu Glu Gln Arg Phe Thr Cys Tyr Met Glu His Ser
545                 550                 555                 560

Gly Gln His Ser Thr His Pro Val Pro Ser Gly Lys Gly Ser His His
                565                 570                 575

His His His His
        580

<210> SEQ ID NO 25
<211> LENGTH: 582
<212> TYPE: PRT
<213> ORGANISM: Artificial Sequence
<220> FEATURE:
<223> OTHER INFORMATION: Synthetic peptide ULBP6-alpha3-iFv.2

<400> SEQUENCE: 25

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Cys Tyr Asp Ile
            20                  25                  30

Thr Val Ile Pro Lys Phe Arg Pro Gly Pro Arg Trp Cys Ala Val Gln
        35                  40                  45

Gly Gln Val Asp Glu Lys Thr Phe Leu His Tyr Asp Cys Gly Asn Lys
    50                  55                  60

Thr Val Thr Pro Val Ser Pro Leu Gly Lys Lys Leu Asn Val Thr Thr
65                  70                  75                  80

Ala Trp Lys Ala Gln Asn Pro Val Leu Arg Glu Val Val Asp Ile Leu
                85                  90                  95

Thr Glu Gln Leu Leu Asp Ile Gln Leu Glu Asn Tyr Thr Pro Lys Glu
            100                 105                 110

Pro Leu Thr Leu Gln Ala Arg Met Ser Cys Glu Gln Lys Ala Glu Gly
        115                 120                 125

His Ser Ser Gly Ser Trp Gln Phe Ser Ile Asp Gly Gln Thr Phe Leu
    130                 135                 140

Leu Phe Asp Ser Glu Lys Arg Met Trp Thr Thr Val His Pro Gly Ala
145                 150                 155                 160

Arg Lys Met Lys Glu Lys Trp Glu Asn Asp Lys Asp Val Ala Met Ser
                165                 170                 175

```
Phe His Tyr Ile Ser Met Gly Asp Cys Ile Gly Trp Leu Glu Asp Phe
            180                 185                 190

Leu Met Gly Met Asp Ser Thr Leu Glu Pro Ser Ala Gly Ala Pro Pro
        195                 200                 205

Met Val Gln Val Thr Arg Ser Glu Ala Ser Gly Ser Gly Asp Arg
210                 215                 220

Val Thr Ile Thr Cys Arg Ala Ser Gln Asp Val Ser Thr Ala Val Ala
225                 230                 235                 240

Trp Tyr Gln Gln Lys Pro Gly Lys Ala Pro Lys Leu Leu Ile Tyr Ser
                245                 250                 255

Ala Ser Phe Leu Tyr Ser Gly Val Pro Ser Arg Phe Ser Gly Ser Gly
            260                 265                 270

Ser Gly Thr Asp Phe Thr Leu Thr Ile Ser Ser Leu Gln Pro Glu Asp
            275                 280                 285

Phe Ala Thr Tyr Tyr Cys Gln Gln Ser Tyr Thr Thr Pro Pro Thr Phe
        290                 295                 300

Gly Gln Gly Thr Lys Val Glu Ile Lys Gly Gly Ser Arg Ser Ser
305                 310                 315                 320

Ser Ser Gly Gly Gly Gly Ser Gly Gly Gly Gly Glu Val Gln Leu Val
                325                 330                 335

Glu Ser Gly Gly Gly Leu Val Gln Pro Gly Gly Ser Leu Arg Leu Ser
            340                 345                 350

Cys Ala Ala Ser Gly Phe Thr Phe Thr Ser Thr Gly Ile Ser Trp Val
        355                 360                 365

Arg Gln Ala Pro Gly Lys Gly Leu Glu Trp Val Gly Arg Ile Tyr Pro
370                 375                 380

Thr Asn Gly Ser Thr Asn Tyr Ala Asp Ser Val Lys Gly Arg Phe Thr
385                 390                 395                 400

Ile Ser Ala Asp Thr Ser Lys Asn Thr Ala Tyr Leu Gln Met Asn Ser
                405                 410                 415

Leu Arg Ala Glu Asp Thr Ala Val Tyr Tyr Cys Ala Arg Thr Tyr Gly
            420                 425                 430

Ile Tyr Asp Leu Tyr Val Asp Tyr Thr Glu Tyr Val Met Asp Tyr Trp
        435                 440                 445

Gly Gln Gly Thr Leu Val Thr Val Ser Ser Gly Gly Ser Ser Arg Ser
    450                 455                 460

Ser Ser Ser Gly Gly Gly Gly Ser Gly Gly Gly Gly Asp Ile Gln Met
465                 470                 475                 480

Thr Gln Ser Pro Ser Ser Leu Ser Ala Ser Gly Gly Ser Gly Gln Ile
                485                 490                 495

Thr Val Thr Cys Arg Ala Ser Gly Phe Tyr Pro Trp Asn Ile Thr Leu
            500                 505                 510

Ser Trp Arg Gln Asp Gly Val Ser Leu Ser His Asp Thr Gln Gln Trp
        515                 520                 525

Gly Asp Val Leu Pro Asp Gly Gln Gly Thr Tyr Gln Thr Trp Val Ala
    530                 535                 540

Thr Arg Ile Ser Gln Gly Glu Glu Gln Arg Phe Thr Cys Tyr Met Glu
545                 550                 555                 560

His Ser Gly Gln His Ser Thr His Pro Val Pro Ser Gly Lys Gly Ser
                565                 570                 575

His His His His His His
            580
```

<210> SEQ ID NO 26
<211> LENGTH: 553
<212> TYPE: PRT
<213> ORGANISM: Artificial Sequence
<220> FEATURE:
<223> OTHER INFORMATION: Synthetic peptide OMCP-alpha3-iFv.2

<400> SEQUENCE: 26

```
Met Gly Leu Gly Pro Val Phe Leu Leu Leu Ala Gly Ile Phe Pro Phe
1               5                   10                  15

Ala Pro Pro Gly Ala Ala Ala Glu Pro His Lys Leu Ala Phe Asn Phe
            20                  25                  30

Asn Leu Glu Ile Asn Gly Ser Asp Thr His Ser Thr Val Asp Val Tyr
        35                  40                  45

Leu Asp Asp Ser Gln Ile Ile Thr Phe Asp Gly Lys Asp Ile Arg Pro
    50                  55                  60

Thr Ile Pro Phe Met Ile Gly Asp Glu Ile Phe Leu Pro Phe Tyr Lys
65                  70                  75                  80

Asn Val Phe Ser Glu Phe Ser Leu Phe Arg Arg Val Pro Thr Ser
                85                  90                  95

Thr Pro Tyr Glu Asp Leu Thr Tyr Phe Tyr Glu Cys Tyr Thr Asp
            100                 105                 110

Asn Lys Ser Thr Phe Asp Gln Phe Tyr Leu Tyr Asn Gly Glu Glu Tyr
        115                 120                 125

Thr Val Lys Thr Gln Glu Ala Thr Asn Lys Asn Met Trp Leu Thr Thr
    130                 135                 140

Ser Glu Phe Arg Leu Lys Lys Trp Phe Asp Gly Glu Asp Cys Ile Met
145                 150                 155                 160

His Leu Arg Ser Leu Val Arg Lys Met Glu Asp Ser Lys Arg Arg Thr
                165                 170                 175

Val Pro Pro Met Val Gln Val Thr Arg Ser Glu Ala Ser Gly Gly Ser
            180                 185                 190

Gly Asp Arg Val Thr Ile Thr Cys Arg Ala Ser Gln Asp Val Ser Thr
        195                 200                 205

Ala Val Ala Trp Tyr Gln Gln Lys Pro Gly Lys Ala Pro Lys Leu Leu
    210                 215                 220

Ile Tyr Ser Ala Ser Phe Leu Tyr Ser Gly Val Pro Ser Arg Phe Ser
225                 230                 235                 240

Gly Ser Gly Ser Gly Thr Asp Phe Thr Leu Thr Ile Ser Ser Leu Gln
                245                 250                 255

Pro Glu Asp Phe Ala Thr Tyr Tyr Cys Gln Gln Ser Tyr Thr Thr Pro
            260                 265                 270

Pro Thr Phe Gly Gln Gly Thr Lys Val Glu Ile Lys Gly Gly Ser Ser
        275                 280                 285

Arg Ser Ser Ser Gly Gly Gly Gly Ser Gly Gly Gly Gly Glu Val
    290                 295                 300

Gln Leu Val Glu Ser Gly Gly Gly Leu Val Gln Pro Gly Gly Ser Leu
305                 310                 315                 320

Arg Leu Ser Cys Ala Ala Ser Gly Phe Thr Phe Thr Ser Thr Gly Ile
                325                 330                 335

Ser Trp Val Arg Gln Ala Pro Gly Lys Gly Leu Glu Trp Val Gly Arg
            340                 345                 350

Ile Tyr Pro Thr Asn Gly Ser Thr Asn Tyr Ala Asp Ser Val Lys Gly
        355                 360                 365
```

Arg Phe Thr Ile Ser Ala Asp Thr Ser Lys Asn Thr Ala Tyr Leu Gln
370                 375                 380

Met Asn Ser Leu Arg Ala Glu Asp Thr Ala Val Tyr Tyr Cys Ala Arg
385                 390                 395                 400

Thr Tyr Gly Ile Tyr Asp Leu Tyr Val Asp Tyr Thr Glu Tyr Val Met
            405                 410                 415

Asp Tyr Trp Gly Gln Gly Thr Leu Val Thr Val Ser Ser Gly Gly Ser
            420                 425                 430

Ser Arg Ser Ser Ser Gly Gly Gly Ser Gly Gly Gly Asp
            435                 440                 445

Ile Gln Met Thr Gln Ser Pro Ser Ser Leu Ser Ala Ser Gly Gly Ser
450                 455                 460

Gly Gln Ile Thr Val Thr Cys Arg Ala Ser Gly Phe Tyr Pro Trp Asn
465                 470                 475                 480

Ile Thr Leu Ser Trp Arg Gln Asp Gly Val Ser Leu Ser His Asp Thr
                485                 490                 495

Gln Gln Trp Gly Asp Val Leu Pro Asp Gly Gly Tyr Gln Thr
            500                 505                 510

Trp Val Ala Thr Arg Ile Ser Gln Gly Glu Glu Gln Arg Phe Thr Cys
            515                 520                 525

Tyr Met Glu His Ser Gly Gln His Ser Thr His Pro Val Pro Ser Gly
530                 535                 540

Lys Gly Ser His His His His His His
545                 550

<210> SEQ ID NO 27
<211> LENGTH: 507
<212> TYPE: DNA
<213> ORGANISM: Artificial Sequence
<220> FEATURE:
<223> OTHER INFORMATION: Synthetic polynucleotide, encoding
      alpha1-alpha2 variant 15

<400> SEQUENCE: 27
gctgctgagc cacacagtct ccgctacaac cttacggtgt tgagctggga cggctctgtc      60
cagagtggct ttctgactga ggtacatctc gatggtcagc ccttcctccg atgcgacaga     120
caaaagtgca gggccaagcc acagggccaa tgggccgaag atgtacttgg caataagact     180
tgggacagag aaaccagaga tctgactggc tggggtaagg acttacgcat gactctcgca     240
cacattaaag accagaagga aggtcttcat tcgctccagg aaattagagt ctgtgaaatc     300
catgaagaca acagcacaag aagttcccaa catttctact acgacggcga gctgttctta     360
tcacagaatt tagagaccaa cgagtggaca atgccccaaa gctcgagggc ccagaccctc     420
gctatgaatg tgaggaattt ccttaaggag gacgctatgg aaactgacac ccactaccat     480
gcgatgcgcg ccgattgcct gcaggaa                                        507

<210> SEQ ID NO 28
<211> LENGTH: 507
<212> TYPE: DNA
<213> ORGANISM: Artificial Sequence
<220> FEATURE:
<223> OTHER INFORMATION: Synthetic polynucleotide, encoding
      alpha1-alpha2 variant 16

<400> SEQUENCE: 28
gctgctgagc cacacagtct ccgctacaac cttacggtgt tgagctggga cggctctgtc      60
cagagtggct ttctgactga ggtacatctc gatggtcagc ccttcctccg atgcgacaga     120

```
caaaagtgca gggccaagcc acagggccaa tgggccgaag atgtacttgg caataagact    180
tgggacagag aaaccagaga tctgactggc tggggtaagg acttacgcat gactctcgca    240
cacattaaag accagaagga aggtcttcat tcgctccagg aaattagagt ctgtgaaatc    300
catgaagaca acagcacaag aagttcccaa catttctact acgacggcga gctgttctta    360
tcacagaatt tagagaccct cgagtggaca atgccccaaa gctcgagggc ccagaccctc    420
gctatgaatg tgaggaattt ccttaaggag gacgctatgg aaactgacac ccactaccat    480
gcgatgcgcg ccgattgcct gcaggaa                                        507

<210> SEQ ID NO 29
<211> LENGTH: 507
<212> TYPE: DNA
<213> ORGANISM: Artificial Sequence
<220> FEATURE:
<223> OTHER INFORMATION: Synthetic polynucleotide, encoding
      alpha1-alpha2 variant 17

<400> SEQUENCE: 29
gctgctgagc cacacagtct ccgctacaac cttacggtgt tgagctggga cggctctgtc     60
cagagtggct ttctgactga ggtacatctc gatggtcagc ccttcctccg atgcgacaga    120
caaaagtgca gggccaagcc acagggccaa tgggccgaag atgtacttgg caataagact    180
tgggacagag aaaccagaga tctgactctc tggggtaagg acttacgcat gactctcgca    240
cacattaaag accagaagga aggtcttcat tcgctccagg aaattagagt ctgtgaaatc    300
catgaagaca acagcacaag aagttcccaa catttctact acgacggcga gctgttctta    360
tcacagaatt tagagaccct cgagtggaca atgccccaaa gctcgagggc ccagaccctc    420
gctatgaatg tgaggaattt ccttaaggag gacgctatgg aaactgacac ccactaccat    480
gcgatgcgcg ccgattgcct gcaggaa                                        507

<210> SEQ ID NO 30
<211> LENGTH: 507
<212> TYPE: DNA
<213> ORGANISM: Artificial Sequence
<220> FEATURE:
<223> OTHER INFORMATION: Synthetic polynucleotide, encoding
      alpha1-alpha2 variant 18

<400> SEQUENCE: 30
gctgctgagc cacacagtct ccgctacaac cttacggtgt tgagctggga cggctctgtc     60
cagcccggct ttctgactga ggtacatctc gatggtcagc ccttcctccg atgcgacaga    120
caaaagtgca gggccaagcc acagggccaa tgggccgaag atgtacttgg caataagact    180
tgggacagag aaaccagaga tctgactctc tggggtaagg acttacgcat gactctcgca    240
cacattaaag accagaagga aggtcttcat tcgctccagg aaattagagt ctgtgaaatc    300
catgaagaca acagcacaag aagttcccaa catttctact acgacggcga gctgttctta    360
tcacagaatt tagagaccct cgagtggaca atgccccaaa gctcgagggc ccagaccctc    420
gctatgaatg tgaggaattt ccttaaggag gacgctatgg aaactgacac ccactaccat    480
gcgatgcgcg ccgattgcct gcaggaa                                        507

<210> SEQ ID NO 31
<211> LENGTH: 558
<212> TYPE: PRT
<213> ORGANISM: Artificial Sequence
<220> FEATURE:
```

<223> OTHER INFORMATION: Synthetic peptide MICA alpha1-alpha2 variant 15

<400> SEQUENCE: 31

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Asn Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400
```

```
Tyr Tyr Cys Ala Arg Thr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Ser
        435                 440                 445

Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
        530                 535                 540

Pro Val Pro Ser Gly Lys Gly Ser His His His His His
545                 550                 555

<210> SEQ ID NO 32
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 16

<400> SEQUENCE: 32

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205
```

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
        435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
530                 535                 540

Pro Val Pro Ser Gly Lys Gly Ser His His His His His His
545                 550                 555

<210> SEQ ID NO 33
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 17

<400> SEQUENCE: 33

Glu Pro His Ser Leu Arg Tyr Asn Leu Thr Val Leu Ser Trp Asp Gly
1               5                   10                  15

-continued

```
Ser Val Gln Ser Gly Phe Leu Thr Glu Val His Leu Asp Gly Gln Pro
            20                  25                  30
Phe Leu Arg Cys Asp Arg Gln Lys Cys Arg Ala Lys Pro Gln Gly Gln
        35                  40                  45
Trp Ala Glu Asp Val Leu Gly Asn Lys Thr Trp Asp Arg Glu Thr Arg
 50                  55                  60
Asp Leu Thr Leu Trp Gly Lys Asp Leu Arg Met Thr Leu Ala His Ile
 65                  70                  75                  80
Lys Asp Gln Lys Glu Gly Leu His Ser Leu Gln Glu Ile Arg Val Cys
                85                  90                  95
Glu Ile His Glu Asp Asn Ser Thr Arg Ser Ser Gln His Phe Tyr Tyr
            100                 105                 110
Asp Gly Glu Leu Phe Leu Ser Gln Asn Leu Glu Thr Leu Glu Trp Thr
        115                 120                 125
Met Pro Gln Ser Ser Arg Ala Gln Thr Leu Ala Met Asn Val Arg Asn
    130                 135                 140
Phe Leu Lys Glu Asp Ala Met Glu Thr Asp Thr His Tyr His Ala Met
145                 150                 155                 160
Arg Ala Asp Cys Leu Gln Glu Leu Arg Arg Tyr Leu Lys Ser Gly Val
                165                 170                 175
Val Leu Arg Arg Thr Val Pro Pro Met Val Gln Val Thr Arg Ser Glu
            180                 185                 190
Ala Ser Gly Gly Ser Gly Asp Arg Val Thr Ile Thr Cys Arg Ala Ser
        195                 200                 205
Gln Asp Val Ser Thr Ala Val Ala Trp Tyr Gln Gln Lys Pro Gly Lys
    210                 215                 220
Ala Pro Lys Leu Leu Ile Tyr Ser Ala Ser Phe Leu Tyr Ser Gly Val
225                 230                 235                 240
Pro Ser Arg Phe Ser Gly Ser Gly Ser Gly Thr Asp Phe Thr Leu Thr
                245                 250                 255
Ile Ser Ser Leu Gln Pro Glu Asp Phe Ala Thr Tyr Tyr Cys Gln Gln
            260                 265                 270
Ser Tyr Thr Thr Pro Pro Thr Phe Gly Gln Gly Thr Lys Val Glu Ile
        275                 280                 285
Lys Gly Gly Ser Ser Arg Ser Ser Ser Ser Gly Gly Gly Gly Ser Gly
    290                 295                 300
Gly Gly Gly Glu Val Gln Leu Val Glu Ser Gly Gly Gly Leu Val Gln
305                 310                 315                 320
Pro Gly Gly Ser Leu Arg Leu Ser Cys Ala Ala Ser Gly Phe Thr Phe
                325                 330                 335
Thr Ser Thr Gly Ile Ser Trp Val Arg Gln Ala Pro Gly Lys Gly Leu
            340                 345                 350
Glu Trp Val Gly Arg Ile Tyr Pro Thr Asn Gly Ser Thr Asn Tyr Ala
        355                 360                 365
Asp Ser Val Lys Gly Arg Phe Thr Ile Ser Ala Asp Thr Ser Lys Asn
    370                 375                 380
Thr Ala Tyr Leu Gln Met Asn Ser Leu Arg Ala Glu Asp Thr Ala Val
385                 390                 395                 400
Tyr Tyr Cys Ala Arg Thr Tyr Gly Ile Tyr Asp Leu Tyr Val Asp Tyr
                405                 410                 415
Thr Glu Tyr Val Met Asp Tyr Trp Gly Gln Gly Thr Leu Val Thr Val
            420                 425                 430
Ser Ser Gly Gly Ser Ser Arg Ser Ser Ser Ser Gly Gly Gly Gly Ser
```

```
                    435                 440                 445
Gly Gly Gly Gly Asp Ile Gln Met Thr Gln Ser Pro Ser Ser Leu Ser
            450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                    485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
        530                 535                 540

Pro Val Pro Ser Gly Lys Gly Ser His His His His His His
545                 550                 555
```

<210> SEQ ID NO 34
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 18

<400> SEQUENCE: 34

```
Glu Pro His Ser Leu Arg Tyr Asn Leu Thr Val Leu Ser Trp Asp Gly
1               5                   10                  15

Ser Val Gln Pro Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Leu Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
```

-continued

```
            245                 250                 255
Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Ser Gly Gly Gly Gly Ser Gly
290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
    370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Ser Gly Gly Gly Gly Ser
        435                 440                 445

Gly Gly Gly Gly Asp Ile Gln Met Thr Gln Ser Pro Ser Ser Leu Ser
    450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
    530                 535                 540

Pro Val Pro Ser Gly Lys Gly Ser His His His His His His
545                 550                 555
```

<210> SEQ ID NO 35
<211> LENGTH: 558
<212> TYPE: PRT
<213> ORGANISM: Artificial Sequence
<220> FEATURE:
<223> OTHER INFORMATION: Synthetic peptide MICA-WED

<400> SEQUENCE: 35

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
```

```
            50                  55                  60
Asp Leu Thr Gly Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Lys Glu Trp Thr
                115                 120                 125

Met Pro Gln Ser Ser Arg Ala Gln Thr Leu Ala Met Asn Val Arg Asn
                130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
                180                 185                 190

Ala Ser Gly Gly Ser Gly Asp Arg Val Thr Ile Thr Cys Arg Ala Ser
                195                 200                 205

Gln Asp Val Ser Thr Ala Val Ala Trp Tyr Gln Gln Lys Pro Gly Lys
                210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
                260                 265                 270

Ser Tyr Thr Thr Pro Pro Thr Phe Gly Gln Gly Thr Lys Val Glu Ile
                275                 280                 285

Lys Gly Gly Ser Ser Arg Ser Ser Ser Gly Gly Gly Gly Ser Gly
                290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
                340                 345                 350

Glu Trp Val Gly Arg Ile Tyr Pro Thr Asn Gly Ser Thr Asn Tyr Ala
                355                 360                 365

Asp Ser Val Lys Gly Arg Phe Thr Ile Ser Ala Asp Thr Ser Lys Asn
                370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
                420                 425                 430

Ser Ser Gly Gly Ser Ser Arg Ser Ser Ser Gly Gly Gly Gly Ser
                435                 440                 445

Gly Gly Gly Gly Asp Ile Gln Met Thr Gln Ser Pro Ser Ser Leu Ser
                450                 455                 460

Ala Ser Gly Gly Ser Gly Gln Ile Thr Val Thr Cys Arg Ala Ser Gly
465                 470                 475                 480
```

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
    530                 535                 540

Pro Val Pro Ser Gly Lys Gly Ser His His His His His
545                 550                 555

<210> SEQ ID NO 36
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 36

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr Leu Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 37
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 37

```
Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
        115                 120                 125

Met Pro Gln Ser Ser Arg Ala Gln Thr Leu Ala Met Asn Ile Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser
```

<210> SEQ ID NO 38
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 38

```
Glu Pro His Ser Leu Pro Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30
```

Phe Leu Arg Tyr Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Glu Glu Trp Thr
            115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
            195                 200                 205

Pro Trp Asn Ile Thr Leu Ser Trp Arg Gln Asp Gly Val Ser Leu Ser
            210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 39
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 39

Glu Pro His Ser Leu Arg Tyr Asn Leu Thr Val Leu Ser Trp Asp Gly
 1               5                  10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Glu Glu Trp Thr

```
            115                 120                 125
Val Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser

<210> SEQ ID NO 40
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 40

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205
```

```
Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser
```

<210> SEQ ID NO 41
<211> LENGTH: 274
<212> TYPE: PRT
<213> ORGANISM: Artificial Sequence
<220> FEATURE:
<223> OTHER INFORMATION: Synthetic peptide MICA

<400> SEQUENCE: 41

```
Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
                20                  25                  30

Phe Leu Arg Cys Asp Arg Gln Lys Cys Arg Ala Lys Pro Gln Gly Gln
                35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Glu Glu Trp Thr
                115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
                180                 185                 190

Ala Ser Glu Gly Asn Ile Thr Val Thr Cys Arg Ala Ser Gly Phe Tyr
                195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser
```

```
<210> SEQ ID NO 42
<211> LENGTH: 276
<212> TYPE: PRT
<213> ORGANISM: Artificial Sequence
<220> FEATURE:
<223> OTHER INFORMATION: Synthetic peptide MICA

<400> SEQUENCE: 42
```

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys
        275

```
<210> SEQ ID NO 43
<211> LENGTH: 306
<212> TYPE: PRT
<213> ORGANISM: Artificial Sequence
<220> FEATURE:
<223> OTHER INFORMATION: Synthetic peptide MICB

<400> SEQUENCE: 43
```

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

```
Phe Leu Arg Tyr Asp Arg Gln Lys Arg Ala Lys Pro Gln Gly Gln
            35                  40                  45

Trp Ala Glu Asp Val Leu Gly Ala Lys Thr Trp Asp Thr Glu Thr Glu
 50                  55                  60

Asp Leu Thr Glu Asn Gly Gln Asp Leu Arg Arg Thr Leu Thr His Ile
 65                  70                  75                  80

Lys Asp Gln Lys Gly Gly Leu His Ser Leu Gln Glu Ile Arg Val Cys
                 85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
            115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Leu Pro Pro Met Val Asn Val
                165                 170                 175

Ile Cys Ser Glu Val Ser Glu Gly Asn Ile Thr Val Thr Cys Arg Ala
            180                 185                 190

Ser Ser Phe Tyr Pro Arg Asn Ile Thr Leu Thr Trp Arg Gln Asp Gly
            195                 200                 205

Val Ser Leu Ser His Asn Thr Gln Gln Trp Gly Asp Val Leu Pro Asp
            210                 215                 220

Gly Asn Gly Thr Tyr Gln Thr Trp Val Ala Thr Arg Ile Arg Gln Gly
225                 230                 235                 240

Glu Glu Gln Arg Phe Thr Cys Tyr Met Glu His Ser Gly Asn His Gly
                245                 250                 255

Thr His Pro Val Pro Ser Gly Lys Ala Leu Val Leu Gln Ser Gln Arg
            260                 265                 270

Thr Asp Phe Pro Tyr Val Ser Ala Ala Met Pro Cys Phe Val Ile Ile
            275                 280                 285

Ile Ile Leu Cys Val Pro Cys Cys Lys Lys Lys Thr Ser Ala Ala Glu
290                 295                 300

Gly Pro
305

<210> SEQ ID NO 44
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 44

Glu Pro His Ser Leu Arg Tyr Asn Leu Met Val Leu Ser Gln Asp Gly
 1               5                  10                  15

Ser Val Gln Ser Gly Phe Leu Ala Glu Gly His Leu Asp Gly Gln Pro
                 20                  25                  30

Phe Leu Arg Tyr Asp Arg Gln Lys Arg Ala Lys Pro Gln Gly Gln
            35                  40                  45

Trp Ala Glu Asp Val Leu Gly Ala Glu Thr Trp Asp Thr Glu Thr Glu
 50                  55                  60

Asp Leu Thr Glu Asn Gly Gln Asp Leu Arg Arg Thr Leu Thr His Ile
 65                  70                  75                  80
```

```
Lys Asp Gln Lys Gly Gly Leu His Ser Leu Gln Glu Ile Arg Val Cys
                85                  90                  95

Glu Met His Glu Asp Ser Ser Thr Arg Gly Ser Arg His Phe Tyr Tyr
            100                 105                 110

Asn Gly Glu Leu Phe Leu Ser Gln Asn Leu Glu Thr Gln Glu Ser Thr
            115                 120                 125

Val Pro Gln Ser Ser Arg Ala Gln Thr Leu Ala Met Asn Val Thr Asn
        130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
            195                 200                 205

Pro Arg Asn Ile Thr Leu Thr Trp Arg Gln Asp Gly Val Ser Leu Ser
        210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
            275                 280                 285

Tyr Val Ser Ala Ala Met Pro Cys Phe Val Ile Ile Ile Leu Cys
        290                 295                 300

Val Pro Cys Cys Lys Lys Lys Thr Ser Ala Ala Glu Gly Pro
305                 310                 315

<210> SEQ ID NO 45
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 45

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Lys Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
            115                 120                 125
```

```
Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Ile Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
                260                 265                 270

Pro Ser Gly Lys Ala Leu Val Leu Gln Ser Gln Arg Thr Asp Phe Pro
            275                 280                 285

Tyr Val Ser Ala Ala Met Pro Cys Phe Val Ile Ile Ile Ile Leu Cys
290                 295                 300

Val Pro Cys Cys Lys Lys Lys Thr Ser Ala Ala Glu Gly Pro
305                 310                 315

<210> SEQ ID NO 46
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 46

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
                20                  25                  30

Phe Leu Arg Tyr Asp Arg Gln Lys Arg Arg Ala Lys Pro Gln Gly Gln
            35                  40                  45

Trp Ala Glu Asn Val Leu Gly Ala Lys Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
                100                 105                 110

Asp Gly Glu Leu Phe Leu Ser Gln Asn Leu Glu Thr Gln Glu Ser Thr
            115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175
```

-continued

```
Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
    210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Ile Leu Cys
    290                 295                 300

Val Pro Cys Cys Lys Lys Lys Thr Ser Ala Ala Glu Gly Pro
305                 310                 315
```

<210> SEQ ID NO 47
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 47

```
Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Glu Thr Trp Asp Thr Glu Thr Glu
    50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asn Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
    130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
    210                 215                 220
```

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Lys
            245                 250                 255

Phe Thr Cys Tyr Met Glu His Ser Gly Asn His Gly Thr His Pro Val
        260                 265                 270

Pro Ser Gly Lys Ala Leu Val Leu Gln Ser Gln Arg Thr Asp Phe Pro
    275                 280                 285

Tyr Val Ser Ala Ala Met Pro Cys Phe Val Ile Ile Ile Leu Cys
        290                 295                 300

Val Pro Cys Cys Lys Lys Lys Thr Ser Ala Ala Glu Gly Pro
305                 310                 315

<210> SEQ ID NO 48
<211> LENGTH: 318
<212> TYPE: PRT
<213> ORGANISM: Artificial Sequence
<220> FEATURE:
<223> OTHER INFORMATION: Synthetic peptide MICB

<400> SEQUENCE: 48

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Glu Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asn Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
            245                 250                 255

Phe Thr Cys Tyr Met Glu His Ser Gly Asn His Gly Thr His Pro Val
        260                 265                 270

```
Pro Ser Gly Lys Ala Leu Val Leu Gln Ser Gln Arg Thr Asp Phe Pro
            275                 280                 285
Tyr Val Ser Ala Ala Met Pro Cys Phe Val Ile Ile Ile Ile Leu Cys
            290                 295                 300
Val Pro Cys Cys Lys Lys Lys Thr Ser Ala Ala Glu Gly Pro
305             310                 315
```

<210> SEQ ID NO 49
<211> LENGTH: 244
<212> TYPE: PRT
<213> ORGANISM: Artificial Sequence
<220> FEATURE:
<223> OTHER INFORMATION: Synthetic peptide ULBP-1 (ACCESSION NO Q9BZM6)

<400> SEQUENCE: 49

```
Met Ala Ala Ala Ser Pro Ala Phe Leu Leu Cys Leu Pro Leu Leu
1               5                   10                  15
His Leu Ser Gly Trp Ser Arg Ala Gly Trp Val Asp Thr His Cys
            20                  25                  30
Leu Cys Tyr Asp Phe Ile Ile Thr Pro Lys Ser Arg Pro Glu Pro Gln
            35                  40                  45
Trp Cys Glu Val Gln Gly Leu Val Asp Glu Arg Pro Phe Leu His Tyr
    50                  55                  60
Asp Cys Val Asn His Lys Ala Lys Ala Phe Ala Ser Leu Gly Lys Lys
65                  70                  75                  80
Val Asn Val Thr Lys Thr Trp Glu Glu Gln Thr Glu Thr Leu Arg Asp
                85                  90                  95
Val Val Asp Phe Leu Lys Gly Gln Leu Leu Asp Ile Gln Val Glu Asn
                100                 105                 110
Leu Ile Pro Ile Glu Pro Leu Thr Leu Gln Ala Arg Met Ser Cys Glu
            115                 120                 125
His Glu Ala His Gly His Gly Arg Gly Ser Trp Gln Phe Leu Phe Asn
        130                 135                 140
Gly Gln Lys Phe Leu Leu Phe Asp Ser Asn Asn Arg Lys Trp Thr Ala
145                 150                 155                 160
Leu His Pro Gly Ala Lys Lys Met Thr Glu Lys Trp Glu Lys Asn Arg
                165                 170                 175
Asp Val Thr Met Phe Phe Gln Lys Ile Ser Leu Gly Asp Cys Lys Met
                180                 185                 190
Trp Leu Glu Glu Phe Leu Met Tyr Trp Glu Gln Met Leu Asp Pro Thr
            195                 200                 205
Lys Pro Pro Ser Leu Ala Pro Gly Thr Thr Gln Pro Lys Ala Met Ala
        210                 215                 220
Thr Thr Leu Ser Pro Trp Ser Leu Leu Ile Ile Phe Leu Cys Phe Ile
225                 230                 235                 240
Leu Ala Gly Arg
```

<210> SEQ ID NO 50
<211> LENGTH: 246
<212> TYPE: PRT
<213> ORGANISM: Artificial Sequence
<220> FEATURE:
<223> OTHER INFORMATION: Synthetic peptide ULBP-2 (ACCESSION NO Q9BZM5)

<400> SEQUENCE: 50

```
Met Ala Ala Ala Ala Thr Lys Ile Leu Leu Cys Leu Pro Leu Leu
1               5                   10                  15
```

Leu Leu Leu Ser Gly Trp Ser Arg Ala Gly Arg Ala Asp Pro His Ser
            20                  25                  30

Leu Cys Tyr Asp Ile Thr Val Ile Pro Lys Phe Arg Pro Gly Pro Arg
            35                  40                  45

Trp Cys Ala Val Gln Gly Gln Val Asp Glu Lys Thr Phe Leu His Tyr
        50                  55                  60

Asp Cys Gly Asn Lys Thr Val Thr Pro Val Ser Pro Leu Gly Lys Lys
65                  70                  75                  80

Leu Asn Val Thr Thr Ala Trp Lys Ala Gln Asn Pro Val Leu Arg Glu
                85                  90                  95

Val Val Asp Ile Leu Thr Glu Gln Leu Arg Asp Ile Gln Leu Glu Asn
            100                 105                 110

Tyr Thr Pro Lys Glu Pro Leu Thr Leu Gln Ala Arg Met Ser Cys Glu
        115                 120                 125

Gln Lys Ala Glu Gly His Ser Ser Gly Ser Trp Gln Phe Ser Phe Asp
    130                 135                 140

Gly Gln Ile Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Val Val Ala Met Ser Phe His Tyr Phe Ser Met Gly Asp Cys Ile Gly
            180                 185                 190

Trp Leu Glu Asp Phe Leu Met Gly Met Asp Ser Thr Leu Glu Pro Ser
        195                 200                 205

Ala Gly Ala Pro Leu Ala Met Ser Ser Gly Thr Thr Gln Leu Arg Ala
    210                 215                 220

Thr Ala Thr Thr Leu Ile Leu Cys Cys Leu Leu Ile Ile Leu Pro Cys
225                 230                 235                 240

Phe Ile Leu Pro Gly Ile
                245

<210> SEQ ID NO 51
<211> LENGTH: 244
<212> TYPE: PRT
<213> ORGANISM: Artificial Sequence
<220> FEATURE:
<223> OTHER INFORMATION: Synthetic peptide ULBP-3 (ACCESSION NO
      NP_078794)

<400> SEQUENCE: 51

Met Ala Ala Ala Ala Ser Pro Ala Ile Leu Pro Arg Leu Ala Ile Leu
1               5                   10                  15

Pro Tyr Leu Leu Phe Asp Trp Ser Gly Thr Gly Arg Ala Asp Ala His
            20                  25                  30

Ser Leu Trp Tyr Asn Phe Thr Ile Ile His Leu Pro Arg His Gly Gln
        35                  40                  45

Gln Trp Cys Glu Val Gln Ser Gln Val Asp Gln Lys Asn Phe Leu Ser
    50                  55                  60

Tyr Asp Cys Gly Ser Asp Lys Val Leu Ser Met Gly His Leu Glu Glu
65                  70                  75                  80

Gln Leu Tyr Ala Thr Asp Ala Trp Gly Lys Gln Leu Glu Met Leu Arg
                85                  90                  95

Glu Val Gly Gln Arg Leu Arg Leu Glu Leu Ala Asp Thr Glu Leu Glu
            100                 105                 110

Asp Phe Thr Pro Ser Gly Pro Leu Thr Leu Gln Val Arg Met Ser Cys
        115                 120                 125

```
Glu Cys Glu Ala Asp Gly Tyr Ile Arg Gly Ser Trp Gln Phe Ser Phe
    130                 135                 140

Asp Gly Arg Lys Phe Leu Leu Phe Asp Ser Asn Asn Arg Lys Trp Thr
145                 150                 155                 160

Val Val His Ala Gly Ala Arg Arg Met Lys Glu Lys Trp Glu Lys Asp
                165                 170                 175

Ser Gly Leu Thr Thr Phe Phe Lys Met Val Ser Met Arg Asp Cys Lys
                180                 185                 190

Ser Trp Leu Arg Asp Phe Leu Met His Arg Lys Lys Arg Leu Glu Pro
            195                 200                 205

Thr Ala Pro Pro Thr Met Ala Pro Gly Leu Ala Gln Pro Lys Ala Ile
    210                 215                 220

Ala Thr Thr Leu Ser Pro Trp Ser Phe Leu Ile Ile Leu Cys Phe Ile
225                 230                 235                 240

Leu Pro Gly Ile

<210> SEQ ID NO 52
<211> LENGTH: 263
<212> TYPE: PRT
<213> ORGANISM: Artificial Sequence
<220> FEATURE:
<223> OTHER INFORMATION: Synthetic peptide ULBP-4/RAET1E (ACCESSION NO
      Q8TD07)

<400> SEQUENCE: 52

Met Arg Arg Ile Ser Leu Thr Ser Ser Pro Val Arg Leu Leu Leu Phe
1               5                   10                  15

Leu Leu Leu Leu Leu Ile Ala Leu Glu Ile Met Val Gly Gly His Ser
                20                  25                  30

Leu Cys Phe Asn Phe Thr Ile Lys Ser Leu Ser Arg Pro Gly Gln Pro
            35                  40                  45

Trp Cys Glu Ala Gln Val Phe Leu Asn Lys Asn Leu Phe Leu Gln Tyr
        50                  55                  60

Asn Ser Asp Asn Asn Met Val Lys Pro Leu Gly Leu Leu Gly Lys Lys
65                  70                  75                  80

Val Tyr Ala Thr Ser Thr Trp Gly Glu Leu Thr Gln Thr Leu Gly Glu
                85                  90                  95

Val Gly Arg Asp Leu Arg Met Leu Leu Cys Asp Ile Lys Pro Gln Ile
                100                 105                 110

Lys Thr Ser Asp Pro Ser Thr Leu Gln Val Glu Met Phe Cys Gln Arg
            115                 120                 125

Glu Ala Glu Arg Cys Thr Gly Ala Ser Trp Gln Phe Ala Thr Asn Gly
    130                 135                 140

Glu Lys Ser Leu Leu Phe Asp Ala Met Asn Met Thr Trp Thr Val Ile
145                 150                 155                 160

Asn His Glu Ala Ser Lys Ile Lys Glu Thr Trp Lys Lys Asp Arg Gly
                165                 170                 175

Leu Glu Lys Tyr Phe Arg Lys Leu Ser Lys Gly Asp Cys Asp His Trp
                180                 185                 190

Leu Arg Glu Phe Leu Gly His Trp Glu Ala Met Pro Glu Pro Thr Val
            195                 200                 205

Ser Pro Val Asn Ala Ser Asp Ile His Trp Ser Ser Ser Ser Leu Pro
    210                 215                 220

Asp Arg Trp Ile Ile Leu Gly Ala Phe Ile Leu Leu Val Leu Met Gly
225                 230                 235                 240
```

```
Ile Val Leu Ile Cys Val Trp Trp Gln Asn Gly Glu Trp Gln Ala Gly
                245                 250                 255

Leu Trp Pro Leu Arg Thr Ser
            260
```

<210> SEQ ID NO 53
<211> LENGTH: 332
<212> TYPE: PRT
<213> ORGANISM: Artificial Sequence
<220> FEATURE:
<223> OTHER INFORMATION: Synthetic peptide ULBP-5 (ACCESSION NO Q6H3X3)

<400> SEQUENCE: 53

```
Met Ala Ala Ala Ser Pro Ala Phe Leu Leu Arg Leu Pro Leu Leu
1               5                   10                  15

Leu Leu Leu Ser Ser Trp Cys Arg Thr Gly Leu Ala Asp Pro His Ser
                20                  25                  30

Leu Cys Tyr Asp Ile Thr Val Pro Lys Phe Arg Pro Gly Pro Arg Trp
            35                  40                  45

Cys Ala Val Gln Gly Gln Val Asp Glu Lys Thr Phe Leu His Tyr Asp
    50                  55                  60

Cys Gly Ser Lys Thr Val Thr Pro Val Ser Pro Leu Gly Lys Lys Leu
65                  70                  75                  80

Asn Val Thr Thr Ala Trp Lys Ala Gln Asn Pro Val Leu Arg Glu Val
                85                  90                  95

Val Asp Leu Thr Glu Gln Leu Leu Asp Ile Gln Leu Glu Asn Tyr Ile
            100                 105                 110

Pro Lys Glu Pro Leu Thr Leu Gln Ala Arg Met Ser Cys Glu Gln Lys
        115                 120                 125

Ala Glu Gly His Gly Ser Gly Ser Trp Gln Leu Ser Phe Asp Gly Gln
    130                 135                 140

Ile Phe Leu Leu Phe Asp Ser Glu Asn Arg Met Trp Thr Thr Val His
145                 150                 155                 160

Pro Gly Ala Arg Lys Met Lys Glu Lys Trp Glu Asn Asp Lys Asp Met
                165                 170                 175

Thr Met Ser Phe His Tyr Ile Ser Met Gly Asp Cys Thr Gly Trp Leu
            180                 185                 190

Glu Asp Phe Leu Met Gly Met Asp Ser Thr Leu Glu Pro Ser Ala Gly
        195                 200                 205

Ala Pro Pro Thr Met Ser Ser Gly Thr Ala Gln Pro Arg Ala Thr Ala
    210                 215                 220

Thr Thr Leu Ile Leu Cys Cys Leu Leu Ile Met Cys Leu Leu Ile Cys
225                 230                 235                 240

Ser Arg His Ser Leu Thr Gln Ser His Gly His His Pro Gln Ser Leu
                245                 250                 255

Gln Pro Pro Pro His Pro Pro Leu Leu His Pro Thr Trp Leu Leu Arg
            260                 265                 270

Arg Val Leu Trp Ser Asp Ser Tyr Gln Ile Ala Lys Arg Pro Leu Ser
        275                 280                 285

Gly Gly His Val Thr Arg Val Thr Leu Pro Ile Ile Gly Asp Asp Ser
    290                 295                 300

His Ser Leu Pro Cys Pro Leu Ala Leu Tyr Thr Ile Asn Asn Gly Ala
305                 310                 315                 320

Ala Arg Tyr Ser Glu Pro Leu Gln Val Ser Ile Ser
                325                 330
```

-continued

```
<210> SEQ ID NO 54
<211> LENGTH: 246
<212> TYPE: PRT
<213> ORGANISM: Artificial Sequence
<220> FEATURE:
<223> OTHER INFORMATION: Synthetic peptide ULBP-6 (ACCESSION NO
      NP_570970)

<400> SEQUENCE: 54

Met Ala Ala Ala Ile Pro Ala Leu Leu Leu Cys Leu Pro Leu Leu
1               5                   10                  15

Phe Leu Leu Phe Gly Trp Ser Arg Ala Arg Arg Asp Asp Pro His Ser
                20                  25                  30

Leu Cys Tyr Asp Ile Thr Val Ile Pro Lys Phe Arg Pro Gly Pro Arg
            35                  40                  45

Trp Cys Ala Val Gln Gly Gln Val Asp Glu Lys Thr Phe Leu His Tyr
        50                  55                  60

Asp Cys Gly Asn Lys Thr Val Thr Pro Val Ser Pro Leu Gly Lys Lys
65                  70                  75                  80

Leu Asn Val Thr Met Ala Trp Lys Ala Gln Asn Pro Val Leu Arg Glu
                85                  90                  95

Val Val Asp Ile Leu Thr Glu Gln Leu Leu Asp Ile Gln Leu Glu Asn
                100                 105                 110

Tyr Thr Pro Lys Glu Pro Leu Thr Leu Gln Ala Arg Met Ser Cys Glu
            115                 120                 125

Gln Lys Ala Glu Gly His Ser Ser Gly Ser Trp Gln Phe Ser Ile Asp
        130                 135                 140

Gly Gln Thr Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Asp Val Ala Met Ser Phe His Tyr Ile Ser Met Gly Asp Cys Ile Gly
                180                 185                 190

Trp Leu Glu Asp Phe Leu Met Gly Met Asp Ser Thr Leu Glu Pro Ser
            195                 200                 205

Ala Gly Ala Pro Leu Ala Met Ser Ser Gly Thr Thr Gln Leu Arg Ala
        210                 215                 220

Thr Ala Thr Thr Leu Ile Leu Cys Cys Leu Leu Ile Ile Leu Pro Cys
225                 230                 235                 240

Phe Ile Leu Pro Gly Ile
                245

<210> SEQ ID NO 55
<211> LENGTH: 182
<212> TYPE: PRT
<213> ORGANISM: Artificial Sequence
<220> FEATURE:
<223> OTHER INFORMATION: Synthetic peptide MICwed alpha1-alpha2

<400> SEQUENCE: 55

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45
```

Trp Ala Glu Asp Val Leu Gly Asn Lys Thr Trp Asp Arg Glu Thr Arg
                50                  55                  60

Asp Leu Thr Gly Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Lys Glu Trp Thr
                115                 120                 125

Met Pro Gln Ser Ser Arg Ala Gln Thr Leu Ala Met Asn Val Arg Asn
        130                 135                 140

Phe Leu Lys Glu Asp Ala Met Glu Thr Asp Thr His Tyr His Ala Met
145                 150                 155                 160

His Ala Asp Cys Leu Gln Glu Leu Arg Tyr Leu Lys Ser Gly Val
                165                 170                 175

Val Leu Arg Arg Thr Val
        180

<210> SEQ ID NO 56
<211> LENGTH: 182
<212> TYPE: PRT
<213> ORGANISM: Artificial Sequence
<220> FEATURE:
<223> OTHER INFORMATION: Synthetic peptide DSM20 alpha1-alpha2

<400> SEQUENCE: 56

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
 50                  55                  60

Asp Leu Thr Ala Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Leu Glu Trp Thr
                115                 120                 125

Met Pro Gln Ser Ser Arg Ala Gln Thr Leu Ala Met Asn Val Arg Asn
        130                 135                 140

Phe Leu Lys Glu Asp Ala Met Gln Thr Asp Thr His Tyr Arg Ala Met
145                 150                 155                 160

His Ala Asp Cys Leu Phe Glu Leu Arg Tyr Leu Lys Ser Gly Val
                165                 170                 175

Val Leu Arg Arg Thr Val
        180

<210> SEQ ID NO 57
<211> LENGTH: 182
<212> TYPE: PRT
<213> ORGANISM: Artificial Sequence
<220> FEATURE:

<223> OTHER INFORMATION: Synthetic peptide DSM25 alpha1-alpha2

<400> SEQUENCE: 57

```
Glu Pro His Ser Leu Arg Tyr Asn Leu Thr Val Leu Ser Trp Asp Gly
1               5                   10                  15
Ser Val Gln Ser Gly Phe Leu Thr Glu Val His Leu Asp Gly Gln Pro
            20                  25                  30
Phe Leu Arg Cys Asp Arg Gln Lys Cys Arg Ala Lys Pro Gln Gly Gln
        35                  40                  45
Trp Ala Glu Asp Val Leu Gly Asn Lys Thr Trp Asp Arg Glu Thr Arg
    50                  55                  60
Asp Leu Thr Gly Trp Gly Lys Asp Leu Arg Met Thr Leu Ala His Ile
65                  70                  75                  80
Lys Asp Gln Lys Glu Gly Leu His Ser Leu Gln Glu Ile Arg Val Cys
                85                  90                  95
Glu Ile His Glu Asp Asn Ser Thr Arg Ser Ser Gln His Phe Tyr Tyr
            100                 105                 110
Asp Gly Glu Leu Phe Leu Ser Gln Asn Leu Glu Thr Leu Glu Trp Thr
        115                 120                 125
Met Pro Gln Ser Ser Arg Ala Gln Thr Leu Ala Met Asn Val Arg Asn
    130                 135                 140
Phe Leu Lys Glu Asp Ala Met Glu Thr Asp Thr His Tyr His Ala Met
145                 150                 155                 160
Arg Ala Asp Cys Leu Ser Glu Leu Arg Arg Tyr Leu Lys Ser Gly Val
                165                 170                 175
Val Leu Arg Arg Thr Val
            180
```

<210> SEQ ID NO 58
<211> LENGTH: 182
<212> TYPE: PRT
<213> ORGANISM: Artificial Sequence
<220> FEATURE:
<223> OTHER INFORMATION: Synthetic peptide DSM27 alpha1-alpha2

<400> SEQUENCE: 58

```
Glu Pro His Ser Leu Arg Tyr Asn Leu Thr Val Leu Ser Trp Asp Gly
1               5                   10                  15
Ser Val Gln Ser Gly Phe Leu Thr Glu Val His Leu Asp Gly Gln Pro
            20                  25                  30
Phe Leu Arg Cys Asp Arg Gln Lys Cys Arg Ala Lys Pro Gln Gly Gln
        35                  40                  45
Trp Ala Glu Asp Val Leu Gly Asn Lys Thr Trp Asp Arg Glu Thr Arg
    50                  55                  60
Asp Leu Thr Gly Trp Gly Lys Asp Leu Arg Met Thr Leu Ala His Ile
65                  70                  75                  80
Lys Asp Gln Lys Glu Gly Leu His Ser Leu Gln Glu Ile Arg Val Cys
                85                  90                  95
Glu Ile His Glu Asp Asn Ser Thr Arg Ser Ser Gln His Phe Tyr Tyr
            100                 105                 110
Asp Gly Glu Leu Phe Leu Ser Gln Asn Leu Glu Thr Leu Glu Trp Thr
        115                 120                 125
Met Pro Gln Ser Ser Arg Ala Gln Thr Leu Ala Met Asn Val Arg Asn
    130                 135                 140
Phe Leu Lys Glu Asp Ala Met Lys Thr Lys Thr His Tyr His Ala Met
145                 150                 155                 160
```

```
Arg Ala Asp Cys Leu Ser Glu Leu Arg Arg Tyr Leu Lys Ser Gly Val
                165                 170                 175

Val Leu Arg Arg Thr Val
            180

<210> SEQ ID NO 59
<211> LENGTH: 182
<212> TYPE: PRT
<213> ORGANISM: Artificial Sequence
<220> FEATURE:
<223> OTHER INFORMATION: Synthetic peptide DSM28 alpha1-alpha2

<400> SEQUENCE: 59

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val
            180

<210> SEQ ID NO 60
<211> LENGTH: 182
<212> TYPE: PRT
<213> ORGANISM: Artificial Sequence
<220> FEATURE:
<223> OTHER INFORMATION: Synthetic peptide DSM42 alpha1-alpha2

<400> SEQUENCE: 60

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
```

```
                    85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Leu Glu Trp Thr
            115                 120                 125

Met Pro Gln Ser Ser Arg Ala Gln Thr Leu Ala Met Asn Val Arg Asn
        130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val
            180

<210> SEQ ID NO 61
<211> LENGTH: 182
<212> TYPE: PRT
<213> ORGANISM: Artificial Sequence
<220> FEATURE:
<223> OTHER INFORMATION: Synthetic peptide DSM48 alpha1-alpha2

<400> SEQUENCE: 61

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Leu Glu Trp Thr
            115                 120                 125

Met Pro Gln Ser Ser Arg Ala Gln Thr Leu Ala Met Asn Val Arg Asn
        130                 135                 140

Phe Leu Lys Glu Asp Ala Met Ala Thr Asp Thr His Tyr Ile Ala Met
145                 150                 155                 160

Arg Ala Asp Cys Leu Ala Glu Leu Arg Arg Tyr Leu Lys Ser Gly Val
                165                 170                 175

Val Leu Arg Arg Thr Val
            180

<210> SEQ ID NO 62
<211> LENGTH: 182
<212> TYPE: PRT
<213> ORGANISM: Artificial Sequence
<220> FEATURE:
<223> OTHER INFORMATION: Synthetic peptide DSM49 alpha1-alpha2

<400> SEQUENCE: 62

Glu Pro His Ser Leu Arg Tyr Asn Leu Thr Val Leu Ser Trp Asp Gly
1               5                   10                  15
```

```
Ser Val Gln Thr Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gln Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Phe Thr Asp Thr His Tyr Arg Ala Met
145                 150                 155                 160

Thr Ala Asp Cys Leu Thr Glu Leu Arg Arg Tyr Leu Lys Ser Gly Val
                165                 170                 175

Val Leu Arg Arg Thr Val
            180

<210> SEQ ID NO 63
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 63
atctataatg ctgagcccca cagtcttcg                                    29

<210> SEQ ID NO 64
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 64
cttgctcttc agatatcgcc gtagttc                                      27

<210> SEQ ID NO 65
<211> LENGTH: 7556
<212> TYPE: DNA
<213> ORGANISM: Artificial Sequence
<220> FEATURE:
<223> OTHER INFORMATION: Synthetic DNA construct expressing wt a1a2
      domain-Fv

<400> SEQUENCE: 65
ggagagacca cacccaagct gtctagagcc gccacgatgg ggctgggccc ggtcttcctg    60
cttctggctg gcatcttccc ttttgcacct ccgggagctg ctgctgagcc cacagtctt   120 cgttataacc tcacggtgct gtcctgggat ggatctgtgc agtcagggtt tctcactgag   180
gtacatctgg atggtcagcc cttcctgcgc tgtgacaggc agaaatgcag ggcaaagccc   240
cagggacagt gggcagaaga tgtcctggga aataagacat gggacagaga gaccagagac   300
ttgacaggga atggaaagga cctcaggatg accctggctc atatcaagga ccagaaagaa   360
```

```
ggcttgcatt ccctccagga gattagggtc tgtgagatcc atgaagacaa cagcaccagg    420
agctcccagc atttctacta cgatggggag ctctttctct cccaaaacct ggagactaag    480
gaatggacaa tgccccagtc ctccagagct cagaccttgg ccatgaacgt caggaatttc    540
ttgaaggaag atgcaatgaa gaccaagaca cactatcacg ctatgcatgc agactgcctg    600
caggaactac ggcgatatct aaaatccggc gtagtcctga ggagaacagt gccccccatg    660
gtgcaggtga ctcgctctga ggcctctggc ggatctgggg accgtgtgac aatcacctgc    720
agagcctccc aggacgtctc cactgccgtg gcgtggtacc aacagaagcc cgggaaggca    780
cccaaactgc tcatttacag cgcatccttt ctctactctg gcgtgccgtc tcgctttagc    840
gggtccggca gcggtacaga ctttactctg accatctcct ctctgcaacc ggaggatttt    900
gcaacctatt attgccagca atcctacaca accccccccca cctttggcca gggcaccaag    960
gtggagatca agggaggttc tagccgctcc agcagctctg gaggtggagg ctctggcgga   1020
ggaggcgagt gcaactggt ggagtctggg ggcggcctgg tccagcccgg cggaagcttg   1080
cgcctgagct gtgccgcctc cggttttacc ttcaccagca ctggaatctc ctgggtgcgc   1140
caagctcccg gcaaagggct cgaatgggtg gccgtatct accccaccaa cggaagcacc    1200
aactatgcag acagcgtgaa ggggcgcttc actatctccg ccgacaccag caaaaacacc   1260
gcgtacctgc agatgaattc tttgagggca gaggatactg ccgtgtacta ctgcgcgagg   1320
acatacggca tttacgatct gtatgtggat tacaccgaat acgtgatgga ctattgggc   1380 cagggcactc tggtcacagt gtctagcggt ggcagctccc gcagctccag cagcggtggt   1440
ggcggtagcg gaggcggagg cgatatccag atgactcaga gtccctcttc tctgagtgct   1500 tctgcggaa gtgggcagat caccgtcaca tgtcgcgcaa gcggcttta tccttggaac   1560 atcaccctga gctggcggca ggacggcgtc agcctgtccc atgatcccca acagtgggga   1620
gatgtgctcc cggacggtca gggaacttac cagacctggg ttgcaactcg catctcccag   1680
ggggaggagc agcgtttcac atgttatatg gagcactctg gccagcacag cactcatccg   1740
gtgccgtccg gaaagggatc tcatcaccat caccaccact aggatccgtt gaggtctcta   1800
aaagcgtctt cctgttctca tcacatcata tcaaggttat ataccatcaa tattgccaca   1860
gatgttactt agccttttaa tatttctcta atttagtgta tatgcaatga tagttctctg   1920
atttctgaga ttgagttcct catgtgtaat gattatttag agtttctctt tcatctgttc   1980
aaatttttgt ctagttttat tttttactga tttgtaagac ttcttttat aatctgcata   2040 ttacaattct ctttactggg gtgttgcaaa tatttctgt cattctatgg cctgactttt   2100
cttaatggtt ttttaatttt aaaaataagt cttaatattc atgcaatcta attaacaatc   2160
ttttctttgt ggttaggact ttgagtcata agaaattttt ctctacactg aagtcatgat   2220
ggcatgcttc tatattattt tctaaaagat ttaaagttttt gccttctcca tttagactta   2280
taattcactg gaatttttt gtgtgtatgg tatgacatat gggttcccctt ttattttta   2340 catataaata tatttccctg ttttttctaaa aaagaaaaag atcatcattt tcccattgta   2400
aaatgccata tttttttcat aggtcactta catatatcaa tgggtctgtt tctgagctct   2460
actctatttt atcagcctca ctgtctatcc ccacacatct catgctttgc tctaaatctt   2520
gatatttagt ggaacattct ttcccatttt gttctacaag aatattttg ttattgtctt   2580 tgggctttct atatacattt tgaaatgagg ttgacaagtt aataatcaac ctctggatta   2640
caaaatttgt gaaagattga ctggtattct taactatgtt gctcctttta cgctatgtgg   2700
```

```
atacgctgct ttaatgcctt tgtatcatgc tattgcttcc cgtatggctt tcattttctc    2760
ctccttgtat aaatcctggt tgctgtctct ttatgaggag ttgtggcccg ttgtcaggca    2820
acgtggcgtg gtgtgcactg tgtttgctga cgcaacccccc actggttggg gcattgccac   2880
cacctgtcag ctcctttccg ggactttcgc tttccccctc cctattgcca cggcggaact    2940
catcgccgcc tgccttgccc gctgctggac aggggctcgg ctgttgggca ctgacaattc    3000
cgtggtgttg tcggggaaat catcgtcctt tccttggctg ctcgcctgtg ttgccacctg    3060
gattctgcgc gggacgtcct tctgctacgt cccttcggcc ctcaatccag cggaccttcc    3120
ttcccgcggc ctgctgccgg ctctgcggcc tcttccgcct cttcgccttc gccctcagac    3180
gagtcggatc tcccttgggg ccgcctcccc gcatctgtgc cttctagttg ccagccatct    3240
gttgtttgcc cctcccccgt gccttccttg accctggaag gtgccactcc cactgtcctt    3300
tcctaataaa atgaggaaat tgcatcgcat tgtctgagta ggtgtcattc tattctgggg    3360
ggtggggtgg ggcaggacag caaggggggag gattggcaag acaatagcag gctttgcatt   3420
tttagacatt tagaagccta tatcttgtta cagaattgga attacacaaa aattctacca    3480
tatttgaaa gcttaggttg ttctgaaaaa aacaatatat tgttttcctg ggtaaactaa    3540
aagtcccctc gaggaaaggc ccctaaagtg aaacagtgca aaacgttcaa aaactgtctg    3600
gcaatacaag ttccactttg accaaaacgg ctggcagtaa aagggttaag aagactgtca    3660
gccttgagcg gtatcagctc actcaaaggc ggtaatacgg ttatccacag aatcagggga    3720
taacgcagga agaacatgt gagcaaaagg ccagcaaaag gccaggaacc gtaaaaaggc     3780
cgcgttgctg gcgttttttcc ataggctccg ccccccctgac gagcatcaca aaaatcgacg   3840
ctcaagtcag aggtggcgaa acccgacagg actataaaga taccaggcgt ttccccctgg    3900
aagctccctc gtgcgctctc ctgttccgac cctgccgctt accggatacc tgtccgcctt    3960
tctcccttcg ggaagcgtgg cgctttctca tagctcacgc tgtaggtatc tcagttcggt    4020
gtaggtcgtt cgctccaagc tgggctgtgt gcacgaaccc cccgttcagc ccgaccgctg    4080
cgccttatcc ggtaactatc gtcttgagtc caacccggta agacacgact tatcgccact    4140
ggcagcagcc actggtaaca ggattagcag agcgaggtat gtaggcggtg ctacagagtt    4200
cttgaagtgg tgggctaact acggctacac tagaagaaca gtatttggta tctgcgctct    4260
gctgaagcca gttaccttcg gaaaaagagt tggtagctct tgatccggca aacaaaccac    4320
cgctggtagc ggtggttttt tgtttgcaa gcagcagatt acgcgcagaa aaaaaggatc     4380
tcaagaagat cctttgatct tttctacggg gtctgacgct cagtggaacg acgcgcgcgt    4440
aactcacgtt aagggatttt ggtcatgagt tagaaaaact catcgagcat caaatgaaac    4500
tgcaatttat tcatatcagg attatcaata ccatattttt gaaaaagccg tttctgtaat    4560
gaaggagaaa actcaccgag gcagttccat aggatggcaa gatcctggta tcggtctgcg    4620
attccgactc gtccaacatc aatacaacct attaatttcc cctcgtcaaa ataaggttta    4680
tcaagtgaga aatcaccatg agtgacgact gaatccggtg agaatggcaa aagtttatgc    4740
atttctttcc agacttgttc aacaggccag ccattacgct cgtcatcaaa atcactcgca    4800
tcaaccaaac cgttattcat tcgtgattgc gcctgagcga ggcgaaatac gcgatcgctg    4860
ttaaaaggac aattacaaac aggaatcgag tgcaaccggc gcaggaacac tgccagcgca    4920
tcaacaatat tttcacctga atcaggatat tcttctaata cctggaacgc tgttttttccg   4980
gggatcgcag tggtgagtaa ccatgcatca tcaggagtac ggataaaatg cttgatggtc    5040
ggaagtggca taaattccgt cagccagttt agtctgacca tctcatctgt aacatcattg    5100
```

```
gcaacgctac ctttgccatg tttcagaaac aactctggcg catcgggctt cccatacaag   5160
cgatagattg tcgcacctga ttgcccgaca ttatcgcgag cccatttata cccatataaa   5220
tcagcatcca tgttggaatt taatcgcggc ctcgacgttt cccgttggat atggctcatt   5280
ttttacttcc tcaccttgtc gtattatact atgccgatat actatgccga tgattaattg   5340
tcgacactgc gggggctctg tgtggtaagc aggtcttaac cttttactg ccaatgacgc    5400 atgggatacg tcgtggcagt aaaagggctt aaatgccaac gacgcgtccc atacgttgtt   5460
ggcattttaa ttcttctctc tgcagcggca gcatgtgccg ccgctgcaga gagtttctag   5520
cgatgacagc ccctctgggc aacgagccgg ggggctgtc tttctttatg ttttaaatgc    5580
actgacctcc cacattccct ttttagtaaa atattcagaa ataatttaaa tacatcattg   5640
caatgaaaat aaatgttttt tattaggcag aatccagatg ctcaaggccc ttcataatat   5700
cccccagttt agtagttgga cttagggaac aaaggaacct ttaatagaaa ttggacagca   5760
agaaagcgag tcaggcaccg ggcttgcggg tcatgcacca ggtgcgcggt ccttcgggca   5820
cctcgacgtc ggcggtgacg gtgaagccga ccgctcgta aaggggagg ttgcggggcg     5880 cggatgtctc caggaaggcg ggcaccccgg cgcgctcggc cgcctccact ccggggagca   5940
cgacggcgct gcccagaccc ttgccctggt ggtcgggcga cacgccgacg gtggccagga   6000
accacgcggg ctccttgggc cggtgcggcg ccaggaggcc ttccatctgt tgctgcgcgg   6060
ccagccggga accgctcaac tcggccatgc gcgggccgat ctcggcgaac accgccccg    6120 cttcgacgct ctccggcgtg gtccagaccg ccaccgcggc gccgtcgtcc gcgacccaca   6180
ccttgccgat gtcgagcccg acgcgcgtga ggaagagttc ttgcagctcg gtgacccgct   6240
cgatgtggcg gtccggatcg acggtgtggc gcgtggcggg gtagtcggcg aacgcggcgg   6300
cgagggtgcg tacggccctg gggacgtcgt cgcgggtggc gaggcgcacc gtgggcttgt   6360
actcggtcat ggtggcggac gaaaggcccg gagatgagga agaggagaac agcgcggcag   6420
acgtgcgctt ttgaagcgtg cagaatgccg ggcctccgga ggaccttcgg gcgcccgccc   6480 cgccctgag cccgcccctg agcccgcccc cggaccacc ccttcccagc ctctgagccc     6540
agaaagcgaa ggagcaaagc tgctattggc cgctgcccca aaggcctacc cgcttccatt   6600
gctcagcggt gctgtccatc tgcacgagac tagtgagtcg tgctacttcc atttgtcacg   6660
tcctgcacga cgcgagctgc ggggcggggg ggaacttcct gactagggga ggagtagaag   6720
gtggcgcgaa ggggccacca aagaacggag ccggttggcg cctaccggtg gatgtggaat   6780
gtgtgcgagg ccagaggcca cttgtgtagc gccaagtgcc cagcggggct gctaaagcgc   6840
atgctccaga ctgccttggg aaaagcgcct cccctacccg gtagagaaac ttgatctgtc   6900
gccgcaattc aaacttcgtg aggctccggt gccgtcagt gacctgctat actctggaga    6960
cgacttacgg taaatggccc gcctggctga ccgcccaacg accccgccc attgacgtca    7020 ataatgacgt atgttcccat agtaacgcca tagggactt tccattgacg tcaatggtg     7080 gagtatttac ggtaaactgc ccacttggca gtacatcaag tgtatcatat gccaagtccg   7140 cccctattg acgtcaatga cggtaaatgg cccgcctggc attatgccca gtacatgacc    7200
ttacgggact ttcctacttg gcagtacatc tacgtattag tcatcgctat taccatgctg   7260
atgcggtttt ggcagtacac caatgggcgt ggatagcggt ttgactcacg ggatttcca    7320 agtctccacc ccattgacgt caatgggagt tgttttggc accaaaatca acgggacttt    7380
ccaaaatgtc gtaataaccc cgccccgttg acgcaaatgg gcggtaggcg tgtacggtgg   7440
```

```
gaggtctata taagcagagc tcgtttagtg aaccgtcaga tcgcctggag aggccatcca    7500
cgctgttttg acctccatag tggacaccgg gaccgatcca gcctccgcgt ctcagg       7556
```

<210> SEQ ID NO 66
<211> LENGTH: 558
<212> TYPE: PRT
<213> ORGANISM: Artificial Sequence
<220> FEATURE:
<223> OTHER INFORMATION: Synthetic peptide wt MICA-Fv

<400> SEQUENCE: 66

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
    290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350
```

```
Glu Trp Val Gly Arg Ile Tyr Pro Thr Asn Gly Ser Thr Asn Tyr Ala
            355                 360                 365

Asp Ser Val Lys Gly Arg Phe Thr Ile Ser Ala Asp Thr Ser Lys Asn
        370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Ser
        435                 440                 445

Gly Gly Gly Gly Asp Ile Gln Met Thr Gln Ser Pro Ser Ser Leu Ser
        450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
        530                 535                 540

Pro Val Pro Ser Gly Lys Gly Ser His His His His His
545                 550                 555

<210> SEQ ID NO 67
<211> LENGTH: 558
<212> TYPE: PRT
<213> ORGANISM: Artificial Sequence
<220> FEATURE:
<223> OTHER INFORMATION: Synthetic peptide MICwed-Fv

<400> SEQUENCE: 67

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160
```

His Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
    290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
        435                 440                 445

Gly Gly Gly Gly Asp Ile Gln Met Thr Gln Ser Pro Ser Ser Leu Ser
    450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
    530                 535                 540

Pro Val Pro Ser Gly Lys Gly Ser His His His His His
545                 550                 555

<210> SEQ ID NO 68
<211> LENGTH: 558

<212> TYPE: PRT
<213> ORGANISM: Artificial Sequence
<220> FEATURE:
<223> OTHER INFORMATION: Synthetic peptide MICv20-Fv

<400> SEQUENCE: 68

```
Glu Pro His Ser Leu Arg Tyr Asn Leu Thr Val Leu Ser Trp Asp Gly
 1               5                  10                  15
Ser Val Gln Ser Gly Phe Leu Thr Glu Val His Leu Asp Gly Gln Pro
            20                  25                  30
Phe Leu Arg Cys Asp Arg Gln Lys Cys Arg Ala Lys Pro Gln Gly Gln
        35                  40                  45
Trp Ala Glu Asp Val Leu Gly Asn Lys Thr Trp Asp Arg Glu Th

```
Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
        435                 440                 445

Gly Gly Gly Asp Ile Gln Met Thr Gln Ser Pro Ser Ser Leu Ser
    450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gly Glu Glu
            515                 520                 525

Gln Arg Phe Thr Cys Tyr Met Glu His Ser Gly Gln His Ser Thr His
530                 535                 540

Pro Val Pro Ser Gly Lys Gly Ser His His His His His His
545                 550                 555

<210> SEQ ID NO 69
<211> LENGTH: 558
<212> TYPE: PRT
<213> ORGANISM: Artificial Sequence
<220> FEATURE:
<223> OTHER INFORMATION: Synthetic peptide MICv25-Fv

<400> SEQUENCE: 69

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190
```

Ala Ser Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
        260                 265                 270

Ser Tyr Thr Thr Pro Pro Thr Phe Gly Gln Gly Thr Lys Val Glu Ile
    275                 280                 285

Lys Gly Gly Ser Ser Arg Ser Ser Ser Gly Gly Gly Gly Ser Gly
        290                 295                 300

Gly Gly Gly Glu Val Gln Leu Val Glu Ser Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
        340                 345                 350

Glu Trp Val Gly Arg Ile Tyr Pro Thr Asn Gly Ser Thr Asn Tyr Ala
    355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
        420                 425                 430

Ser Ser Gly Gly Ser Ser Arg Ser Ser Ser Gly Gly Gly Gly Ser
    435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
        500                 505                 510

Gly Thr Tyr Gln Thr Trp Val Ala Thr Arg Ile Ser Gln Gly Glu Glu
    515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555

<210> SEQ ID NO 70
<211> LENGTH: 558
<212> TYPE: PRT
<213> ORGANISM: Artificial Sequence
<220> FEATURE:
<223> OTHER INFORMATION: Synthetic peptide MICv27-Fv

<400> SEQUENCE: 70

-continued

```
Glu Pro His Ser Leu Arg Tyr Asn Leu Thr Val Leu Ser Trp Asp Gly
 1               5                  10                  15

Ser Val Gln Ser Gly Phe Leu Thr Glu Val His Leu Asp Gly Gln Pro
             20                  25                  30

Phe Leu Arg Cys Asp Arg Gln Lys Cys Arg Ala Lys Pro Gln Gly Gln
         35                  40                  45

Trp Ala Glu Asp Val Leu Gly Asn Lys Thr Trp Asp Arg Glu Thr Arg
 50                  55                  60

Asp Leu Thr Gly Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Leu Glu Trp Thr
            115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val Pro Pro Met Val Gln Val Thr Arg Ser Glu
                180                 185                 190

Ala Ser Gly Gly Ser Gly Asp Arg Val Thr Ile Thr Cys Arg Ala Ser
            195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
                260                 265                 270

Ser Tyr Thr Thr Pro Pro Thr Phe Gly Gln Gly Thr Lys Val Glu Ile
            275                 280                 285

Lys Gly Gly Ser Ser Arg Ser Ser Ser Ser Gly Gly Gly Gly Ser Gly
    290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
                340                 345                 350

Glu Trp Val Gly Arg Ile Tyr Pro Thr Asn Gly Ser Thr Asn Tyr Ala
            355                 360                 365

Asp Ser Val Lys Gly Arg Phe Thr Ile Ser Ala Asp Thr Ser Lys Asn
    370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
```

-continued

```
                420               425               430
Ser Ser Gly Gly Ser Ser Arg Ser Ser Ser Gly Gly Gly Ser
            435               440               445

Gly Gly Gly Gly Asp Ile Gln Met Thr Gln Ser Pro Ser Leu Ser
            450               455               460

Ala Ser Gly Gly Ser Gly Gln Ile Thr Val Thr Cys Arg Ala Ser Gly
465               470               475               480

Phe Tyr Pro Trp Asn Ile Thr Leu Ser Trp Arg Gln Asp Gly Val Ser
                485               490               495

Leu Ser His Asp Thr Gln Gln Trp Gly Asp Val Leu Pro Asp Gly Gln
                500               505               510

Gly Thr Tyr Gln Thr Trp Val Ala Thr Arg Ile Ser Gln Gly Glu Glu
            515               520               525

Gln Arg Phe Thr Cys Tyr Met Glu His Ser Gly Gln His Ser Thr His
            530               535               540

Pro Val Pro Ser Gly Lys Gly Ser His His His His His His
545               550               555
```

<210> SEQ ID NO 71
<211> LENGTH: 558
<212> TYPE: PRT
<213> ORGANISM: Artificial Sequence
<220> FEATURE:
<223> OTHER INFORMATION: Synthetic peptide MICv28-Fv

<400> SEQUENCE: 71

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
50              55                  60

Asp Leu Thr Gly Asn Gly Lys Asp Leu Arg Met Thr Leu Ala His Ile
65              70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
            115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
            195                 200                 205

Gln Asp Val Ser Thr Ala Val Ala Trp Tyr Gln Gln Lys Pro Gly Lys
210                 215                 220

Ala Pro Lys Leu Leu Ile Tyr Ser Ala Ser Phe Leu Tyr Ser Gly Val
```

```
            225                 230                 235                 240
Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
                260                 265                 270

Ser Tyr Thr Thr Pro Pro Thr Phe Gly Gln Gly Thr Lys Val Glu Ile
                275                 280                 285

Lys Gly Gly Ser Ser Arg Ser Ser Ser Gly Gly Gly Gly Ser Gly
                290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
                340                 345                 350

Glu Trp Val Gly Arg Ile Tyr Pro Thr Asn Gly Ser Thr Asn Tyr Ala
                355                 360                 365

Asp Ser Val Lys Gly Arg Phe Thr Ile Ser Ala Asp Thr Ser Lys Asn
                370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
                420                 425                 430

Ser Ser Gly Gly Ser Ser Arg Ser Ser Ser Gly Gly Gly Gly Ser
                435                 440                 445

Gly Gly Gly Gly Asp Ile Gln Met Thr Gln Ser Pro Ser Ser Leu Ser
                450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
                515                 520                 525

Gln Arg Phe Thr Cys Tyr Met Glu His Ser Gly Gln His Ser Thr His
                530                 535                 540

Pro Val Pro Ser Gly Lys Gly Ser His His His His His
545                 550                 555

<210> SEQ ID NO 72
<211> LENGTH: 558
<212> TYPE: PRT
<213> ORGANISM: Artificial Sequence
<220> FEATURE:
<223> OTHER INFORMATION: Synthetic peptide MICv42-Fv

<400> SEQUENCE: 72

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
```

-continued

```
            35                  40                  45
Trp Ala Glu Asp Val Leu Gly Asn Lys Thr Trp Asp Arg Glu Thr Arg
 50                  55                  60
Asp Leu Thr Gly Trp Gly Lys Asp Leu Arg Met Thr Leu Ala His Ile
 65                  70                  75                  80
Lys Asp Gln Lys Glu Gly Leu His Ser Leu Gln Glu Ile Arg Val Cys
                 85                  90                  95
Glu Ile His Glu Asp Asn Ser Thr Arg Ser Ser Gln His Phe Tyr Tyr
                100                 105                 110
Asp Gly Glu Leu Phe Leu Ser Gln Asn Leu Glu Thr Leu Glu Trp Thr
            115                 120                 125
Met Pro Gln Ser Ser Arg Ala Gln Thr Leu Ala Met Asn Val Arg Asn
        130                 135                 140
Phe Leu Lys Glu Asp Ala Met Glu Thr Asp Thr His Tyr His Ala Met
145                 150                 155                 160
Arg Ala Asp Cys Leu Gln Glu Leu Arg Arg Tyr Leu Lys Ser Gly Val
                165                 170                 175
Val Leu Arg Arg Thr Val Pro Pro Met Val Gln Val Thr Arg Ser Glu
            180                 185                 190
Ala Ser Gly Gly Ser Gly Asp Arg Val Thr Ile Thr Cys Arg Ala Ser
        195                 200                 205
Gln Asp Val Ser Thr Ala Val Ala Trp Tyr Gln Gln Lys Pro Gly Lys
210                 215                 220
Ala Pro Lys Leu Leu Ile Tyr Ser Ala Ser Phe Leu Tyr Ser Gly Val
225                 230                 235                 240
Pro Ser Arg Phe Ser Gly Ser Gly Ser Gly Thr Asp Phe Thr Leu Thr
                245                 250                 255
Ile Ser Ser Leu Gln Pro Glu Asp Phe Ala Thr Tyr Tyr Cys Gln Gln
            260                 265                 270
Ser Tyr Thr Thr Pro Pro Thr Phe Gly Gln Gly Thr Lys Val Glu Ile
        275                 280                 285
Lys Gly Gly Ser Ser Arg Ser Ser Ser Gly Gly Gly Gly Ser Gly
    290                 295                 300
Gly Gly Gly Glu Val Gln Leu Val Glu Ser Gly Gly Gly Leu Val Gln
305                 310                 315                 320
Pro Gly Gly Ser Leu Arg Leu Ser Cys Ala Ala Ser Gly Phe Thr Phe
                325                 330                 335
Thr Ser Thr Gly Ile Ser Trp Val Arg Gln Ala Pro Gly Lys Gly Leu
            340                 345                 350
Glu Trp Val Gly Arg Ile Tyr Pro Thr Asn Gly Ser Thr Asn Tyr Ala
        355                 360                 365
Asp Ser Val Lys Gly Arg Phe Thr Ile Ser Ala Asp Thr Ser Lys Asn
370                 375                 380
Thr Ala Tyr Leu Gln Met Asn Ser Leu Arg Ala Glu Asp Thr Ala Val
385                 390                 395                 400
Tyr Tyr Cys Ala Arg Thr Tyr Gly Ile Tyr Asp Leu Tyr Val Asp Tyr
                405                 410                 415
Thr Glu Tyr Val Met Asp Tyr Trp Gly Gln Gly Thr Leu Val Thr Val
            420                 425                 430
Ser Ser Gly Gly Ser Ser Arg Ser Ser Ser Gly Gly Gly Gly Ser
        435                 440                 445
Gly Gly Gly Gly Asp Ile Gln Met Thr Gln Ser Pro Ser Ser Leu Ser
    450                 455                 460
```

```
Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555
```

<210> SEQ ID NO 73
<211> LENGTH: 558
<212> TYPE: PRT
<213> ORGANISM: Artificial Sequence
<220> FEATURE:
<223> OTHER INFORMATION: Synthetic peptide MICv48-Fc

<400> SEQUENCE: 73

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Ala Thr Asp Thr His Tyr Ile Ala Met
145                 150                 155                 160

Arg Ala Asp Cys Leu Ala Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270
```

Ser Tyr Thr Thr Pro Pro Thr Phe Gly Gln Gly Thr Lys Val Glu Ile
            275                 280                 285

Lys Gly Gly Ser Ser Arg Ser Ser Ser Gly Gly Gly Ser Gly
        290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
        435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
        530                 535                 540

Pro Val Pro Ser Gly Lys Gly Ser His His His His His
545                 550                 555

<210> SEQ ID NO 74
<211> LENGTH: 558
<212> TYPE: PRT
<213> ORGANISM: Artificial Sequence
<220> FEATURE:
<223> OTHER INFORMATION: Synthetic peptide MICv49-Fv

<400> SEQUENCE: 74

Glu Pro His Ser Leu Arg Tyr Asn Leu Thr Val Leu Ser Trp Asp Gly
1               5                   10                  15

Ser Val Gln Thr Gly Phe Leu Thr Glu Val His Leu Asp Gly Gln Pro
            20                  25                  30

```
Lys Asp Gln Lys Glu Gly Leu His Ser Leu Gln Ile Arg Val Cys
                85                  90                  95
Glu Ile His Glu Asp Asn Ser Thr Arg Ser Ser Gln His Phe Tyr Tyr
            100                 105                 110
Asp Gly Glu Leu Phe Leu Ser Gln Asn Leu Glu Thr Lys Glu Trp Thr
            115                 120                 125
Met Pro Gln Ser Ser Arg Ala Gln Thr Leu Ala Met Asn Val Arg Asn
130                 135                 140
Phe Leu Lys Glu Asp Ala Met Phe Thr Asp Thr His Tyr Arg Ala Met
145                 150                 155                 160
Thr Ala Asp Cys Leu Thr Glu Leu Arg Tyr Leu Lys Ser Gly Val
                165                 170                 175
Val Leu Arg Arg Thr Val Pro Pro Met Val Gln Val Thr Arg Ser Glu
            180                 185                 190
Ala Ser Gly Gly Ser Gly Asp Arg Val Thr Ile Thr Cys Arg Ala Ser
            195                 200                 205
Gln Asp Val Ser Thr Ala Val Ala Trp Tyr Gln Gln Lys Pro Gly Lys
    210                 215                 220
Ala Pro Lys Leu Leu Ile Tyr Ser Ala Ser Phe Leu Tyr Ser Gly Val
225                 230                 235                 240
Pro Ser Arg Phe Ser Gly Ser Gly Ser Gly Thr Asp Phe Thr Leu Thr
                245                 250                 255
Ile Ser Ser Leu Gln Pro Glu Asp Phe Ala Thr Tyr Tyr Cys Gln Gln
                260                 265                 270
Ser Tyr Thr Thr Pro Pro Thr Phe Gly Gln Gly Thr Lys Val Glu Ile
            275                 280                 285
Lys Gly Gly Ser Ser Arg Ser Ser Ser Gly Gly Gly Gly Ser Gly
            290                 295                 300
Gly Gly Gly Glu Val Gln Leu Val Glu Ser Gly Gly Gly Leu Val Gln
305                 310                 315                 320
Pro Gly Gly Ser Leu Arg Leu Ser Cys Ala Ala Ser Gly Phe Thr Phe
                325                 330                 335
Thr Ser Thr Gly Ile Ser Trp Val Arg Gln Ala Pro Gly Lys Gly Leu
            340                 345                 350
Glu Trp Val Gly Arg Ile Tyr Pro Thr Asn Gly Ser Thr Asn Tyr Ala
            355                 360                 365
Asp Ser Val Lys Gly Arg Phe Thr Ile Ser Ala Asp Thr Ser Lys Asn
    370                 375                 380
Thr Ala Tyr Leu Gln Met Asn Ser Leu Arg Ala Glu Asp Thr Ala Val
385                 390                 395                 400
Tyr Tyr Cys Ala Arg Thr Tyr Gly Ile Tyr Asp Leu Tyr Val Asp Tyr
                405                 410                 415
Thr Glu Tyr Val Met Asp Tyr Trp Gly Gln Gly Thr Leu Val Thr Val
            420                 425                 430
Ser Ser Gly Gly Ser Ser Arg Ser Ser Ser Gly Gly Gly Ser
            435                 440                 445
Gly Gly Gly Gly Asp Ile Gln Met Thr Gln Ser Pro Ser Ser Leu Ser
    450                 455                 460
Ala Ser Gly Gly Ser Gly Gln Ile Thr Val Thr Cys Arg Ala Ser Gly
465                 470                 475                 480
Phe Tyr Pro Trp Asn Ile Thr Leu Ser Trp Arg Gln Asp Gly Val Ser
                485                 490                 495
```

```
Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
    530                 535                 540

Pro Val Pro Ser Gly Lys Gly Ser His His His His His
545                 550                 555

<210> SEQ ID NO 75
<211> LENGTH: 137
<212> TYPE: PRT
<213> ORGANISM: Artificial Sequence
<220> FEATURE:
<223> OTHER INFORMATION: Synthetic NKG2D ectodomain

<400> SEQUENCE: 75

Asn Ser Leu Phe Asn Gln Glu Val Gln Ile Pro Leu Thr Glu Ser Tyr
1               5                   10                  15

Cys Gly Pro Cys Pro Lys Asn Trp Ile Cys Tyr Lys Asn Asn Cys Tyr
                20                  25                  30

Gln Phe Phe Asp Glu Ser Lys Asn Trp Tyr Glu Ser Gln Ala Ser Cys
            35                  40                  45

Met Ser Gln Asn Ala Ser Leu Leu Lys Val Tyr Ser Lys Glu Asp Gln
    50                  55                  60

Asp Leu Leu Lys Leu Val Lys Ser Tyr His Trp Met Gly Leu Val His
65                  70                  75                  80

Ile Pro Thr Asn Gly Ser Trp Gln Trp Glu Asp Gly Ser Ile Leu Ser
                85                  90                  95

Pro Asn Leu Leu Thr Ile Ile Glu Met Gln Lys Gly Asp Cys Ala Leu
            100                 105                 110

Tyr Ala Ser Ser Phe Lys Gly Tyr Ile Glu Asn Cys Ser Thr Pro Asn
        115                 120                 125

Thr Tyr Ile Cys Met Gln Arg Thr Val
    130                 135

<210> SEQ ID NO 76
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 76
ctgtctagag ccgccaacat ggggctgggc ccggtcttcc                          40

<210> SEQ ID NO 77
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 77
aacggatcct acacagtcct ttgcatgcag                                     30

<210> SEQ ID NO 78
<211> LENGTH: 6362
<212> TYPE: DNA
<213> ORGANISM: Artificial Sequence
<220> FEATURE:
```

<223> OTHER INFORMATION: Synthetic polynucleotide, pD2509-CMV-Avi-His-
natural NKG2D ectodomain

<400> SEQUENCE: 78

```
ggagagacca cacccaagct gtctagagcc gccaacatgg ggctgggccc ggtcttcctg      60
cttctggctg gcatcttccc ttttgcacct ccgggagctg ctgctgagcc ccaccatcat     120
caccaccatg gccttaacga catcttcgaa gctcaaaaga tcgaatggca tgaaaactca     180
ttattcaacc aagaagttca aattcccttg accgaaagtt actgtggccc atgtcctaaa     240
aactggatat gttacaaaaa taactgctac caattttttg atgagagtaa aaactggtat     300
gagagccagg cttcttgtat gtctcaaaat gccagccttc tgaaagtata cagcaaagag     360
gaccaggatt tacttaaact ggtgaagtca tatcattgga tgggactagt acacattcca     420
acaaatggat cttggcagtg gaagatggcc tccattctct cacccaacct actaacaata     480
attgaaatgc agaagggaga ctgtgcactc tatgcctcga gctttaaagg ctatatagaa     540
aactgttcaa ctccaaatac atacatctgc atgcaaagga ctgtgtagga tccgttgagg     600
tctctaaaag cgtcttcctg ttctcatcac atcatatcaa ggttatatac catcaatatt     660
gccacagatg ttacttagcc ttttaatatt tctctaattt agtgtatatg caatgatagt     720
tctctgattt ctgagattga gtttctcatg tgtaatgatt atttagagtt tctctttcat     780
ctgttcaaat ttttgtctag ttttattttt tactgatttg taagacttct ttttataatc     840
tgcatattac aattctcttt actggggtgt tgcaaatatt ttctgtcatt ctatggcctg     900
actttttctta atggtttttt aattttaaaa ataagtctta atattcatgc aatctaatta     960
acaatctttt ctttgtggtt aggactttga gtcataagaa attttctcct acactgaagt    1020
catgatggca tgcttctata ttattttcta aaagatttaa agttttgcct tctccattta    1080
gacttataat tcactggaat ttttttgtgt gtatggtatg acatatgggt tccctttat    1140
tttttacata taaatatatt tccctgtttt tctaaaaaag aaaaagatca tcatttttccc    1200
attgtaaaat gccatatttt tttcataggt cacttacata tatcaatggg tctgtttctg    1260
agctctactc tattttatca gcctcactgt ctatccccac acatctcatg ctttgctcta    1320
aatcttgata tttagtggaa cattcttttcc cattttgttc tacaagaata ttttttgttat    1380
tgtctttggg ctttctatat acattttgaa atgaggttga caagttaata atcaacctct    1440
ggattacaaa atttgtgaaa gattgactgg tattcttaac tatgttgctc cttttacgct    1500
atgtggatac gctgctttaa tgcctttgta tcatgctatt gcttcccgta tggctttcat    1560
tttctcctcc ttgtataaat cctggttgct gtctctttat gaggagttgt ggcccgttgt    1620
caggcaacgt ggcgtggtgt gcactgtgtt tgctgacgca accccactg gttggggcat    1680
tgccaccacc tgtcagctcc tttccgggac tttcgctttc ccctcccta ttgccacggc    1740
ggaactcatc gccgcctgcc ttgcccgctg ctggacaggg gctcggctgt gggcactga    1800
caattccgtg tgttgtcgg ggaaatcatc gtcctttcct tggctgctcg cctgtgttgc    1860
cacctggatt ctgcgcggga cgtccttctg ctacgtccct tcggccctca atccagcgga    1920
ccttccttcc cgcggcctgc tgccggctct gcggcctctt ccgcctcttc gccttcgccc    1980
tcagacgagt cggatctccc tttgggccgc ctccccgcat ctgtgccttc tagttgccag    2040
ccatctgttg tttgcccctc cccgtgcctt ccttgaccc tggaaggtgc cactccccact    2100
gtcctttcct aataaaatga ggaaattgca tcgcattgtc tgagtaggtg tcattctatt    2160
ctgggggggtg ggtgggggca ggacagcaag ggggaggatt ggcaagacaa tagcaggctt    2220
```

```
tgcatttta gacatttaga agcctatatc ttgttacaga attggaatta cacaaaaatt    2280
ctaccatatt ttgaaagctt aggttgttct gaaaaaaaca atatattgtt ttcctgggta    2340
aactaaaagt cccctcgagg aaaggcccct aaagtgaaac agtgcaaaac gttcaaaaac    2400
tgtctggcaa tacaagttcc actttgacca aaacggctgg cagtaaaagg gttaagaaga    2460
ctgtcagcct tgagcggtat cagctcactc aaaggcggta atacggttat ccacagaatc    2520
aggggataac gcaggaaaga acatgtgagc aaaaggccag caaaaggcca ggaaccgtaa    2580
aaaggccgcg ttgctggcgt ttttccatag gctccgcccc cctgacgagc atcacaaaaa    2640
tcgacgctca agtcagaggt ggcgaaaccc gacaggacta taaagatacc aggcgtttcc    2700
ccctggaagc tccctcgtgc gctctcctgt tccgaccctg ccgcttaccg gatacctgtc    2760
cgccttctcc cttcgggaa gcgtggcgct ttctcatagc tcacgctgta ggtatctcag    2820
ttcggtgtag gtcgttcgct ccaagctggg ctgtgtgcac gaaccccccg ttcagcccga    2880
ccgctgcgcc ttatccggta actatcgtct tgagtccaac ccggtaagac acgacttatc    2940
gccactggca gcagccactg gtaacaggat tagcagagcg aggtatgtag gcggtgctac    3000
agagttcttg aagtggtggg ctaactacgg ctacactaga agaacagtat ttggtatctg    3060
cgctctgctg aagccagtta ccttcggaaa aagagttggt agctcttgat ccggcaaaca    3120
aaccaccgct ggtagcggtg gtttttttgt ttgcaagcag cagattacgc gcagaaaaaa    3180
aggatctcaa gaagatcctt tgatcttttc tacggggtct gacgctcagt ggaacgacgc    3240
gcgcgtaact cacgttaagg gattttggtc atgagttaga aaaactcatc gagcatcaaa    3300
tgaaactgca atttattcat atcaggatta tcaataccat attttgaaa aagccgtttc    3360 tgtaatgaag gagaaaactc accgaggcag ttccatagga tggcaagatc ctggtatcgg    3420
tctgcgattc cgactcgtcc aacatcaata caacctatta atttccctc gtcaaaata    3480 aggttatcaa gtgagaaatc accatgagtg acgactgaat ccggtgagaa tggcaaaagt    3540
ttatgcattt ctttccagac ttgttcaaca ggccagccat tacgctcgtc atcaaaatca    3600
ctcgcatcaa ccaaaccgtt attcattcgt gattgcgcct gagcgaggcg aaatacgcga    3660
tcgctgttaa aaggacaatt acaaacagga atcgagtgca accggcgcag gaacactgcc    3720
agcgcatcaa caatattttc acctgaatca ggatattctt ctaatacctg gaacgctgtt    3780
tttccgggga tcgcagtggt gagtaaccat gcatcatcag gagtacggat aaaatgcttg    3840
atggtcggaa gtggcataaa ttccgtcagc cagtttagtc tgaccatctc atctgtaaca    3900
tcattggcaa cgctaccttt gccatgtttc agaaacaact ctggcgcatc gggcttccca    3960
tacaagcgat agattgtcgc acctgattgc ccgacattat cgcgagccca tttatacccca    4020 tataaatcag catccatgtt ggaatttaat cgcggcctcg acgtttcccg ttggatatgg    4080
ctcatttttt acttcctcac cttgtcgtat tatactatgc cgatatacta tgccgatgat    4140
taattgtcga cactgcgggg gctctgtgtg gtaagcaggt cttaaccttt ttactgccaa    4200
tgacgcatgg gatacgtcgt ggcagtaaaa gggcttaaat gccaacgacg cgtcccatac    4260
gttgttggca tttaattct tctctctgca gcggcagcat gtgccgccgc tgcagagagt    4320
ttctagcgat gacagcccct ctgggcaacg agccgggggg gctgtctttc tttatgtttt    4380
aaatgcactg acctcccaca ttccctttt agtaaaatat tcagaaataa tttaaataca    4440
tcattgcaat gaaaataaat gttttttatt aggcagaatc cagatgctca aggcccttca    4500
taatatcccc cagtttagta gttggactta gggaacaaag gaacctttaa tagaaattgg    4560
acagcaagaa agcgagtcag gcaccgggct tgcgggtcat gcaccaggtg cgcggtcctt    4620
```

```
cgggcacctc gacgtcggcg gtgacggtga agccgagccg ctcgtagaag gggaggttgc    4680
ggggcgcgga tgtctccagg aaggcgggca ccccggcgcg ctcggccgcc tccactccgg    4740
ggagcacgac ggcgctgccc agacccttgc cctggtggtc gggcgacacg ccgacggtgg    4800
ccaggaacca cgcgggctcc ttgggccggt gcggcgccag gaggccttcc atctgttgct    4860
gcgcggccag ccgggaaccg ctcaactcgg ccatgcgcgg gccgatctcg gcgaacaccg    4920
cccccgcttc gacgctctcc ggcgtggtcc agaccgccac cgcggcgccg tcgtccgcga    4980
cccacacctt gccgatgtcg agcccgacgc gcgtgaggaa gagttcttgc agctcggtga    5040
cccgctcgat gtggcggtcc ggatcgacgg tgtggcgcgt ggcggggtag tcggcgaacg    5100
cggcggcgag ggtgcgtacg gccctgggga cgtcgtcgcg ggtggcgagg cgcaccgtgg    5160
gcttgtactc ggtcatggtg gcggacgaaa ggcccggaga tgaggaagag gagaacagcg    5220
cggcagacgt gcgcttttga agcgtgcaga atgccgggcc tccggaggac cttcgggcgc    5280
ccgccccgcc cctgagcccg ccctgagcc cgccccgga cccacccctt ccagcctct     5340
gagcccagaa agcgaaggag caaagctgct attggccgct gccccaaagg cctacccgct    5400
tccattgctc agcggtgctg tccatctgca cgagactagt gagtcgtgct acttccattt    5460
gtcacgtcct gcacgacgcg agctgcgggg cgggggggaa cttcctgact aggggaggag    5520
tagaaggtgg cgcgaagggg ccaccaaaga acggagccgg ttggcgccta ccggtggatg    5580
tggaatgtgt gcgaggccag aggccacttg tgtagcgcca agtgcccagc ggggctgcta    5640
aagcgcatgc tccagactgc cttgggaaaa gcgcctcccc tacccggtag agaaacttga    5700
tctgtcgccg caattcaaac ttcgtgaggc tccggtgccc gtcagtgacc tgctatactc    5760
tggagacgac ttacggtaaa tggcccgcct ggctgaccgc caacgaccc cgcccattg     5820
acgtcaataa tgacgtatgt tcccatagta acgccaatag ggactttcca ttgacgtcaa    5880
tgggtggagt atttacggta aactgcccac ttggcagtac atcaagtgta tcatatgcca    5940
agtccgcccc ctattgacgt caatgacggt aaatggcccg cctggcatta tgcccagtac    6000
atgaccttac gggactttcc tacttggcag tacatctacg tattagtcat cgctattacc    6060
atgctgatgc ggtttggca gtacaccaat gggcgtggat agcggtttga ctcacgggga    6120
tttccaagtc tccacccat tgacgtcaat gggagtttgt tttggcacca aaatcaacgg    6180
gactttccaa aatgtcgtaa taaccccgcc ccgttgacga aatgggcgg taggcgtgta    6240
cggtgggagg tctatataag cagagctcgt ttagtgaacc gtcagatcgc ctggagaggc    6300
catccacgct gttttgacct ccatagtgga caccgggacc gatccagcct ccgcgtctca    6360
gg                                                                  6362
```

<210> SEQ ID NO 79
<211> LENGTH: 160
<212> TYPE: PRT
<213> ORGANISM: Artificial Sequence
<220> FEATURE:
<223> OTHER INFORMATION: Synthetic peptide, His-avitag-natural NKG2D
      ectodomain

<400> SEQUENCE: 79

Glu Pro His His His His His His Gly Leu Asn Asp Ile Phe Glu Ala
1               5                   10                  15

Gln Lys Ile Glu Trp His Glu Asn Ser Leu Phe Asn Gln Glu Val Gln
            20                  25                  30

Ile Pro Leu Thr Glu Ser Tyr Cys Gly Pro Cys Pro Lys Asn Trp Ile

```
                35                   40                   45
Cys Tyr Lys Asn Asn Cys Tyr Gln Phe Phe Asp Glu Ser Lys Asn Trp
 50                   55                   60

Tyr Glu Ser Gln Ala Ser Cys Met Ser Gln Asn Ala Ser Leu Leu Lys
 65                   70                   75                   80

Val Tyr Ser Lys Glu Asp Gln Asp Leu Leu Lys Leu Val Lys Ser Tyr
                 85                   90                   95

His Trp Met Gly Leu Val His Ile Pro Thr Asn Gly Ser Trp Gln Trp
            100                  105                  110

Glu Asp Gly Ser Ile Leu Ser Pro Asn Leu Leu Thr Ile Ile Glu Met
        115                  120                  125

Gln Lys Gly Asp Cys Ala Leu Tyr Ala Ser Ser Phe Lys Gly Tyr Ile
    130                  135                  140

Glu Asn Cys Ser Thr Pro Asn Thr Tyr Ile Cys Met Gln Arg Thr Val
145                  150                  155                  160

<210> SEQ ID NO 80
<211> LENGTH: 160
<212> TYPE: PRT
<213> ORGANISM: Artificial Sequence
<220> FEATURE:
<223> OTHER INFORMATION: Synthetic peptide, His-avitag-non-natural NKG2D
      Y152A ectodomain

<400> SEQUENCE: 80

Glu Pro His His His His His Gly Leu Asn Asp Ile Phe Glu Ala
1               5                   10                  15

Gln Lys Ile Glu Trp His Glu Asn Ser Leu Phe Asn Gln Glu Val Gln
            20                  25                  30

Ile Pro Leu Thr Glu Ser Tyr Cys Gly Pro Cys Pro Lys Asn Trp Ile
        35                  40                  45

Cys Tyr Lys Asn Asn Cys Tyr Gln Phe Phe Asp Glu Ser Lys Asn Trp
 50                  55                  60

Tyr Glu Ser Gln Ala Ser Cys Met Ser Gln Asn Ala Ser Leu Leu Lys
 65                  70                  75                  80

Val Tyr Ser Lys Glu Asp Gln Asp Leu Leu Lys Leu Val Lys Ser Ala
                85                  90                  95

His Trp Met Gly Leu Val His Ile Pro Thr Asn Gly Ser Trp Gln Trp
            100                 105                 110

Glu Asp Gly Ser Ile Leu Ser Pro Asn Leu Leu Thr Ile Ile Glu Met
        115                 120                 125

Gln Lys Gly Asp Cys Ala Leu Tyr Ala Ser Ser Phe Lys Gly Tyr Ile
    130                 135                 140

Glu Asn Cys Ser Thr Pro Asn Thr Tyr Ile Cys Met Gln Arg Thr Val
145                 150                 155                 160

<210> SEQ ID NO 81
<211> LENGTH: 160
<212> TYPE: PRT
<213> ORGANISM: Artificial Sequence
<220> FEATURE:
<223> OTHER INFORMATION: Synthetic peptide, His-avitag-non-natural NKG2D
      Y199A ectodomain

<400> SEQUENCE: 81

Glu Pro His His His His His Gly Leu Asn Asp Ile Phe Glu Ala
1               5                   10                  15

Gln Lys Ile Glu Trp His Glu Asn Ser Leu Phe Asn Gln Glu Val Gln
```

```
                    20                  25                  30

Ile Pro Leu Thr Glu Ser Tyr Cys Gly Pro Cys Pro Lys Asn Trp Ile
            35                  40                  45

Cys Tyr Lys Asn Asn Cys Tyr Gln Phe Phe Asp Glu Ser Lys Asn Trp
        50                  55                  60

Tyr Glu Ser Gln Ala Ser Cys Met Ser Gln Asn Ala Ser Leu Leu Lys
65                  70                  75                  80

Val Tyr Ser Lys Glu Asp Gln Asp Leu Leu Lys Leu Val Lys Ser Tyr
                85                  90                  95

His Trp Met Gly Leu Val His Ile Pro Thr Asn Gly Ser Trp Gln Trp
            100                 105                 110

Glu Asp Gly Ser Ile Leu Ser Pro Asn Leu Leu Thr Ile Ile Glu Met
        115                 120                 125

Gln Lys Gly Asp Cys Ala Leu Tyr Ala Ser Ser Phe Lys Gly Ala Ile
    130                 135                 140

Glu Asn Cys Ser Thr Pro Asn Thr Tyr Ile Cys Met Gln Arg Thr Val
145                 150                 155                 160

<210> SEQ ID NO 82
<211> LENGTH: 160
<212> TYPE: PRT
<213> ORGANISM: Artificial Sequence
<220> FEATURE:
<223> OTHER INFORMATION: Synthetic peptide, His-avitag-non-natural NKG2D
      Y152A +Y199A ectodomain

<400> SEQUENCE: 82

Glu Pro His His His His His His Gly Leu Asn Asp Ile Phe Glu Ala
1               5                   10                  15

Gln Lys Ile Glu Trp His Glu Asn Ser Leu Phe Asn Gln Glu Val Gln
            20                  25                  30

Ile Pro Leu Thr Glu Ser Tyr Cys Gly Pro Cys Pro Lys Asn Trp Ile
        35                  40                  45

Cys Tyr Lys Asn Asn Cys Tyr Gln Phe Phe Asp Glu Ser Lys Asn Trp
    50                  55                  60

Tyr Glu Ser Gln Ala Ser Cys Met Ser Gln Asn Ala Ser Leu Leu Lys
65                  70                  75                  80

Val Tyr Ser Lys Glu Asp Gln Asp Leu Leu Lys Leu Val Lys Ser Ala
                85                  90                  95

His Trp Met Gly Leu Val His Ile Pro Thr Asn Gly Ser Trp Gln Trp
            100                 105                 110

Glu Asp Gly Ser Ile Leu Ser Pro Asn Leu Leu Thr Ile Ile Glu Met
        115                 120                 125

Gln Lys Gly Asp Cys Ala Leu Tyr Ala Ser Ser Phe Lys Gly Ala Ile
    130                 135                 140

Glu Asn Cys Ser Thr Pro Asn Thr Tyr Ile Cys Met Gln Arg Thr Val
145                 150                 155                 160

<210> SEQ ID NO 83
<211> LENGTH: 7640
<212> TYPE: DNA
<213> ORGANISM: Artificial Sequence
<220> FEATURE:
<223> OTHER INFORMATION: Synthetic polynucleotide, wt MIC-Fc expression
      vector

<400> SEQUENCE: 83
ggagagacca cacccaagct gtctagagcc gccaacatgg ggctgggccc ggtcttcctg      60
```

-continued

```
cttctggctg gcatcttccc ttttgcacct ccgggagctg ctgctgagcc ccacagtctt    120
cgttataacc tcacggtgct gtcctgggat ggatctgtgc agtcagggtt tctcactgag    180
gtacatctgg atggtcagcc cttcctgcgc tgtgacaggc agaaatgcag ggcaaagccc    240
cagggacagt gggcagaaga tgtcctggga ataagacat gggacagaga gaccagagac     300
ttgacagggt ggggaaagga cctcaggatg accctggctc atatcaagga ccagaaagaa    360
ggcttgcatt ccctccagga gattagggtc tgtgagatcc atgaagacaa cagcaccagg    420
agctcccagc atttctacta cgatggggag ctctttctct cccaaaacct ggagactaag    480
gaatggacaa tgccccagtc ctccagagct cagaccttgg ccatgaacgt caggaatttc    540
ttgaaggaag atgcaatgga gaccgataca cactatcacg ctatgcatgc agactgcctg    600
caggaactac ggcgatatct aaaatccggc gtagtcctga ggagaacagt gcccccatg     660 gtgaatgtca cccgcagcga ggcctcagag ggcaacatta ccgtgacatg cagggcttct    720
ggcttctatc cctggaatat cacactgagc tggcgtcagg atggggtatc tttgagccac    780
gacacccagc agtgggggga tgtcctgcct gatgggaatg gaacctacca gacctgggtg    840
gccaccagga tttgccaagg agaggagcag aggttcacct gctacatgga acacagcggg    900
aatcacagca ctcaccctgt gccctctggg aaaatcgaag gacgcatgga cccaaagagt    960
tgcgacaaaa ctcacacatg cccaccgtgc ccaggtaagc cagcccaggc ctcgccctcc   1020
agctcaaggc gggacaggtg ccctagagta gcctgcatcc agggacaggc cccagccggg   1080
tgctgacacg tccacctcca tctcttcctc agcacctgaa ctcctggggg gaccgtcagt   1140
cttcctcttc cccccaaaac ccaaggacac cctcatgatc tcccgaccc ctgaggtcac     1200 atgcgtggtg gtggacgtga gccacgaaga ccctgaggtc aagttcaact ggtacgtgga   1260
cggcgtggag gtgcataatg ccaagacaaa gccgcgggag gagcagtaca acagcacgta   1320
ccgtgtggtc agcgtcctca ccgtcctgca ccaggactgg ctgaatggca aggagtacaa   1380
gtgcaaggtc tccaacaaag ccctcccagc ccccatcgag aaaaccatct ccaaagccaa   1440
aggtgggacc cgtggggtgc gagggccaca tggacagagg ccggctcggc ccaccctctg   1500
ccctgagagt gactgctgta ccaacctctg tccctacagg gcagcccga gaaccacagg    1560 tgtacaccct gccccatcc cgggatgagc tgaccaagaa ccaggtcagc ctgacctgcc    1620
tggtcaaagg cttctatccc agcgacatcg ccgtggagtg ggagagcaat gggcagccgg   1680
agaacaacta caagaccacg cctcccgtgc tggactccga cggctccttc ttcctctaca   1740
gcaagctcac cgtggacaag agcaggtggc agcaggggaa cgtcttctca tgctccgtga   1800
tgcatgaggc tctgcacaac cactacacgc agaagagcct ctccctgtct ccgggtaaat   1860
gataggatcc ggttgaggtc tctaaaagcg tcttcctgtt ctcatcacat catatcaagg   1920
ttatatacca tcaatattgc cacagatgtt acttagcctt ttaatatttc tctaatttag   1980
tgtatatgca atgatagttc tctgatttct gagattgagt ttctcatgtg taatgattat   2040
ttagagtttc tctttcatct gttcaaattt ttgtctagtt ttatttttta ctgatttgta   2100
agacttcttt ttataatctg catattacaa ttctctttac tggggtgttg caaatatttt   2160
ctgtcattct atggcctgac ttttcttaat ggttttttaa ttttaaaaat aagtcttaat   2220
attcatgcaa tctaattaac aatcttttct ttgtggttag gactttgagt cataagaaat   2280
ttttctctac actgaagtca tgatggcatg cttctatatt attttctaaa agatttaaag   2340
ttttgccttc tccatttaga cttataattc actggaattt ttttgtgtgt atggtatgac   2400
```

```
atatgggttc ccttttattt tttacatata aatatatttc cctgttttc taaaaagaa    2460
aaagatcatc attttcccat tgtaaaatgc catattttt tcataggtca cttacatata    2520
tcaatgggtc tgtttctgag ctctactcta ttttatcagc ctcactgtct atccccacac   2580
atctcatgct ttgctctaaa tcttgatatt tagtggaaca ttctttccca ttttgttcta   2640
caagaatatt tttgttattg tctttgggct ttctatatac attttgaaat gaggttgaca   2700
agttaataat caacctctgg attacaaaat ttgtgaaaga ttgactggta ttcttaacta   2760
tgttgctcct tttacgctat gtggatacgc tgctttaatg cctttgtatc atgctattgc   2820
ttcccgtatg gctttcattt tctcctcctt gtataaatcc tggttgctgt ctctttatga   2880
ggagttgtgg cccgttgtca ggcaacgtgg cgtggtgtgc actgtgtttg ctgacgcaac   2940
ccccactggt tggggcattg ccaccacctg tcagctcctt tccgggactt tcgctttccc   3000
cctccctatt gccacggcgg aactcatcgc cgcctgcctt gcccgctgct ggacaggggc   3060
tcggctgttg ggcactgaca attccgtggt gttgtcgggg aaatcatcgt cctttccttg   3120
gctgctcgcc tgtgttgcca cctggattct gcgcgggacg tccttctgct acgtcccttc   3180
ggccctcaat ccagcggacc ttccttcccg cggcctgctg ccggctctgc ggcctcttcc   3240
gcctcttcgc cttcgccctc agacgagtcg gatctccctt gggccgcct ccccgcatct    3300
gtgccttcta gttgccagcc atctgttgtt tgccctccc ccgtgccttc cttgaccctg    3360
gaaggtgcca ctcccactgt cctttcctaa taaaatgagg aaattgcatc gcattgtctg   3420
agtaggtgtc attctattct ggggggtggg gtggggcagg acagcaaggg ggaggattgg   3480
caagacaata gcaggctttg catttttaga catttagaag cctatatctt gttacagaat   3540
tggaattaca caaaaattct accatatttt gaaagcttag gttgttctga aaaaaacaat   3600
atattgtttt cctgggtaaa ctaaaagtcc cctcgaggaa aggcccctaa agtgaaacag   3660
tgcaaaacgt tcaaaaactg tctggcaata caagttccac tttgaccaaa acggctggca   3720
gtaaaagggt taagaagact gtcagccttg agcggtatca gctcactcaa aggcggtaat   3780
acggttatcc acagaatcag gggataacgc aggaaagaac atgtgagcaa aaggccagca   3840
aaaggccagg aaccgtaaaa aggccgcgtt gctggcgttt ttccataggc tccgcccccc   3900
tgacgagcat cacaaaaatc gacgctcaag tcagaggtgg cgaaacccga caggactata   3960
aagataccag gcgtttcccc ctggaagctc cctcgtgcgc tctcctgttc cgaccctgcc   4020
gcttaccgga tacctgtccg cctttctccc ttcgggaagc gtggcgcttt ctcatagctc   4080
acgctgtagg tatctcagtt cggtgtaggt cgttcgctcc aagctgggct gtgtgcacga   4140
accccccgtt cagcccgacc gctgcgcctt atccggtaac tatcgtcttg agtccaaccc   4200
ggtaagacac gacttatcgc cactggcagc agccactggt aacaggatta gcagagcgag   4260
gtatgtaggc ggtgctacag agttcttgaa gtggtgggct aactacggct acactagaag   4320
aacagtattt ggtatctgcg ctctgctgaa gccagttacc ttcggaaaaa gagttggtag   4380
ctcttgatcc ggcaaacaaa ccaccgctgg tagcggtggt ttttttgttt gcaagcagca   4440
gattacgcgc agaaaaaaag gatctcaaga agatcctttg atcttttcta cggggtctga   4500
cgctcagtgg aacgacgcgc gcgtaactca cgttaaggga ttttggtcat gagttagaaa   4560
aactcatcga gcatcaaatg aaactgcaat ttattcatat caggattatc aataccatat   4620
ttttgaaaaa gccgtttctg taatgaagga gaaaactcac cgaggcagtt ccataggatg   4680
gcaagatcct ggtatcggtc tgcgattccg actcgtccaa catcaataca acctattaat   4740
ttccccctcgt caaaaataag gttatcaagt gagaaatcac catgagtgac gactgaatcc   4800
```

```
ggtgagaatg gcaaaagttt atgcatttct ttccagactt gttcaacagg ccagccatta    4860
cgctcgtcat caaaatcact cgcatcaacc aaaccgttat tcattcgtga ttgcgcctga    4920
gcgaggcgaa atacgcgatc gctgttaaaa ggacaattac aaacaggaat cgagtgcaac    4980
cggcgcagga acactgccag cgcatcaaca atattttcac ctgaatcagg atattcttct    5040
aatacctgga acgctgtttt tccggggatc gcagtggtga gtaaccatgc atcatcagga    5100
gtacggataa aatgcttgat ggtcggaagt ggcataaatt ccgtcagcca gtttagtctg    5160
accatctcat ctgtaacatc attggcaacg ctacctttgc catgtttcag aaacaactct    5220
ggcgcatcgg gcttcccata caagcgatag attgtcgcac ctgattgccc gacattatcg    5280
cgagcccatt tacccata taaatcagca tccatgttgg aatttaatcg cggcctcgac    5340
gtttcccgtt ggatatggct cattttttac ttcctcacct tgtcgtatta tactatgccg    5400
atatactatg ccgatgatta attgtcgaca ctgcggggc tctgtgtggt aagcaggtct    5460
taaccttttt actgccaatg acgcatggga tacgtcgtgg cagtaaaagg cttaaatgc    5520 caacgacgcg tcccatacgt tgttggcatt ttaattcttc tctctgcagc ggcagcatgt    5580
gccgccgctg cagagagttt ctagcgatga cagcccctct gggcaacgag ccggggggc    5640 tgtctttctt tatgttttaa atgcactgac ctcccacatt cccttttag taaaatattc    5700 agaaataatt taaatacatc attgcaatga aaataaatgt ttttattag gcagaatcca    5760 gatgctcaag gcccttcata atatccccca gtttagtagt tggacttagg aacaaagga    5820 acctttaata gaaattggac agcaagaaag cgagtcaggc accgggcttg cgggtcatgc    5880
accaggtgcg cggtccttcg ggcacctcga cgtcggcggt gacggtgaag ccgagccgct    5940
cgtagaaggg gaggttgcgg ggcgcggatg tctccaggaa ggcgggcacc ccggcgcgct    6000
cggccgcctc cactccgggg agcacgacgg cgctgcccag acccttgccc tggtggtcgg    6060
gcgacacgcc gacggtggcc aggaaccacg cgggctcctt gggccggtgc ggcgccagga    6120
ggccttccat ctgttgctgc gcggccagcc gggaaccgct caactcggcc atgcgcgggc    6180
cgatctcggc gaacaccgcc cccgcttcga cgctctccgg cgtggtccag accgccaccg    6240
cggcgccgtc gtccgcgacc cacaccttgc cgatgtcgag cccgacgcgc gtgaggaaga    6300
gttcttgcag ctcggtgacc cgctcgatgt ggcggtccgg atcgacggtg tggcgcgtgg    6360
cggggtagtc ggcgaacgcg gcggcgaggg tgcgtacggc cctggggacg tcgtcgcggg    6420
tggcgaggcg caccgtgggc ttgtactcgg tcatggtggc ggacgaaagg cccggagatg    6480
aggaagagga gaacagcgcg gcagacgtgc gcttttgaag cgtgcagaat gccgggcctc    6540
cggaggacct tcgggcgccc gccccgcccc tgagcccgcc cctgagcccg ccccggacc    6600 caccccttcc cagcctctga gcccagaaag cgaaggagca aagctgctat tggccgctgc    6660
cccaaaggcc tacccgcttc cattgctcag cggtgctgtc catctgcacg agactagtga    6720
gtcgtgctac ttccatttgt cacgtcctgc acgacgcgag ctgcggggcg gggggaact    6780 tcctgactag gggaggagta gaaggtggcg cgaagggcc accaaagaac ggagccggtt    6840
ggcgcctacc ggtggatgtg gaatgtgtgc gaggccagag gccacttgtg tagcgccaag    6900
tgcccagcgg ggctgctaaa gcgcatgctc cagactgcct gggaaaagc gcctccccta    6960 cccggtagag aaacttgatc tgtcgccgca attcaaactt cgtgaggctc cggtgcccgt    7020
cagtgacctg ctatactctg gagacgactt acggtaaatg gcccgcctgg ctgaccgccc    7080
aacgaccccc gcccattgac gtcaataatg acgtatgttc ccatagtaac gccaataggg    7140
```

```
acttccatt gacgtcaatg ggtggagtat ttacggtaaa ctgcccactt ggcagtacat    7200
caagtgtatc atatgccaag tccgcccct attgacgtca atgacggtaa atggcccgcc    7260
tggcattatg cccagtacat gaccttacgg gactttccta cttggcagta catctacgta    7320
ttagtcatcg ctattaccat gctgatgcgg ttttggcagt acaccaatgg gcgtggatag    7380
cggtttgact cacggggatt tccaagtctc cacccccattg acgtcaatgg gagtttgttt    7440
tggcaccaaa atcaacggga ctttccaaaa tgtcgtaata accccgcccc gttgacgcaa    7500
atgggcggta ggcgtgtacg gtgggaggtc tatataagca gagctcgttt agtgaaccgt    7560
cagatcgcct ggagaggcca tccacgctgt tttgacctcc atagtggaca ccgggaccga    7620
tccagcctcc gcgtctcagg                                                7640
```

<210> SEQ ID NO 84
<211> LENGTH: 438
<212> TYPE: PRT
<213> ORGANISM: Artificial Sequence
<220> FEATURE:
<223> OTHER INFORMATION: Synthetic peptide, MICA-Fc

<400> SEQUENCE: 84

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Ser Gln Gly Glu Glu Gln Arg
                245                 250                 255

Phe Thr Cys Tyr Met Glu His Ser Gly Asn His Ser Thr His Pro Val
            260                 265                 270
```

```
Pro Ser Gly Lys Ile Glu Gly Arg Met Asp Pro Lys Ser Cys Asp Lys
            275                 280                 285

Thr His Thr Cys Pro Pro Cys Pro Ala Pro Glu Leu Leu Gly Gly Pro
    290                 295                 300

Ser Val Phe Leu Phe Pro Pro Lys Pro Lys Asp Thr Leu Met Ile Ser
305                 310                 315                 320

Arg Thr Pro Glu Val Thr Cys Val Val Val Asp Val Ser His Glu Asp
                325                 330                 335

Pro Glu Val Lys Phe Asn Trp Tyr Val Asp Gly Val Glu Val His Asn
            340                 345                 350

Ala Lys Thr Lys Pro Arg Glu Glu Gln Tyr Asn Ser Thr Tyr Arg Val
        355                 360                 365

Val Ser Val Leu Thr Val Leu His Gln Asp Trp Leu Asn Gly Lys Glu
    370                 375                 380

Tyr Lys Cys Lys Val Ser Asn Lys Ala Leu Pro Ala Pro Ile Glu Lys
385                 390                 395                 400

Thr Ile Ser Lys Ala Lys Gly Gln Pro Arg Glu Pro Gln Val Tyr Thr
                405                 410                 415

Leu Pro Pro Ser Arg Asp Glu Leu Thr Lys Asn Gln Val Ser Leu Thr
            420                 425                 430

Cys Leu Val Lys Gly Phe
            435

<210> SEQ ID NO 85
<211> LENGTH: 513
<212> TYPE: PRT
<213> ORGANISM: Artificial Sequence
<220> FEATURE:
<223> OTHER INFORMATION: Synthetic peptide, MICwed-Fc

<400> SEQUENCE: 85

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190
```

```
Ala Ser Glu Gly Asn Ile Thr Val Thr Cys Arg Ala Ser Gly Phe Tyr
            195                 200                 205
Pro Trp Asn Ile Thr Leu Ser Trp Arg Gln Asp Gly Val Ser Leu Ser
        210                 215                 220
His Asp Thr Gln Gln Trp Gly Asp Val Leu Pro Asp Gly Asn Gly Thr
225                 230                 235                 240
Tyr Gln Thr Trp Val Ala Thr Arg Ile Ser Gln Gly Glu Glu Gln Arg
                245                 250                 255
Phe Thr Cys Tyr Met Glu His Ser Gly Asn His Ser Thr His Pro Val
            260                 265                 270
Pro Ser Gly Lys Ile Glu Gly Arg Met Asp Pro Lys Ser Cys Asp Lys
        275                 280                 285
Thr His Thr Cys Pro Pro Cys Pro Ala Pro Glu Leu Leu Gly Gly Pro
290                 295                 300
Ser Val Phe Leu Phe Pro Pro Lys Pro Lys Asp Thr Leu Met Ile Ser
305                 310                 315                 320
Arg Thr Pro Glu Val Thr Cys Val Val Val Asp Val Ser His Glu Asp
                325                 330                 335
Pro Glu Val Lys Phe Asn Trp Tyr Val Asp Gly Val Glu Val His Asn
            340                 345                 350
Ala Lys Thr Lys Pro Arg Glu Glu Gln Tyr Asn Ser Thr Tyr Arg Val
        355                 360                 365
Val Ser Val Leu Thr Val Leu His Gln Asp Trp Leu Asn Gly Lys Glu
    370                 375                 380
Tyr Lys Cys Lys Val Ser Asn Lys Ala Leu Pro Ala Pro Ile Glu Lys
385                 390                 395                 400
Thr Ile Ser Lys Ala Lys Gly Gln Pro Arg Glu Pro Gln Val Tyr Thr
                405                 410                 415
Leu Pro Pro Ser Arg Asp Glu Leu Thr Lys Asn Gln Val Ser Leu Thr
            420                 425                 430
Cys Leu Val Lys Gly Phe Tyr Pro Ser Asp Ile Ala Val Glu Trp Glu
        435                 440                 445
Ser Asn Gly Gln Pro Glu Asn Asn Tyr Lys Thr Thr Pro Pro Val Leu
    450                 455                 460
Asp Ser Asp Gly Ser Phe Phe Leu Tyr Ser Lys Leu Thr Val Asp Lys
465                 470                 475                 480
Ser Arg Trp Gln Gln Gly Asn Val Phe Ser Cys Ser Val Met His Glu
                485                 490                 495
Ala Leu His Asn His Tyr Thr Gln Lys Ser Leu Ser Leu Ser Pro Gly
            500                 505                 510
Lys

<210> SEQ ID NO 86
<211> LENGTH: 513
<212> TYPE: PRT
<213> ORGANISM: Artificial Sequence
<220> FEATURE:
<223> OTHER INFORMATION: Synthetic peptide, MICv25-Fc

<400> SEQUENCE: 86

Glu Pro His Ser Leu Arg Tyr Asn Leu Thr Val Leu Ser Trp Asp Gly
1               5                   10                  15
Ser Val Gln Ser Gly Phe Leu Thr Glu Val His Leu Asp Gly Gln Pro
                20                  25                  30
Phe Leu Arg Cys Asp Arg Gln Lys Cys Arg Ala Lys Pro Gln Gly Gln
```

```
            35                  40                  45
Trp Ala Glu Asp Val Leu Gly Asn Lys Thr Trp Asp Arg Glu Thr Arg
 50                  55                  60
Asp Leu Thr Gly Trp Gly Lys Asp Leu Arg Met Thr Leu Ala His Ile
 65                  70                  75                  80
Lys Asp Gln Lys Glu Gly Leu His Ser Leu Gln Glu Ile Arg Val Cys
                 85                  90                  95
Glu Ile His Glu Asp Asn Ser Thr Arg Ser Ser Gln His Phe Tyr Tyr
                100                 105                 110
Asp Gly Glu Leu Phe Leu Ser Gln Asn Leu Glu Thr Leu Glu Trp Thr
                115                 120                 125
Met Pro Gln Ser Ser Arg Ala Gln Thr Leu Ala Met Asn Val Arg Asn
        130                 135                 140
Phe Leu Lys Glu Asp Ala Met Glu Thr Asp Thr His Tyr His Ala Met
145                 150                 155                 160
Arg Ala Asp Cys Leu Ser Glu Leu Arg Arg Tyr Leu Lys Ser Gly Val
                165                 170                 175
Val Leu Arg Arg Thr Val Pro Pro Met Val Asn Val Thr Arg Ser Glu
        180                 185                 190
Ala Ser Glu Gly Asn Ile Thr Val Thr Cys Arg Ala Ser Gly Phe Tyr
        195                 200                 205
Pro Trp Asn Ile Thr Leu Ser Trp Arg Gln Asp Gly Val Ser Leu Ser
210                 215                 220
His Asp Thr Gln Gln Trp Gly Asp Val Leu Pro Asp Gly Asn Gly Thr
225                 230                 235                 240
Tyr Gln Thr Trp Val Ala Thr Arg Ile Ser Gln Gly Glu Glu Gln Arg
                245                 250                 255
Phe Thr Cys Tyr Met Glu His Ser Gly Asn His Ser Thr His Pro Val
                260                 265                 270
Pro Ser Gly Lys Ile Glu Gly Arg Met Asp Pro Lys Ser Cys Asp Lys
        275                 280                 285
Thr His Thr Cys Pro Pro Cys Pro Ala Pro Glu Leu Leu Gly Gly Pro
        290                 295                 300
Ser Val Phe Leu Phe Pro Pro Lys Pro Lys Asp Thr Leu Met Ile Ser
305                 310                 315                 320
Arg Thr Pro Glu Val Thr Cys Val Val Val Asp Val Ser His Glu Asp
                325                 330                 335
Pro Glu Val Lys Phe Asn Trp Tyr Val Asp Gly Val Glu Val His Asn
                340                 345                 350
Ala Lys Thr Lys Pro Arg Glu Glu Gln Tyr Asn Ser Thr Tyr Arg Val
        355                 360                 365
Val Ser Val Leu Thr Val Leu His Gln Asp Trp Leu Asn Gly Lys Glu
        370                 375                 380
Tyr Lys Cys Lys Val Ser Asn Lys Ala Leu Pro Ala Pro Ile Glu Lys
385                 390                 395                 400
Thr Ile Ser Lys Ala Lys Gly Gln Pro Arg Glu Pro Gln Val Tyr Thr
                405                 410                 415
Leu Pro Pro Ser Arg Asp Glu Leu Thr Lys Asn Gln Val Ser Leu Thr
                420                 425                 430
Cys Leu Val Lys Gly Phe Tyr Pro Ser Asp Ile Ala Val Glu Trp Glu
                435                 440                 445
Ser Asn Gly Gln Pro Glu Asn Asn Tyr Lys Thr Thr Pro Pro Val Leu
        450                 455                 460
```

-continued

```
Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
                485                 490                 495

Ala Leu His Asn His Tyr Thr Gln Lys Ser Leu Ser Leu Ser Pro Gly
            500                 505                 510

Lys

<210> SEQ ID NO 87
<211> LENGTH: 186
<212> TYPE: PRT
<213> ORGANISM: Artificial Sequence
<220> FEATURE:
<223> OTHER INFORMATION: Synthetic peptide, ULBP2 R80W

<400> SEQUENCE: 87

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
                20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Trp
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
        115                 120                 125

Lys Arg Met Trp Thr Thr Val His Pro Gly Ala Arg Lys Met Lys Glu
    130                 135                 140

Lys Trp Glu Asn Asp Lys Val Val Ala Met Ser Phe His Tyr Phe Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro
            180                 185

<210> SEQ ID NO 88
<211> LENGTH: 186
<212> TYPE: PRT
<213> ORGANISM: Artificial Sequence
<220> FEATURE:
<223> OTHER INFORMATION: Synthetic peptide, ULBP2 V151D

<400> SEQUENCE: 88

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
                20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
    50                  55                  60
```

```
Asn Pro Val Leu Arg Glu Val Asp Ile Leu Thr Glu Gln Leu Arg
 65                  70                  75                  80

Asp Ile Gln Leu Glu Asn Tyr Thr Pro Lys Glu Pro Leu Thr Leu Gln
                 85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
                115                 120                 125

Lys Arg Met Trp Thr Thr Val His Pro Gly Ala Arg Lys Met Lys Glu
            130                 135                 140

Lys Trp Glu Asn Asp Lys Asp Val Ala Met Ser Phe His Tyr Phe Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro
            180                 185
```

<210> SEQ ID NO 89
<211> LENGTH: 184
<212> TYPE: PRT
<213> ORGANISM: Artificial Sequence
<220> FEATURE:
<223> OTHER INFORMATION: Synthetic peptide, ULBP3 R162G

<400> SEQUENCE: 89

```
Ala Ala Glu Pro His Ser Leu Trp Tyr Asn Phe Thr Ile Ile His Leu
1               5                  10                  15

Pro Arg His Gly Gln Gln Trp Cys Glu Val Gln Ser Gln Val Asp Gln
                20                  25                  30

Lys Asn Phe Leu Ser Tyr Asp Cys Gly Ser Asp Lys Val Leu Ser Met
            35                  40                  45

Gly His Leu Glu Glu Gln Leu Tyr Ala Thr Asp Ala Trp Gly Lys Gln
        50                  55                  60

Leu Glu Met Leu Arg Glu Val Gly Gln Arg Leu Arg Leu Glu Leu Ala
65                  70                  75                  80

Asp Thr Glu Leu Glu Asp Phe Thr Pro Ser Gly Pro Leu Thr Leu Gln
                85                  90                  95

Val Arg Met Ser Cys Glu Ser Glu Ala Asp Gly Tyr Ile Arg Gly Ser
            100                 105                 110

Trp Gln Phe Ser Phe Asp Gly Arg Lys Phe Leu Leu Phe Asp Ser Asn
                115                 120                 125

Asn Arg Lys Trp Thr Val Val His Ala Gly Ala Arg Arg Met Lys Glu
            130                 135                 140

Lys Trp Glu Lys Asp Ser Gly Leu Thr Thr Phe Phe Lys Met Val Ser
145                 150                 155                 160

Met Gly Asp Cys Lys Ser Trp Leu Arg Asp Phe Leu Met His Arg Lys
                165                 170                 175

Lys Arg Leu Glu Pro Thr Ala Pro
            180
```

<210> SEQ ID NO 90
<211> LENGTH: 182
<212> TYPE: PRT
<213> ORGANISM: Artificial Sequence
<220> FEATURE:
<223> OTHER INFORMATION: Synthetic peptide, MICA25.17

<400> SEQUENCE: 90

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Trp Gly Thr Thr Leu Leu Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Ile Gly Tyr Arg Leu Met
145                 150                 155                 160

Arg Ala Asp Cys Leu Ser Glu Leu Arg Arg Tyr Leu Lys Ser Gly Val
                165                 170                 175

Val Leu Arg Arg Thr Val
            180

<210> SEQ ID NO 91
<211> LENGTH: 182
<212> TYPE: PRT
<213> ORGANISM: Artificial Sequence
<220> FEATURE:
<223> OTHER INFORMATION: Synthetic peptide, MICA25.18

<400> SEQUENCE: 91

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Trp Gly Thr Phe Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Arg Ser Gly Leu Leu Met
145                 150                 155                 160

Arg Ala Asp Cys Leu Ser Glu Leu Arg Arg Tyr Leu Lys Ser Gly Val

```
                    165                 170                 175

Val Leu Arg Arg Thr Val
                180

<210> SEQ ID NO 92
<211> LENGTH: 186
<212> TYPE: PRT
<213> ORGANISM: Artificial Sequence
<220> FEATURE:
<223> OTHER INFORMATION: Synthetic peptide, ULBP2.S1

<400> SEQUENCE: 92

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
                20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Trp
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
                100                 105                 110

Trp Gln Phe Ser Phe Asp Gly Gln Ile Phe Leu Leu Phe Asp Ser Glu
            115                 120                 125

Lys Arg Met Trp Thr Thr Val His Pro Gly Ala Arg Lys Met Lys Glu
    130                 135                 140

Lys Trp Glu Asn Asp Lys Val Val Ala Thr Thr Leu Tyr Thr Trp Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro
            180                 185

<210> SEQ ID NO 93
<211> LENGTH: 186
<212> TYPE: PRT
<213> ORGANISM: Artificial Sequence
<220> FEATURE:
<223> OTHER INFORMATION: Synthetic peptide, ULBP2.S2

<400> SEQUENCE: 93

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
                20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Trp
65                  70                  75                  80

Asp Ile Gln Leu Glu Asn Tyr Thr Pro Lys Glu Pro Leu Thr Leu Gln
                85                  90                  95
```

```
Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
            115                 120                 125

Lys Arg Met Trp Thr Thr Val His Pro Gly Ala Arg Lys Met Lys Glu
            130                 135                 140

Lys Trp Glu Asn Asp Lys Val Ala Thr Leu Met Arg Ile Trp Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro
            180                 185

<210> SEQ ID NO 94
<211> LENGTH: 186
<212> TYPE: PRT
<213> ORGANISM: Artificial Sequence
<220> FEATURE:
<223> OTHER INFORMATION: Synthetic peptide, ULBP2.S3

<400> SEQUENCE: 94

Ala Ala Glu Pro His Ser Leu Ser Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
            35                  40                  45

Ser Pro Leu Gly Lys Lys Leu Asn Val Thr Thr Ala Trp Lys Ala Gln
50                  55                  60

Asn Pro Val Leu Arg Glu Val Val Asp Ile Leu Thr Glu Gln Leu Trp
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
            115                 120                 125

Lys Arg Met Trp Thr Thr Val His Pro Gly Ala Arg Lys Met Lys Glu
            130                 135                 140

Lys Trp Glu Asn Asp Lys Val Ala Thr Lys Leu Tyr Leu Trp Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro
            180                 185

<210> SEQ ID NO 95
<211> LENGTH: 184
<212> TYPE: PRT
<213> ORGANISM: Artificial Sequence
<220> FEATURE:
<223> OTHER INFORMATION: Synthetic peptide, ULBP3.S1

<400> SEQUENCE: 95

Ala Ala Glu Pro His Ser Leu Trp Tyr Asn Phe Thr Ile Ile His Leu
1               5                   10                  15

Pro Arg His Gly Gln Gln Trp Cys Glu Val Gln Ser Gln Val Asp Gln
            20                  25                  30
```

```
Lys Asn Phe Leu Ser Tyr Asp Cys Gly Ser Asp Lys Val Leu Ser Met
                35                  40                  45

Gly His Leu Glu Glu Gln Leu Tyr Ala Thr Asp Ala Trp Gly Lys Gln
 50                  55                  60

Leu Glu Met Leu Arg Glu Val Gly Gln Arg Leu Arg Leu Glu Leu Ala
 65                  70                  75                  80

Asp Thr Glu Leu Glu Asp Phe Thr Pro Ser Gly Pro Leu Thr Leu Gln
                 85                  90                  95

Val Arg Met Ser Cys Glu Ser Glu Ala Asp Gly Tyr Ile Arg Gly Ser
                100                 105                 110

Trp Gln Phe Ser Phe Asp Gly Arg Lys Phe Leu Leu Phe Asp Ser Asn
                115                 120                 125

Asn Arg Lys Trp Thr Val Val His Ala Gly Ala Arg Arg Met Lys Glu
                130                 135                 140

Lys Trp Glu Lys Asp Ser Gly Leu Thr Thr Asp Leu Ile Arg Arg Ser
145                 150                 155                 160

Met Gly Asp Cys Lys Ser Trp Leu Arg Asp Phe Leu Met His Arg Lys
                165                 170                 175

Lys Arg Leu Glu Pro Thr Ala Pro
                180
```

<210> SEQ ID NO 96
<211> LENGTH: 184
<212> TYPE: PRT
<213> ORGANISM: Artificial Sequence
<220> FEATURE:
<223> OTHER INFORMATION: Synthetic peptide ULBP3.S2

<400> SEQUENCE: 96

```
Ala Ala Glu Pro His Ser Leu Trp Tyr Asn Phe Thr Ile Ile His Leu
  1               5                  10                  15

Pro Arg His Gly Gln Gln Trp Cys Glu Val Gln Ser Gln Val Asp Gln
                 20                  25                  30

Lys Asn Phe Leu Ser Tyr Asp Cys Gly Ser Asp Lys Val Leu Ser Met
                 35                  40                  45

Gly His Leu Glu Glu Gln Leu Tyr Ala Thr Asp Ala Trp Gly Lys Gln
 50                  55                  60

Leu Glu Met Leu Arg Glu Val Gly Gln Arg Leu Arg Leu Glu Leu Ala
 65                  70                  75                  80

Asp Thr Glu Leu Glu Asp Phe Thr Pro Ser Gly Pro Leu Thr Leu Gln
                 85                  90                  95

Val Arg Met Ser Cys Glu Ser Glu Ala Asp Gly Tyr Ile Arg Gly Ser
                100                 105                 110

Trp Gln Phe Ser Phe Asp Gly Arg Lys Phe Leu Leu Phe Asp Ser Asn
                115                 120                 125

Asn Arg Lys Trp Thr Val Val His Ala Gly Ala Arg Arg Met Lys Glu
                130                 135                 140

Lys Trp Glu Lys Asp Ser Gly Leu Thr Thr Tyr Phe Tyr Leu Arg Ser
145                 150                 155                 160

Met Gly Asp Cys Lys Ser Trp Leu Arg Asp Phe Leu Met His Arg Lys
                165                 170                 175

Lys Arg Leu Glu Pro Thr Ala Pro
                180
```

<210> SEQ ID NO 97

<211> LENGTH: 657
<212> TYPE: PRT
<213> ORGANISM: Artificial Sequence
<220> FEATURE:
<223> OTHER INFORMATION: Synthetic peptide, R3 HC25.17

<400> SEQUENCE: 97

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
            20                  25                  30

Ser Leu Arg Leu Ser Cys Ala Ala Ser Gly Phe Thr Phe Thr Ser Thr
        35                  40                  45

Gly Ile Ser Trp Val Arg Gln Ala Pro Gly Lys Gly Leu Glu Trp Val
    50                  55                  60

Gly Arg Ile Tyr Pro Thr Asn Gly Ser Thr Asn Tyr Ala Asp Ser Val
65                  70                  75                  80

Lys Gly Arg Phe Thr Ile Ser Ala Asp Thr Ser Lys Asn Thr Ala Tyr
                85                  90                  95

Leu Gln Met Asn Ser Leu Arg Ala Glu Asp Thr Ala Val Tyr Tyr Cys
            100                 105                 110

Ala Arg Thr Tyr Gly Ile Tyr Asp Leu Tyr Val Asp Tyr Thr Glu Tyr
        115                 120                 125

Val Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

```
Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Gly Gly Ser Glu Pro His Ser
465                 470                 475                 480

Leu Arg Tyr Asn Leu Thr Val Leu Ser Trp Asp Gly Ser Val Gln Ser
                485                 490                 495

Gly Phe Leu Thr Glu Val His Leu Asp Gly Gln Pro Phe Leu Arg Cys
            500                 505                 510

Asp Arg Gln Lys Cys Arg Ala Lys Pro Gln Gly Gln Trp Ala Glu Asp
        515                 520                 525

Val Leu Gly Asn Lys Thr Trp Asp Arg Glu Thr Arg Asp Leu Thr Gly
    530                 535                 540

Trp Gly Thr Thr Leu Leu Met Thr Leu Ala His Ile Lys Asp Gln Lys
545                 550                 555                 560

Glu Gly Leu His Ser Leu Gln Glu Ile Arg Val Cys Glu Ile His Glu
                565                 570                 575

Asp Asn Ser Thr Arg Ser Ser Gln His Phe Tyr Tyr Asp Gly Glu Leu
            580                 585                 590

Phe Leu Ser Gln Asn Leu Glu Thr Leu Glu Trp Thr Met Pro Gln Ser
        595                 600                 605

Ser Arg Ala Gln Thr Leu Ala Met Asn Val Arg Asn Phe Leu Lys Glu
    610                 615                 620

Asp Ala Met Glu Thr Asp Ile Gly Tyr Arg Leu Met Arg Ala Asp Cys
625                 630                 635                 640

Leu Ser Glu Leu Arg Arg Tyr Leu Lys Ser Gly Val Val Leu Arg Arg
                645                 650                 655

Thr

<210> SEQ ID NO 98
<211> LENGTH: 656
<212> TYPE: PRT
<213> ORGANISM: Artificial Sequence
<220> FEATURE:
<223> OTHER INFORMATION: Synthetic peptide, R3 HC.U2S3

<400> SEQUENCE: 98

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
                20                  25                  30

Ser Leu Arg Leu Ser Cys Ala Ala Ser Gly Phe Thr Phe Thr Ser Thr
            35                  40                  45

Gly Ile Ser Trp Val Arg Gln Ala Pro Gly Lys Gly Leu Glu Trp Val
        50                  55                  60

Gly Arg Ile Tyr Pro Thr Asn Gly Ser Thr Asn Tyr Ala Asp Ser Val
65                  70                  75                  80
```

```
Lys Gly Arg Phe Thr Ile Ser Ala Asp Thr Ser Lys Asn Thr Ala Tyr
                 85                  90                  95
Leu Gln Met Asn Ser Leu Arg Ala Glu Asp Thr Ala Val Tyr Tyr Cys
            100                 105                 110
Ala Arg Thr Tyr Gly Ile Tyr Asp Leu Tyr Val Asp Tyr Thr Glu Tyr
        115                 120                 125
Val Met Asp Tyr Trp Gly Gln Gly Thr Leu Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
    450                 455                 460
Lys Ser Leu Ser Leu Ser Pro Gly Gly Gly Ser Glu Pro His Ser
465                 470                 475                 480
Leu Ser Tyr Asp Ile Thr Val Ile Pro Lys Phe Arg Pro Gly Pro Arg
                485                 490                 495
Trp Cys Ala Val Gln Gly Gln Val Asp Glu Lys Thr Phe Leu His Tyr
```

```
                500             505             510
Asp Cys Gly Asn Lys Thr Val Thr Pro Val Ser Pro Leu Gly Lys Lys
            515                 520                 525

Leu Asn Val Thr Thr Ala Trp Lys Ala Gln Asn Pro Val Leu Arg Glu
        530                 535                 540

Val Val Asp Ile Leu Thr Glu Gln Leu Trp Asp Ile Gln Leu Glu Asn
545                 550                 555                 560

Tyr Thr Pro Lys Glu Pro Leu Thr Leu Gln Ala Arg Met Ser Cys Glu
                565                 570                 575

Gln Lys Ala Glu Gly His Ser Ser Gly Ser Trp Gln Phe Ser Phe Asp
            580                 585                 590

Gly Gln Ile Phe Leu Leu Phe Asp Ser Glu Lys Arg Met Trp Thr Thr
        595                 600                 605

Val His Pro Gly Ala Arg Lys Met Lys Glu Lys Trp Glu Asn Asp Lys
                610                 615                 620

Val Val Ala Thr Lys Leu Tyr Leu Trp Ser Met Gly Asp Cys Ile Gly
625                 630                 635                 640

Trp Leu Glu Asp Phe Leu Met Gly Met Asp Ser Thr Leu Glu Pro Ser
                645                 650                 655

<210> SEQ ID NO 99
<211> LENGTH: 171
<212> TYPE: PRT
<213> ORGANISM: Homo sapiens

<400> SEQUENCE: 99

His Ser Leu Arg Tyr Asn Leu Thr Val Leu Ser Gly Asp Gly Ser Val
1               5                   10                  15

Gln Ser Gly Phe Leu Ala Glu Val His Leu Asp Gly Gln Pro Phe Leu
            20                  25                  30

Arg Cys Asp Arg Gln Lys Cys Arg Ala Lys Pro Gln Gly Gln Trp Ala
        35                  40                  45

Glu Asp Val Leu Gly Asn Lys Thr Trp Asp Arg Glu Thr Arg Asp Leu
    50                  55                  60

Thr Gly Asn Gly Lys Asp Leu Arg Met Thr Leu Ala His Ile Lys Asp
65                  70                  75                  80

Gln Lys Glu Gly Leu His Ser Leu Gln Glu Ile Arg Val Cys Glu Ile
                85                  90                  95

His Glu Asp Asn Ser Thr Arg Ser Ser Gln His Phe Tyr Tyr Asp Gly
            100                 105                 110

Glu Leu Phe Leu Ser Gln Asn Leu Glu Thr Glu Glu Trp Thr Met Pro
        115                 120                 125

Gln Ser Ser Arg Ala Gln Thr Leu Ala Met Asn Val Arg Asn Phe Leu
    130                 135                 140

Lys Glu Asp Ala Met Lys Thr Lys Thr His Tyr His Ala Met His Ala
145                 150                 155                 160

Asp Cys Leu Gln Glu Leu Arg Arg Tyr Leu Lys
                165                 170

<210> SEQ ID NO 100
<211> LENGTH: 169
<212> TYPE: PRT
<213> ORGANISM: Homo sapiens

<400> SEQUENCE: 100

His Cys Leu Cys Tyr Asp Phe Ile Ile Thr Pro Lys Ser Arg Pro Glu
```

```
              1               5                  10                 15
            Pro Gln Trp Cys Glu Val Gln Gly Leu Val Asp Glu Arg Pro Phe Leu
                            20                  25                 30

His Tyr Asp Cys Val Asn His Lys Ala Lys Ala Phe Ala Ser Leu Gly
                            35                  40                 45

Lys Lys Val Asn Val Thr Lys Thr Trp Glu Glu Thr Glu Thr Leu
                50                      55                  60

Arg Asp Val Val Asp Phe Leu Lys Gly Gln Leu Leu Asp Ile Gln Val
             65                     70                  75                 80

Glu Asn Leu Ile Pro Ile Glu Pro Leu Thr Leu Gln Ala Arg Met Ser
                                85                  90                 95

Cys Glu His Glu Ala His Gly His Gly Arg Gly Ser Trp Gln Phe Leu
                            100                 105                110

Phe Asn Gly Gln Lys Phe Leu Leu Phe Asp Ser Asn Asn Arg Lys Trp
                            115                 120                125

Thr Ala Leu His Pro Gly Ala Lys Lys Met Thr Glu Lys Trp Glu Lys
                            130                 135                140

Asn Arg Asp Val Thr Met Phe Phe Gln Lys Ile Ser Leu Gly Asp Cys
            145                 150                 155                160

Lys Met Trp Leu Glu Glu Phe Leu Met
                            165
```

<210> SEQ ID NO 101
<211> LENGTH: 169
<212> TYPE: PRT
<213> ORGANISM: Homo sapiens

<400> SEQUENCE: 101

```
            His Ser Leu Cys Tyr Asp Ile Thr Val Ile Pro Lys Phe Arg Pro Gly
             1               5                  10                 15

Pro Arg Trp Cys Ala Val Gln Gly Gln Val Asp Glu Lys Thr Phe Leu
                            20                  25                 30

His Tyr Asp Cys Gly Asn Lys Thr Val Thr Pro Val Ser Pro Leu Gly
                            35                  40                 45

Lys Lys Leu Asn Val Thr Thr Ala Trp Lys Ala Gln Asn Pro Val Leu
                50                      55                  60

Arg Glu Val Val Asp Ile Leu Thr Glu Gln Leu Arg Asp Ile Gln Leu
             65                     70                  75                 80

Glu Asn Tyr Thr Pro Lys Glu Pro Leu Thr Leu Gln Ala Arg Met Ser
                                85                  90                 95

Cys Glu Gln Lys Ala Glu Gly His Ser Ser Gly Ser Trp Gln Phe Ser
                            100                 105                110

Phe Asp Gly Gln Ile Phe Leu Leu Phe Asp Ser Glu Lys Arg Met Trp
                            115                 120                125

Thr Thr Val His Pro Gly Ala Arg Lys Met Lys Glu Lys Trp Glu Asn
                            130                 135                140

Asp Lys Val Val Ala Met Ser Phe His Tyr Phe Ser Met Gly Asp Cys
            145                 150                 155                160

Ile Gly Trp Leu Glu Asp Phe Leu Met
                            165
```

<210> SEQ ID NO 102
<211> LENGTH: 169
<212> TYPE: PRT
<213> ORGANISM: Homo sapiens

```
<400> SEQUENCE: 102

His Ser Leu Trp Tyr Asn Phe Thr Ile Ile His Leu Pro Arg His Gly
1               5                  10                  15

Gln Gln Trp Cys Glu Val Gln Ser Gln Val Asp Gln Lys Asn Phe Leu
            20                  25                  30

Ser Tyr Asp Cys Gly Ser Asp Lys Val Leu Ser Met Gly His Leu Glu
        35                  40                  45

Glu Gln Leu Tyr Ala Thr Asp Ala Trp Gly Lys Gln Leu Glu Met Leu
    50                  55                  60

Arg Glu Val Gly Gln Arg Leu Arg Leu Glu Leu Ala Asp Thr Glu Leu
65                  70                  75                  80

Glu Asp Phe Thr Pro Ser Gly Pro Leu Thr Leu Gln Val Arg Met Ser
                85                  90                  95

Cys Glu Cys Glu Ala Asp Gly Tyr Ile Arg Gly Ser Trp Gln Phe Ser
            100                 105                 110

Phe Asp Gly Arg Lys Phe Leu Leu Phe Asp Ser Asn Asn Arg Lys Trp
        115                 120                 125

Thr Val Val His Ala Gly Ala Arg Arg Met Lys Glu Lys Trp Glu Lys
    130                 135                 140

Asp Ser Gly Leu Thr Thr Phe Phe Lys Met Val Ser Met Arg Asp Cys
145                 150                 155                 160

Lys Ser Trp Leu Arg Asp Phe Leu Met
                165

<210> SEQ ID NO 103
<211> LENGTH: 168
<212> TYPE: PRT
<213> ORGANISM: Homo sapiens

<400> SEQUENCE: 103

His Ser Leu Cys Phe Asn Phe Thr Ile Lys Ser Leu Ser Arg Pro Gly
1               5                  10                  15

Gln Pro Trp Cys Glu Ala Gln Val Phe Leu Asn Lys Asn Leu Phe Leu
            20                  25                  30

Gln Tyr Asn Ser Asp Asn Asn Met Val Lys Pro Leu Gly Leu Leu Gly
        35                  40                  45

Lys Lys Val Tyr Ala Thr Ser Thr Trp Gly Glu Leu Thr Gln Thr Leu
    50                  55                  60

Gly Glu Val Gly Arg Asp Leu Arg Met Leu Leu Cys Asp Ile Lys Pro
65                  70                  75                  80

Gln Ile Lys Thr Ser Asp Pro Ser Thr Leu Gln Val Glu Met Phe Cys
                85                  90                  95

Gln Arg Glu Ala Glu Arg Cys Thr Gly Ala Ser Trp Gln Phe Ala Thr
            100                 105                 110

Asn Gly Glu Lys Ser Leu Leu Phe Asp Ala Met Asn Met Thr Trp Thr
        115                 120                 125

Val Ile Asn His Glu Ala Ser Lys Ile Lys Glu Thr Trp Lys Lys Asp
    130                 135                 140

Arg Gly Leu Glu Lys Tyr Phe Arg Lys Leu Ser Lys Gly Asp Cys Asp
145                 150                 155                 160

His Trp Leu Arg Glu Phe Leu Gly
                165
```

<210> SEQ ID NO 104
<211> LENGTH: 169
<212> TYPE: PRT
<213> ORGANISM: Homo sapiens

<400> SEQUENCE: 104

His Ser Leu Cys Tyr Asp Ile Thr Val Ile Pro Lys Phe Arg Pro Gly
1               5                   10                  15

Pro Arg Trp Cys Ala Val Gln Gly Gln Val Asp Glu Lys Thr Phe Leu
            20                  25                  30

His Tyr Asp Cys Gly Ser Lys Thr Val Thr Pro Val Ser Pro Leu Gly
        35                  40                  45

Lys Lys Leu Asn Val Thr Thr Ala Trp Lys Ala Gln Asn Pro Val Leu
    50                  55                  60

Arg Glu Val Val Asp Ile Leu Thr Glu Gln Leu Leu Asp Ile Gln Leu
65                  70                  75                  80

Glu Asn Tyr Ile Pro Lys Glu Pro Leu Thr Leu Gln Ala Arg Met Ser
                85                  90                  95

Cys Glu Gln Lys Ala Glu Gly His Gly Ser Gly Ser Trp Gln Leu Ser
            100                 105                 110

Phe Asp Gly Gln Ile Phe Leu Leu Phe Asp Ser Glu Asn Arg Met Trp
        115                 120                 125

Thr Thr Val His Pro Gly Ala Arg Lys Met Lys Glu Lys Trp Glu Asn
    130                 135                 140

Asp Lys Asp Met Thr Met Ser Phe His Tyr Ile Ser Met Gly Asp Cys
145                 150                 155                 160

Thr Gly Trp Leu Glu Asp Phe Leu Met
                165

<210> SEQ ID NO 105
<211> LENGTH: 169
<212> TYPE: PRT
<213> ORGANISM: Homo sapiens

<400> SEQUENCE: 105

His Ser Leu Cys Tyr Asp Ile Thr Val Ile Pro Lys Phe Arg Pro Gly
1               5                   10                  15

Pro Arg Trp Cys Ala Val Gln Gly Gln Val Asp Glu Lys Thr Phe Leu
            20                  25                  30

His Tyr Asp Cys Gly Asn Lys Thr Val Thr Pro Val Ser Pro Leu Gly
        35                  40                  45

Lys Lys Leu Asn Val Thr Thr Ala Trp Lys Ala Gln Asn Pro Val Leu
    50                  55                  60

Arg Glu Val Val Asp Ile Leu Thr Glu Gln Leu Leu Asp Ile Gln Leu
65                  70                  75                  80

Glu Asn Tyr Thr Pro Lys Glu Pro Leu Thr Leu Gln Ala Arg Met Ser
                85                  90                  95

Cys Glu Gln Lys Ala Glu Gly His Ser Ser Gly Ser Trp Gln Phe Ser
            100                 105                 110

Ile Asp Gly Gln Thr Phe Leu Leu Phe Asp Ser Glu Lys Arg Met Trp
        115                 120                 125

Thr Thr Val His Pro Gly Ala Arg Lys Met Lys Glu Lys Trp Glu Asn
    130                 135                 140

```
-continued

Asp Lys Asp Val Ala Met Ser Phe His Tyr Ile Ser Met Gly Asp Cys
145                 150                 155                 160

Ile Gly Trp Leu Glu Asp Phe Leu Met
                165
```

US 10,259,858 B2

INSERTABLE VARIABLE FRAGMENTS OF ANTIBODIES AND MODIFIED α1-α2 DOMAINS OF NKG2D LIGANDS, AND NON-NATURAL NKG2D LIGANDS THAT BIND NON-NATURAL NKG2D RECEPTORS

BACKGROUND OF THE INVENTION

Field of the Invention

This application relates generally to the production of polypeptides having specific antigen-binding properties of Fv domains, for example, insertable variable fragments of antibodies, and modified α1-α2 domains of NKG2D ligands.

Background Information

An antibody (Ab), FIG. 1, also known as an immunoglobulin (Ig), in many mammals including humans is a large, Y-shape protein used by the immune system to identify and neutralize foreign objects such as bacteria and viruses (Charles Janeway (2001). *Immunobiology*. (5th ed.), Chapter 3. Garland Publishing. ISBN 0-8153-3642-X. (electronic full text via NCBI Bookshelf). The antibody recognizes a unique part of the foreign target, called an antigen. Each tip of the two arms of the "Y" of an antibody contains an antigen binding site, or a paratope, (a structure analogous to a lock) that is specific for one particular epitope (similarly analogous to a key) of an antigen, allowing these two structures to bind together with precision. Using this binding mechanism, an antibody can tag a microbe or an infected cell for attack by other parts of the immune system or can neutralize its target directly, for example, by blocking a part of a microbe that is essential for its invasion and survival. The production of antibodies is the main function of the humoral, or "adaptive", immune system. Antibodies are secreted by plasma cells. Antibodies in nature can occur in two physical forms, a soluble form that is secreted from the cell, and a membrane-bound form that is attached to the surface of a B cell via the "stem" of the Y.

Antibodies are glycoproteins belonging to the immunoglobulin superfamily and are typically made of basic structural units—each with two large heavy chains and two small light chains. There are several different types of antibody heavy chains, and several different kinds of antibodies, which are grouped into different isotypes based on which heavy chain they possess. Five different antibody isotypes are known in mammals (Market E, Papavasiliou F N (October 2003). "V(D)J recombination and the evolution of the adaptive immune system". *PLoS Biol.* 1 (1): E16. doi:10.1371/journal.pbio.0000016. PMC 212695. PMID 14551913). Although the general structure of all antibodies is very similar, a small region at the tip of each arm of the Y-shaped protein is extremely variable, allowing millions of antibodies with slightly different tip structures, or antigen-binding sites, to exist. This region is known as the hypervariable or variable region. Each of these natural variants can bind to a different antigen. This enormous diversity of antibodies allows the immune system to adapt and recognize an equally wide variety of antigens (Hozumi N, Tonegawa S (1976). "Evidence for somatic rearrangement of immunoglobulin genes coding for variable and constant regions". *Proc. Natl. Acad. Sci. U.S.A.* 73 (10): 3628-3632. doi:10.1073/pnas.73.10.3628. PMC 431171. PMID 824647.)

The natural "Y"-shaped Ig molecule consists of four polypeptide chains; two identical heavy chains and two identical light chains connected by disulfide bonds, FIG. 1. Each heavy chain has two major regions, the constant region (CH) and the variable region (VH). The constant region is essentially identical in all antibodies of the same isotype, but differs in antibodies of different isotypes. A light chain also has two successive domains: a smaller constant region (CL) and the variable region (VL) (Woof J, Burton D (2004). "Human antibody-Fc receptor interactions illuminated by crystal structures." *Nat Rev Immunol* 4 (2): 89-99. doi:10.1038/nri1266. PMID 15040582).

Some parts of an antibody have the same functions. Each of the two arms of the Y, for example, contains the sites that can bind to antigens and, therefore, recognize specific foreign objects. This region of the antibody is called the Fv (fragment, variable) region. It is composed of one variable domain from the heavy chain ($V_H$) and one variable region from the light chain ($V_L$) of the antibody (Hochman J, Inbar D, Givol D (1973). An active antibody fragment (Fv) composed of the variable portions of heavy and light chains. *Biochemistry* 12 (6): 1130-1135. doi:10.1021/bi00730a018. PMID 4569769). The paratope is shaped at one end of the Fv and is the region for binding to antigens. It is comprised of variable loops of β-strands, three each on the $V_L$ and on the $V_H$ and is responsible for binding to the antigen, FIG. 2. These 6 loops are referred to as the complementarity determining regions (CDRs) (North B, Lehmann A, Dunbrack R L (2010). "A new clustering of antibody CDR loop conformations". *J Mol Biol* 406 (2): 228-256. doi:10.1016/j.jmb.2010.10.030. PMC 3065967. PMID 21035459).

Useful polypeptides that possess specific antigen binding function can be derived from the CDRs of the variable regions of antibodies. These two antibody variable domains, one of the light chain (VL) and one from the heavy chain ($V_H$), each with 3 CDRs can be fused in tandem, in either order, using a single, short linker peptide of 10 to about 25 amino acids to create a linear single-chain variable fragment (scFv) polypeptide comprising one each of heavy and light chain variable domains, FIG. 3 (Bird, R. E., Hardman, K. D., Jacobson, J. W., Johnson, S., Kaufman, B. M., Lee, S. M., Lee, T., Pope, S. H., Riordan, G. S., and Whitlow, M. (1988) Single-chain antigen-binding proteins, *Science* 242, 423-426; Huston, J. S., Levinson, D, Mudgett-Hunter, M, Tai, M-S, Novotny, J, Margolies, M. N., Ridge, R., Bruccoleri, R E., Haber, E., Crea, R., and Opperman, H. (1988). Protein engineering of antibody binding sites: Recovery of specific activity in an anti-digoxin single-chain Fv analogue produced in *Escherichia coli*. PNAS 85: 5879-5883).

The linker is usually rich in glycine for flexibility, as well as serine, threonine, or charged amino acids for solubility, and can either connect the N-terminus of the $V_H$ with the C-terminus of the $V_L$, or vice versa. This protein retains the specificity of the original immunoglobulin, despite removal of the constant regions and the introduction of the single linker. This format enables one ordinarily skilled in the art of recombinant DNA technology to genetically fuse the linear scFv to the N- or C-terminus of a parent protein in order to impart to the parent protein the antigen binding properties of the scFv. There are numerous other proposed or created arrangements of polyvalent and tandem scFv regions, but importantly as described below, all have at least two spatially distant termini, FIG. 4 (Le Gall, F.; Kipriyanov, S M; Moldenhauer, G; Little, M (1999). "Di-, tri- and tetrameric single chain Fv antibody fragments against human CD19: effect of valency on cell binding". *FEBS Letters* 453 (1): 164-168. doi:10.1016/S0014-5793(99)00713-9. PMID 10403395).

SUMMARY OF THE INVENTION

The present disclosure relates to modified α1-α2 domains of NKG2D ligands attached to polypeptides, in some embodiments antibodies or fragments of antibodies. In some aspects, the present disclosure relates to antigen-binding peptides derived from light and heavy chain antibody variable domains, which contain two linker regions and a split variable domain.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4. Polyvalent single-chain variable fragments (scFv's). Structure of divalent (top) and trivalent (bottom) scFvs, tandem (left) and di-/trimerization format (right). Note that each has 2 or more spatially distant free termini.

FIG. 19. Phage ELISA titrations of ULBP variants binding to NKG2D. Panel (A) depicts experiments in which ULBP2 variants displayed on phage were titrated against NKG2D and relative binding affinities were measured relative to native ULBP2 (WT, black circles). Panel (B) depicts experiments in which ULBP3 variants displayed on phage were titrated against NKG2D and relative binding affinities were measured relative to native ULBP3 (WT, black circles).

FIG. 20. Protein sequence alignment of α1-α2 domains from MICA and ULBPs (MICA, SEQ ID NO: 99; ULBP4, SEQ ID NO:103; ULBP3, SEQ ID NO:102; ULBP1, SEQ ID NO:100; ULBP5, SEQ ID NO:104; ULBP2, SEQ ID NO:101; ULBP6, SEQ ID NO:105). Amino acids highlighted in grey were selected for NNK mutagenesis in ULBP2 (60 amino acids) and ULBP3 (36 amino acids). Residues highlighted in black were identified as key positions for selected and identified as mutations that modulate binding affinity to NKG2D (Tables 6 and 7).

DETAILED DESCRIPTION OF THE INVENTION

Figure 1:
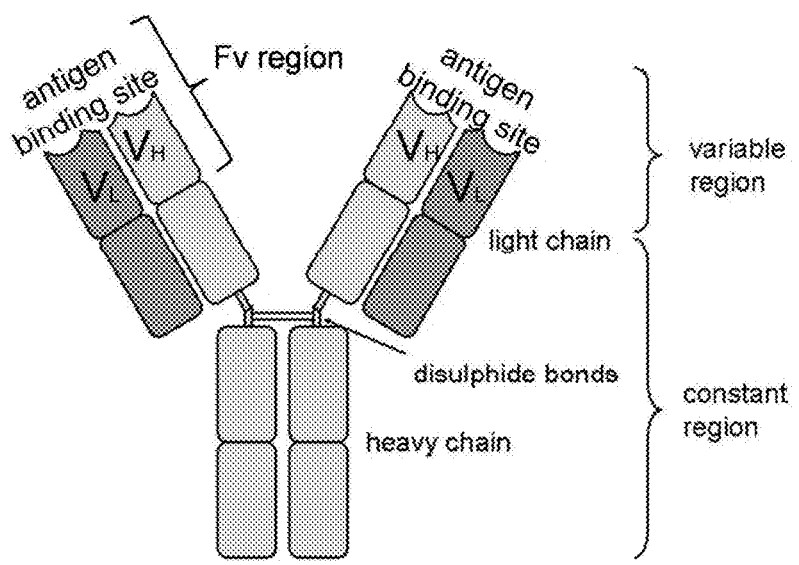
FIG. 1. A cartoon of a typical mammalian antibody showing its Y-shaped structure and structural components.
Figure 2:
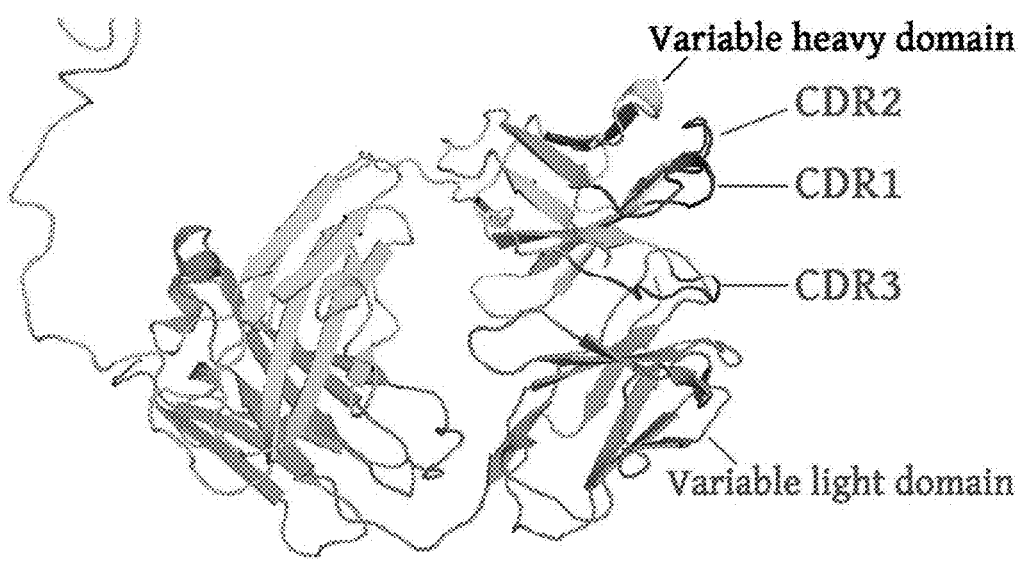
FIG. 2. A cartoon of the structure of an Fv region of a natural mammalian antibody showing the 3 labeled (Complementarity Determining Regions) CDRs of the $V_H$ and the 3 unlabeled loops of the $V_L$ CDRs, which form the paratope or antigen binding site.
Figure 3:
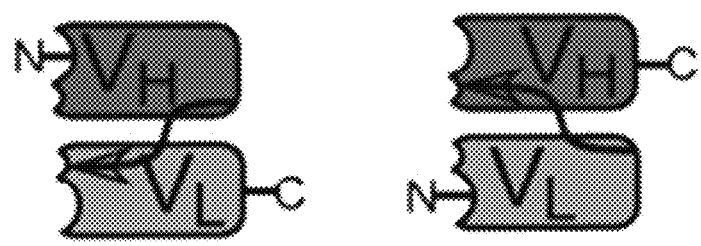
FIG. 3. A cartoon of the two possible structures of a single-chain variable fragment (scFv), with the antigen binding sites including the N-termini on the left and the C-termini on the right. The single linker region, or linker peptide, in each scFv is shown as an arrow.

In some aspects, the present invention relates to insertable variable fragment (iFv) peptides. Because the C-terminus and N-terminus of scFv molecules including polyvalent scFv structures are far apart spatially, scFv structures cannot be inserted into a loop region embedded within a protein fold of a parent or recipient protein without disrupting or destabilizing its fold(s) and/or without disrupting the Fv framework required to properly position the CDRs or hypervariable regions to retain their antigen-binding properties.

To insert the variable fragment of an antibody containing up to 6 CDRs into one or more loop regions of a nascent parent protein molecule without disrupting structural folds of the variable fragment or of the parent protein, we invented a new class of antigen-binding peptides derived from the light and heavy chain antibody variable domains. The new structures contained two linker regions, rather than the traditional single linker of scFv structures, plus a split variable domain. Conceptually the canonical termini of the variable light (VL) and heavy (VH) domains were fused into a continuous or "circular" peptide. That circular peptide structure containing all 6 CDRs of the Fv can then conceptually be split at one of several possible novel sites to create an insertable Fv (iFv). The non-natural split site can be created within either the light or the heavy chain variable domain at or near the apex or turn of a loop to create new, unique N- and C-termini spatially positioned proximal to each other, preferably within 0.5 to 1.5 nm, so as to be insertable into loops of other (parent or recipient) proteins or polypeptides without disrupting the structure, stability, or desirable function. This new class of peptides is called an insertable variable fragment (iFv). The binding or targeting specificity conveyed by an iFv to a recipient molecule can be changed by inserting into the recipient another or different iFV based on a different antibody or scFv or by replacing 1 or more of the CDRs of an existing insertable iFv.

The insertion of one or more iFv polypeptides exhibiting specific antigen-binding properties of Fv domains into other proteins and thereby imparting novel binding properties will have multiple utilities. Such uses include but are not limited to enabling the parent protein to bind the specific antigen, target the antigen, detect the presence of antigen, remove the antigen, contact or draw near the antigen, to deliver a payload to the antigen or antigen-expressing cell, recruit the antigen, and image the presence of the antigen. A payload could be conjugated directly to one or both the amino-terminus and carboxy-terminus of an iFv or indirectly to an iFv via a parent protein or peptide. Examples of payloads include but are not limited to a chromophore, a fluorophore, a pharmacophore, an atom, a heavy or radioactive isotope, an imaging agent, a chemotherapeutic agent, or a toxin. A payloaded iFv can be used to locate or identify the presence of a target molecule to which the iFv specifically binds and as such can serve as in vitro or in vivo imaging agents or diagnostic agents that are small and stable. In addition, to one or both the amino-terminus and carboxy-terminus of an iFv peptide a chemotherapeutic agent or toxic molecule can be conjugated in order to create an iFv-drug conjugate, for example, as treatment for a malignancy or infection. A single payload may be conjugated to both the amino-terminus and the carboxy-terminus of an iFv peptide so as to span or connect the two termini; such spanning may further stabilize the iFv by blocking the termini from exopeptidase degradation or protecting the iFv from denaturation or unfolding.

Examples of parent or recipient proteins or polypeptides that are candidates for insertions of iFv peptides include but are not limited to antibodies, proteins comprised of Ig folds or Ig domains, globulins, albumens, fibronectins and fibronectin domains, integrins, fluorescent proteins, enzymes, outer membrane proteins, receptor proteins, T-cell receptors, chimeric antigen receptors, viral antigens, virus capsids, viral ligands for cell receptors, high molecular weight bacteriocins, histones, hormones, knottins, cyclic peptides or polypeptides, major histocompatibility (MHC) family proteins, MIC proteins, lectins, and ligands for lectins. It is also possible to insert iFv structures into non-protein recipient molecules such a polysaccharides, dendrimers, polyglycols, peptidoglycans, antibiotics, and polyketides.

Natural killer (NK) cells and certain (CD8+αβ and γδ) T-cells of the immunity system have important roles in humans and other mammals as first-line, innate defense against neoplastic and virus-infected cells (Cerwenka, A., and L. L. Lanier. 2001. NK cells, viruses and cancer. Nat. Rev. Immunol. 1:41-49). NK cells and certain T-cells exhibit on their surfaces NKG2D, a prominent, homodimeric, surface immunoreceptor responsible for recognizing a target cell and activating the innate defense against the pathologic cell (Lanier, L L, 1998. NK cell receptors. Ann. Rev. Immunol. 16: 359-393; Houchins J P et al. 1991. DNA sequence analysis of NKG2, a family of related cDNA clones encoding type II integral membrane proteins on human NK cells. J. Exp. Med. 173: 1017-1020; Bauer, S et al., 1999. Activation of NK cells and T cells by NKG2D, a receptor for stress-inducible MICA. Science 285: 727-730). The human NKG2D molecule possesses a C-type lectin-like extracellular domain that binds to its cognate ligands, the 84% sequence identical or homologous, monomeric MICA and MICB, polymorphic analogs of the Major Histocompatibility Complex (MHC) Class I chain-related glycoproteins (MIC) (Weis et al. 1998. The C-type lectin superfamily of the immune system. Immunol. Rev. 163: 19-34; Bahram et al. 1994. A second lineage of mammalian MHC class I genes. PNAS 91:6259-6263; Bahram et al. 1996a. Nucleotide sequence of the human MHC class I MICA gene. Immunogenetics 44: 80-81; Bahram and Spies T A. 1996. Nucleotide sequence of human MHC class I MICB cDNA. Immunogenetics 43: 230-233). Non-pathologic expression of MICA and MICB is restricted to intestinal epithelium, keratinocytes, endothelial cells and monocytes, but aberrant surface expression of these MIC proteins occurs in response to many types of cellular stress such as proliferation, oxidation and heat shock and marks the cell as pathologic (Groh et al. 1996. Cell stress-regulated human MHC class I gene expressed in GI epithelium. PNAS 93: 12445-12450; Groh et al. 1998. Recognition of stress-induced MHC molecules by intestinal γδT cells. Science 279: 1737-1740; Zwirner et al. 1999. Differential expression of MICA by endothelial cells, fibroblasts, keratinocytes and monocytes. Human Immunol. 60: 323-330). Pathologic expression of MIC proteins also seems involved in some autoimmune diseases (Ravetch, J V and Lanier L L. 2000. Immune Inhibitory Receptors. Science 290: 84-89; Burgess, S J. 2008. Immunol. Res. 40: 18-34). The differential regulation of NKG2D ligands, such as the polymorphic MICA and MICB, is important to provide the immunity system with a means to identify and respond to a broad range of emergency cues while still protecting healthy cells from unwanted attack (Stephens H A, (2001) MICA and MICB genes: can the enigma of their polymorphism be resolved? Trends Immunol. 22: 378-85; Spies, T. 2008. Regulation of NKG2D ligands: a purposeful but delicate affair. Nature Immunol. 9: 1013-1015).

Viral infection is a common inducer of MIC protein expression and identifies the viral-infected cell for NK or T-cell attack (Groh et al. 1998; Groh et al. 2001. Co-stimulation of CD8+ αβT-cells by NKG2D via engagement by MIC induced on virus-infected cells. Nat. Immunol. 2: 255-260; Cerwenka, A., and L. L. Lanier. 2001). In fact, to avoid such an attack on its host cell, cytomegalovirus and other viruses have evolved mechanisms that prevent the expression of MIC proteins on the surface of the cell they infect in order to escape the wrath of the innate immunity system (Lodoen, M., K. Ogasawara, J. A. Hamerman, H. Arase, J. P. Houchins, E. S. Mocarski, and L. L. Lanier. 2003. NKG2D-mediated NK cell protection against cytomegalovirus is impaired by gp40 modulation of RAE-1 molecules. J. Exp. Med. 197:1245-1253; Stern-Ginossar et al., (2007) Host immune system gene targeting by viral miRNA. Science 317: 376-381; Stern-Ginossar et al., (2008) Human microRNAs regulate stress-induced immune responses mediated by the receptor NKG2D. Nature Immunology 9: 1065-73; Slavuljica, I A Busche, M Babic, M Mitrovic, I Gašparovic, Đ Cekinovic, E Markova Car, E P Pugel, A Cikovic, V J Lisnic, W J Britt, U Koszinowski, M Messerle, A Krmpotic and S Jonjic. 2010. Recombinant mouse cytomegalovirus expressing a ligand for the NKG2D receptor is attenuated and has improved vaccine properties. J. Clin. Invest. 120: 4532-4545).

In spite of their stress, many malignant cells, such as those of lung cancer and glioblastoma brain cancer, also avoid the expression of MIC proteins and as a result may be particularly aggressive as they too escape the innate immunity system (Busche, A et al. 2006, NK cell mediated rejection of experimental human lung cancer by genetic over expression of MHC class I chain-related gene A. Human Gene Therapy 17: 135-146; Doubrovina, E S, M M Doubrovin, E Vider, R B Sisson, R J O'Reilly, B Dupont, and Y M Vyas, 2003. Evasion from NK Cell Immunity by MHC Class I Chain-Related Molecules Expressing Colon Adenocarcinoma (2003) J. Immunology 6891-99; Friese, M. et al. 2003. MICA/NKG2D-mediated immunogene therapy of experimental gliomas. Cancer Research 63: 8996-9006; Fuertes, M B, M V Girart, L L Molinero, C I Domaica, L E Rossi, M M Barrio, J Mordoh, G A Rabinovich and N W Zwirner. (2008) Intracellular Retention of the NKG2D Ligand MHC Class I Chain-Related Gene A in Human Melanomas Confers Immune Privilege and Prevents NK Cell-Mediated Cytotoxicity. J. Immunology, 180: 4606-4614).

The high resolution structure of human MICA bound to NKG2D has been solved and demonstrates that the α3 domain of MICA has no direct interaction with the NKG2D (Li et al. 2001. Complex structure of the activating immunoreceptor NKG2D and its MHC class I-like ligand MICA. Nature Immunol. 2: 443-451; Protein Data Bank accession code 1HYR). The α3 domain of MICA, like that of MICB, is connected to the α1-α2 platform domain by a short, flexible linker peptide, and itself is positioned naturally as "spacer" between the platform and the surface of the MIC expressing cell. The 3-dimensional structures of the human MICA and MICB α3 domains are nearly identical (root-mean square distance <1 Å on 94 C-αα's) and functionally interchangeable (Holmes et al. 2001. Structural Studies of Allelic Diversity of the MHC Class I Homolog MICB, a Stress-Inducible Ligand for the Activating Immunoreceptor NKG2D. J Immunol. 169: 1395-1400).

Certain non-natural α1-α2 domains of NKG2D ligands modified to bind natural human NKG2D receptors with higher affinities than do natural α1-α2 domains have been described (Candice S. E. Lengyel, Lindsey J. Willis, Patrick Mann, David Baker, Tanja Kortemme, Roland K. Strong and Benjamin J. McFarland. Mutations Designed to Destabilize the Receptor-Bound Conformation Increase MICA-NKG2D Association Rate and Affinity. Journal of Biological Chemistry Vol. 282, no. 42, pp. 30658-30666, 2007; Samuel H. Henager, Melissa A. Hale, Nicholas J. Maurice, Erin C. Dunnington, Carter J. Swanson, Megan J. Peterson, Joseph J. Ban, David J. Culpepper, Luke D. Davies, Lisa K. Sanders, and Benjamin J. McFarland. Combining different design strategies for rational affinity maturation of the MICA-NKG2D interface. Protein Science 2012 VOL 21:1396-1402. Herein we describe non-natural α1-α2 domains of NKG2D ligands that have been modified to bind non-natural NKG2D receptors, themselves mutated at sites which consequentially result in compromised or loss of binding to natural α1-α2 domains of NKG2D ligands (David J. Culpepper, Michael K. Maddox, Andrew B. Caldwell, and Benjamin J. McFarland. Systematic mutation and thermodynamic analysis of central tyrosine pairs in polyspecific NKG2D receptor interactions. Mol Immunol. 2011 January; 48(4): 516-523; USPTO application Ser. No. 14/562,534; USPTO provisional application 62/088,456)). This invention creates bispecific molecules comprised of the specifically modified non-natural α1-α2 domains and specific targeting heterologous molecules, including but not limited to heterologous peptides or polypeptides, that bind Chimeric Antigen Receptors (CARs) wherein the receptor of the CAR is comprised of a non-natural NKG2D receptor ectodomain that binds the modified α1-α2 domains with greater affinity than it does natural α1-α2 domains. Genetically engineered cells of the immunity system comprised of such CARs can then overcome many of the disadvantages, including known severe systemic toxicities and antigen escape, of current CAR-T and CAR-NK cell therapeutics as described below (Kalos M, Levine, B L, Porter, D L, Katz, S, Grupp, S A, Bagg, A and June, C. T Cells with chimeric antigen receptors have potent antitumor effects and can establish memory in patients with advanced leukemia. Sci Transl Med 2011;3: 95ra73; Morgan R A, Yang J C, Kitano M, Dudley M E, Laurencot C M, Rosenberg S A. Case report of a serious adverse event following the administration of T cells transduced with a chimeric antigen receptor recognizing ERBB2. Mol Ther 2010, 18:843-851; Gill and June 2015).

T-cells and NK-cells can be modified using gene transfer technologies to directly and stably express on their surface binding domains of an antibody that confer novel antigen specificities (Saar Gill & Carl H. June. Going viral: chimeric antigen receptor T-cell therapy for hematological malignancies. Immunological Reviews 2015. Vol. 263: 68-89; Wolfgang Glienke, Ruth Esser, Christoph Priesner, Julia D. Suerth, Axel Schambach, Winfried S. Wels, Manuel Grez, Stephan Kloess, Lubomir Arseniev and Ulrike Koehl. 2015. Advantages and applications of CAR-expressing natural killer cells. Front. Pharmacol. doi: 10.3389/fphar.2015.00021). CAR-T cells are applications of this approach that combines an antigen recognition domain of a specific antibody with an intracellular domain of the CD3-ζ chain, which is the primary transmitter of signals from endogenous T-Cell Receptors (TCRs), into a single chimeric protein along with a co-stimulatory molecule such as CD27, CD28, ICOS, 4-1BB, or OX40, FIG. 16. CARs so constructed can trigger T cell activation upon binding the targeted antigen in a manner similar to an endogenous T cell receptor but independent of the major histocompatibility complex (MHC).

As used herein, a "soluble MIC protein", "soluble MICA" and "soluble MICB" refer to a MIC protein containing the α1, α2, and α3 domains of the MIC protein but without the transmembrane or intracellular domains. The NKG2D ligands, ULBP1-6, do not naturally possess an α3 domain (Cerwenka A, Lanier L L. 2004. NKG2D ligands: unconventional MHC class I-like molecules exploited by viruses and cancer. *Tissue Antigens* 61 (5): 335-43. doi:10.1034/j.1399-0039.2003.00070.x. PMID 12753652). An "α1-α2 domain" of an NKG2D ligand refers to the protein domain of the ligand that binds an NKG2D receptor.

In some embodiments, the α1-α2 domains of the non-natural NKG2D ligand proteins of the invention are at least 80% identical or homologous to the native or natural α1-α2 domain of an NKG2D ligand, SEQ ID NOs: 36-54. In other embodiments, the modified α1-α2 domain is 85% identical to a native or natural α1-α2 domain of an NKG2D ligand. In yet other embodiments, the modified α1-α2 domain is 90% identical to a native or natural α1-α2 domain of a natural NKG2D ligand protein and binds non-natural NKG2D.

The α1-α2 platform domain of a soluble MIC protein is tethered to the α3 domain and is diffusible in the intercellular or intravascular space of the mammal. Preferably the α1-α2 platform domains of the non-natural MIC proteins of the invention are at least 80% identical or homologous to a native or natural α1-α2 domain of a human MICA or MICB protein and bind NKG2D. In some embodiments, the α1-α2 platform domain is 85% identical to a native or natural α1-α2 platform domain of a human MICA or MICB protein and binds NKG2D. In other embodiments, the α1-α2 platform domain is 90%, 95%, 96%, 97%, 98%, or 99% identical to a native or natural α1-α2 platform domain of a human MICA or MICB protein and binds NKG2D.

In some embodiments, a heterologous peptide tag may be fused to the N-terminus or C-terminus of an α1-α2 domain or a soluble MIC protein to aid in the purification of the soluble MIC protein. Tag sequences include peptides such as a poly-histidine, myc-peptide or a FLAG tag. Such tags may be removed after isolation of the MIC molecule by methods known to one skilled in the art.

In other embodiments of the invention, specific mutations in α1-α2 domains of NKG2D ligands can be made to create non-natural α1-α2 domains that bind non-natural NKG2D receptors, themselves engineered so as to have reduced affinity for natural NKG2D ligands. This can be done, for example, through genetic engineering. A non-natural NKG2D receptor so modified can be used to create on the surface of NK- or T-cells of the immune system an NKG2D-based Chimeric Antigen Receptor (CAR) that can preferentially bind to and be activated by molecules comprised of the invented non-natural α1-α2 domains. These pairs of non-natural NKG2D receptors and their invented cognate non-natural NKG2D ligands will provide important safety, efficacy, and manufacturing advantages for treating cancer and viral infections as compared to the current CAR-T cells and CAR-NK cells, as described below.

Engineering T cells with CARs has emerged as a promising approach to adoptive T cell therapy for cancer, and CARs targeting many different molecules have been tested in CAR-T cells as therapeutics for malignancies (Porter D L, Levine B L, Kalos M, Bagg A, June C H. Chimeric antigen receptor-modified T cells in chronic lymphoid leukemia. N Engl J Med. 365:725-733.). While remarkable clinical efficacy has been observed in hundreds of patients receiving adoptive transfer of T cells expressing CD19-specific chimeric antigen receptors, the processes of custom engineering a CAR to target a specific antigen, isolating autologous T-cells from the patient, genetically engineering the autologous T-cells to express the personalized CAR, expanding the modified cells in vitro, and controlling the quality their production have all been onerous and expensive. Currently this is feasible only in the context of large academic centers with extensive expertise and resources (Gill & June, 2015).

Once the autologous CAR-T cells are infused back into the donor patient, their expansion in vivo cannot be controlled—"living therapy", and there is not a dose-response relationship with efficacy (Gill & June, 2015). Furthermore, tumor escape from the CAR T-cell can occur through antigen loss escape (Stephan A. Grupp, M.D., Ph.D., Michael Kalos, Ph.D., David Barrett, M.D., Ph.D., Richard Aplenc, M.D., Ph.D., David L. Porter, M.D., Susan R. Rheingold, M.D., David T. Teachey, M.D., Anne Chew, Ph.D., Bernd Hauck, Ph.D., J. Fraser Wright, Ph.D., Michael C. Milone, M.D., Ph.D., Bruce L. Levine, Ph.D., and Carl H. June, M.D. Chimeric Antigen Receptor-Modified T Cells for Acute Lymphoid Leukemia. N Engl J Med 2013;368:1509-1518), and this escape pathway can most readily be addressed by sequential therapy with a differently targeted CAR-T cell or by an initial infusion of a T-cell product that contains CARs of two or more specificities, further complicating the manufacturing processes and quality control.

In addition to CAR-T cells targeting tumors with single chain antibody binding domains (scFv), CAR-T cells that employ the ligand-binding domain of the NKG2D receptor have been studied in animals and recently in humans (Sentman C L, Meehan K R. NKG2D CARs as cell therapy for cancer. Cancer J. 2014 March-April;20(2):156-9. doi: 10.1097/PPO.0000000000000029; Manfred Lehner, Gabriel Götz, Julia Proff, Niels Schaft, Jan Dörrie, Florian Full, Armin Ensser, Yves A. Muller, Adelheid Cerwenka, Hinrich Abken, Ornella Parolini, Peter F. Ambros, Heinrich Kovar, Wolfgang Holter. Redirecting T Cells to Ewing's Sarcoma Family of Tumors by a Chimeric NKG2D Receptor Expressed by Lentiviral Transduction or mRNA Transfection Research Article | published 15 Feb. 2012 | PLOS ONE 10.1371/journal.pone.0031210; www.clinicaltrials.gov NCT02203825). Since NKG2D ligand expression is increased on the surface of stressed cells, such as tumor cells, this family of natural NKG2D ligands is of significant interest as targets for cancer immunotherapies (Spear P, Wu M R, Sentman M L, Sentman C L. NKG2D ligands as therapeutic targets. Cancer Immun. 2013 May 1;13:8.; Song D G, Ye Q, Santoro S, Fang C, Best A, Powell D J Jr., Chimeric NKG2D CAR-expressing T cell-mediated attack of human ovarian cancer is enhanced by histone deacetylase inhibition. Hum Gene Ther. 2013 March;24(3):295-305). One NKG2D CAR was a fusion of the full-length NKG2D receptor and CD3ζ (NKG2Dζ); another was with only the ectodomain of NKG2D fused in opposite orientation to a second-generation CAR scaffold composed of transmembrane and intracellular domains from CD28 and the signaling domain of CD3ζ (NKG2D28ζ). Since activation of NKG2D is dependent upon the presence of DAP10, a CAR-T cell was also constructed wherein DAP10 was co-expressed with NKG2Dζ (NKG2Dζ10). T cells expressing any of the above NKG2D CARs produced IFNγ and TNFα in response to NKG2D ligand stimulation and in vitro efficiently killed tumor targets expressing NKG2D ligands (Heather VanSeggelen, Joanne A. Hammill, Anna Dvorkin-Gheva, Daniela G. M. Tantalo, Jacek M. Kwiecien, Galina F. Denisova, Brian Rabinovich, Yonghong Wan, Jonathan L. Bramson, T cells engineered with chimeric antigen receptors targeting NKG2D ligands display lethal toxicity in mice, *Molecular Therapy* accepted article preview online 30 Jun. 2015; doi:10.1038/mt.2015.119). The cytotoxic potential of NK cells against a wide spectrum of tumor subtypes could also be markedly enhanced by expression of a CAR based on NKG2D-DAP10-CD3ζ (Yu-Hsiang Chang, John Connolly, Noriko Shimasaki, Kousaku Mimura, Koji Kono, and Dario Campana. Chimeric Receptor with NKG2D Specificity Enhances Natural Killer Cell Activation and Killing of Tumor Cells. Cancer Res; 73(6) Mar. 15, 2013).

However, following infusion into syngeneic murine hosts, significant toxicity occurred with these CAR-T constructs that bind and are activated by natural ligands of the natural NKG2D receptor. Signs of toxicity, including poor body condition, hunched posture, labored breathing, and decreased core body temperature were observed in tumor-bearing and tumor-free mice treated with NKG2D-based CAR-T cells as compared to untreated control mice. The severity of NKG2D CAR-T cell toxicity varied, with NKG2Dζ10 being severely toxic, NKG2D28ζ showing intermediate toxicity, and NKG2Dζ being tolerable. Clinical symptoms of toxicity and mortality rates were exacerbated when mice received chemotherapy prior to adoptive transfer of T cells expressing any of the NKG2D CARs (VanSeggelen et al. 2015). Chemotherapy and radiation are known to induce NKG2D ligands on otherwise healthy tissues (Xiulong Xu, Geetha S Rao, Veronika Groh, Thomas Spies, Paolo Gattuso, Howard L Kaufman, Janet Plate and Richard A Prinz. Major histocompatibility complex class I-related chain A/B (MICA/B) expression in tumor tissue and serum of pancreatic cancer: Role of uric acid accumulation in gemcitabine-induced MICA/B expression. *BMC Cancer* 2011, 11:194 doi:10.1186/1471-2407-11-194; Gannagé M, Buzyn A, Bogiatzi S I, Lambert M, Soumelis V, Dal Cortivo L, Cavazzana-Calvo M, Brousse N, Caillat-Zucman Induction of NKG2D ligands by gamma radiation and tumor necrosis factor-alpha may participate in the tissue damage during acute graft-versus-host disease. Transplantation. 2008 Mar. 27;85(6):911-5. doi: 10.1097/TP.0b013e31816691ef.). Further characterization revealed that the toxicity coincided with a systemic cytokine storm and lethal levels of inflammation within the lungs. These data warn that extreme caution must be taken when using natural NKG2D ligands for targeted immunotherapy and demonstrate that enhancing T cell expression of strongly activating CARs can be detrimental in vivo (VanSeggelen et al. 2015).

CAR-T or CAR-NK cells comprised of ectodomains of non-natural NKG2D receptors that do not or only poorly bind natural NKG2D ligands will not be subject to the above form of activation and thus will not be toxigenic as a cell expressing CAR based on a natural NKG2D receptor. Furthermore, ectodomains of non-natural NKG2D receptors on cells will not be subject to down-regulation by natural NKG2D ligands in a soluble format or on Myeloid Derived Suppressor Cells (MDSC) (Deng W, Gowen B G, Zhang L, Wang L, Lau S, Iannello A, Xu J, Rovis T L, Xiong N, Raulet D H, 2015. Antitumor immunity. A shed NKG2D ligand that promotes natural killer cell activation and tumor rejection. Science. 2015 Apr. 3;348(6230):136-9. doi: 10.1126/science.1258867. Epub 2015 Mar. 5). However, when such CAR cells bearing ectodomains of non-natural NKG2D receptors are engaged by bispecific molecules with the cognate non-natural α1-α2 domains of the instant invention and its heterologous targeting motif which has found and bound its intended target, the CAR will be activated and the CAR-cell's effector functions expressed.

Because the CAR-T or CAR-NK cells comprised of non-natural NKG2D receptor ectodomains are not activated except in the presence of an engaged bispecific molecule comprised of a cognate non-natural α1-α2 domains, their activation can be controlled by the administered bispecific molecules, which as biopharmaceuticals will exhibit pharmacokinetics and pharmacodynamics well known in the field. In the event that an adverse event develops, the physician can simply modify the dosing regimen of the administered bispecific molecule rather than having to deploy an induced suicide mechanism to destroy the infused CAR cells as currently done (Monica Casucci and Attilio Bondanza. Suicide Gene Therapy to Increase the Safety of Chimeric Antigen Receptor-Redirected T Lymphocytes. J Cancer. 2011; 2: 378-382). Furthermore, such bispecific molecules with different specific targeting motifs can be administered simultaneously or sequentially to help address tumor resistance and escape as a results of target antigen loss without having to create, expand and infuse multiple different autologous CAR cells (Gill & June, 2015). Since all CAR constructions can be identical for all CAR cells and the targeting specificity determined simply by the targeting motif of the produced bispecific molecule of the instant invention, manufacturing processes will be simplified and less expensive.

Thus, the instant invention expands the diversity and practicality of this remarkable, very promising immunologic approach to managing cancer with CAR-T cells and CAR-NK cells while overcoming many of these current, recognized difficulties.

As used herein "peptide", "polypeptide", and "protein" are used interchangeably; and a "heterologous molecule", "heterologous peptide", "heterologous sequence" or "heterologous atom" is a molecule, peptide, nucleic acid or amino acid sequence, or atom, respectively, that is not naturally or normally found in physical conjunction with the subject molecule. As used herein, "non-natural" and "modified" are used interchangeably. As used herein, "natural" and "native" are used interchangeably and "NKG2D" and "NKG2D receptor" are used interchangeably. The term "antibody" herein is used in the broadest sense and specifically covers monoclonal antibodies, multispecific antibodies (e.g. bispecific antibodies), and antibody fragments, so long as they exhibit the desired biological activity. "Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multi-specific antibodies formed from antibody fragment(s).

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein are hereby incorporated by reference in their entireties, whether previously specifically incorporated or not. As used herein, the terms "a", "an", and "any" are each intended to include both the singular and plural forms.

Having now fully described the invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and may be applied to the essential features hereinbefore set forth.

EXAMPLES OF iFv AND OF MODIFIED α1-α2 DOMAINS OF NKG2D LIGANDS

Example 1 (iFv)

As specific examples, we synthesized a 1126 bp and a 1144 bp DNA fragment (SEQ ID NO:1 and 2, respectively) encoding in the following order: the α3 domain of human MICA (as a parent peptide) amino acid 182 to amino acid 194 (the beginning of loop 1 of the α3 domain), no spacer or a GGS amino acid spacer region (SR), an iFv peptide based on the structure of a Fibroblast Growth Factor Receptor 3 (FGFR3)-binding antibody (MAbR3;Qing, J., Du, X., Chen, Y., Chan, P., Li, H., Wu, P., Marsters, S., Stawicki, S., Tien, J., Totpal, K., Ross, S., Stinson, S., Dornan, D., French, D., Wang, Q. R., Stephan, J. P., Wu, Y., Wiesmann, C., and Ashkenazi, A. (2009) Antibody-based targeting of FGFR3 in bladder carcinoma and t(4;14)-positive multiple myeloma in mice, *The Journal of clinical investigation* 119, 1216-1229.), no spacer or another GGS spacer region, the distal portion of loop 1 of the α3 domain starting at amino acid 196 and including the remaining carboxy-terminal portion of the α3 domain to amino acid 276 of a soluble MICA molecule. Each synthetic, double stranded DNA polynucleotide then encoded a polypeptide that contained 6 CDRs in the form of an iFv inserted into loop 1 of the α3 domain of MICA.

Figure 5:
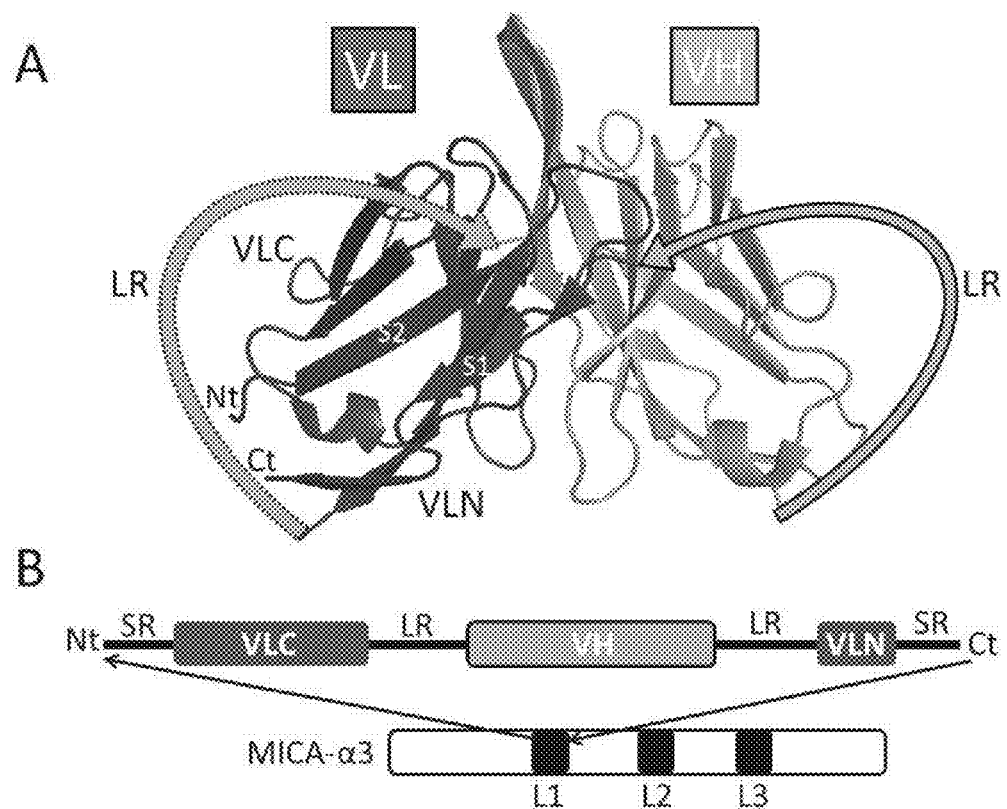
FIG. 5. Diagram of an insertable variable fragment, iFv. Diagram of an insertable variable fragment, iFv. (A) Structure of variable light (VL) and variable heavy (VH) domains from FGFR3-binding antibody showing the domain topology of the iFv format. Grey arrows represent the 2 linker regions (LR), one and only one of which is used traditionally to connect the termini of VL and VH to create an scFv. The LR with a dotted border connected the C-terminus of VL to the N-terminus of VH (visible behind the molecule). The LR with a solid border connected the C-terminus of VH to the N-terminus of VL. Segments of the split VL domain are labeled Nt and Ct as described in text. As a result of the creation of non-natural pair of N- and C-termini between strand 1 (S1) and strand 2 (S2) the VL has been divided into an N-terminal segment (VLN) and a C-terminal segment (VLC). The 6 CDRs of VL and VH are represented as the loops at the top of the figure. (B) Scheme of the domain layout for inserting an iFv into loop 1 (L1) of MICA-α3 with or without a spacer region (SR). An iFv could also be similarly inserted into loop 2 (L2) and/or loop 3 (L3).

This iFv peptide itself (SEQ ID NO.:3), encoded by SEQ ID NO.:4, contained two identical, typical linker regions (LR) corresponding to residues GGSSRSSSSGGGGSGGGG (SEQ ID NO.:5) (Andris-Widhopf, J., Steinberger, P., Fuller, R., Rader, C., and Barbas, C. F., 3rd. (2011) Generation of human Fab antibody libraries: PCR amplification and assembly of light- and heavy-chain coding sequences, *Cold Spring Harbor protocols* 2011). One LR joined the C-terminus of VL to the N-terminus of the VH domain, and the second LR joined the C-terminus of the VH domain to the N-terminus of VL. Conceptually this new structure is the continuous or "circular" peptide referred to above and contained 6 CDRs of the starting Fv. The variable VL chain of the antibody was effectively split within the loop region between beta-strands 1 and 2 (S1 and S2) and thereby created a new N-terminal segment (VLN) and a new C-terminal segment (VLC) with an accompanying pair of new, non-natural C- and N-termini, respectively, FIG. 5, panel A. This pair of termini created a sole site for attachment or conjugation of the iFv to the recipient molecule such as a protein. The schematic of the inserted iFv in the parent α3 domain is shown in FIG. 5, panel B.

To produce the soluble MICA proteins with a heterologous iFv peptide inserted into the α3 domain we generated a baculoviral expression vector to accommodate the DNA sequences (SEQ ID NOs:1 and 2) encoding the α3-iFv.1 (SEQ ID NO.:6) and α3-iFv.2 (SEQ ID NO.:7), respectively. The DNA fragments were amplified by PCR, digested using NcoI and EcoRI restriction enzymes, and subcloned into the baculoviral expression vector, SW403, replacing the wild-type α3 domain. SW403 is a baculoviral expression vector derived from pVL1393 (Invitrogen, Inc.) into which wild-type sMICA (residues 1-276) had previously been cloned using 5' BamHI and 3' EcoRI sites. The new expression vector was co-transfected with baculoviral DNA into SF9 insect cells, and baculovirus was grown for two amplification cycles and used to express the His-tagged MICA-α3-iFv proteins in T.ni insect cells according to manufacturer's protocol (Invitrogen). The expression was carried out in a 100 mL volume for three days and the growth medium was harvested for purification of the secreted soluble protein using Ni-affinity chromatography. Monomeric MICA-α3-iFv was purified to >90% purity with the expected molecular weight of 60.9 kDa as determined by SDS-PAGE. Functional characterization was carried out using binding ELISAs and in vitro target cell killing assays.

Figure 6:
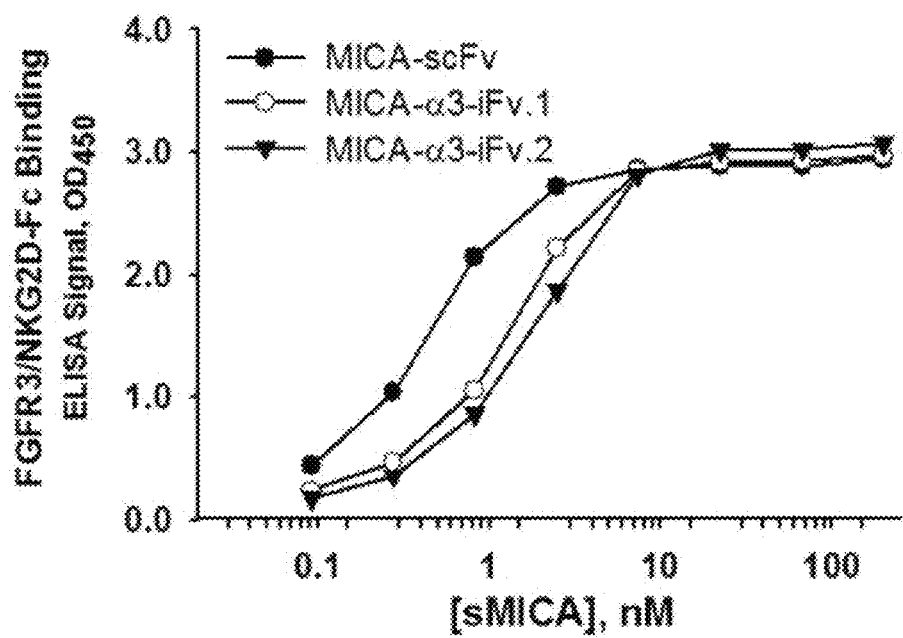
FIG. 6. Titration curves for the modified sMICA molecules binding to FGFR3 coated wells. Bound sMICA was detected by ELISA using NKG2D-Fc to confirm the bispecific activity. Both versions of the inserted variable fragments (MICA-α3-iFv.1 and M natural α1-α2 domains of NKG2D ligand-Fc fusions. (A), Wild type NKG2D binding to the α1-α2 domain ligand-Fc panel shows binding to all ligands, with highest affinity to MICv25-Fc. (B), Non-natural NKG2D mutant Y199A displays no ligand binding activity. (C), Non-natural NKG2D mutant Y152A retains high affinity binding to MICv25-Fc only. (D), Non-natural NKG2D double mutant Y152A and Y199A displays no ligand binding activity.

The purified MICA-α3-iFv proteins were tested in a FGFR3-binding ELISA to confirm simultaneous binding to the FGFR3 target and the NKG2D receptor. FGFR3 in phosphate buffered saline (PBS) was coated onto Maxisorp plates at 2 ug/ml concentration. Each MICA protein was titrated, allowed to bind FGFR3 for 1 hour, and washed to remove unbound sMICA protein. Bound MICA-α3-iFv protein was detected using NKG2D-Fc and anti-Fc-HRP conjugate. FIG. 6 shows that the binding of both MICA-α3-iFv.1 and MICA-α3-iFv.2 to FGFR3 was comparable to that of a MICA-scFv, made by fusing to the C-terminus of soluble MICA a traditional scFv constructed from MAbR3. These ELISA results also indicated that both the FGFR3 and NKG2D binding specificities of the scFv and the α1-α2 domain, respectively, were retained by the modified MICA and demonstrated that the iFv peptide inserted using different spacer formats was functional.

Figure 7:
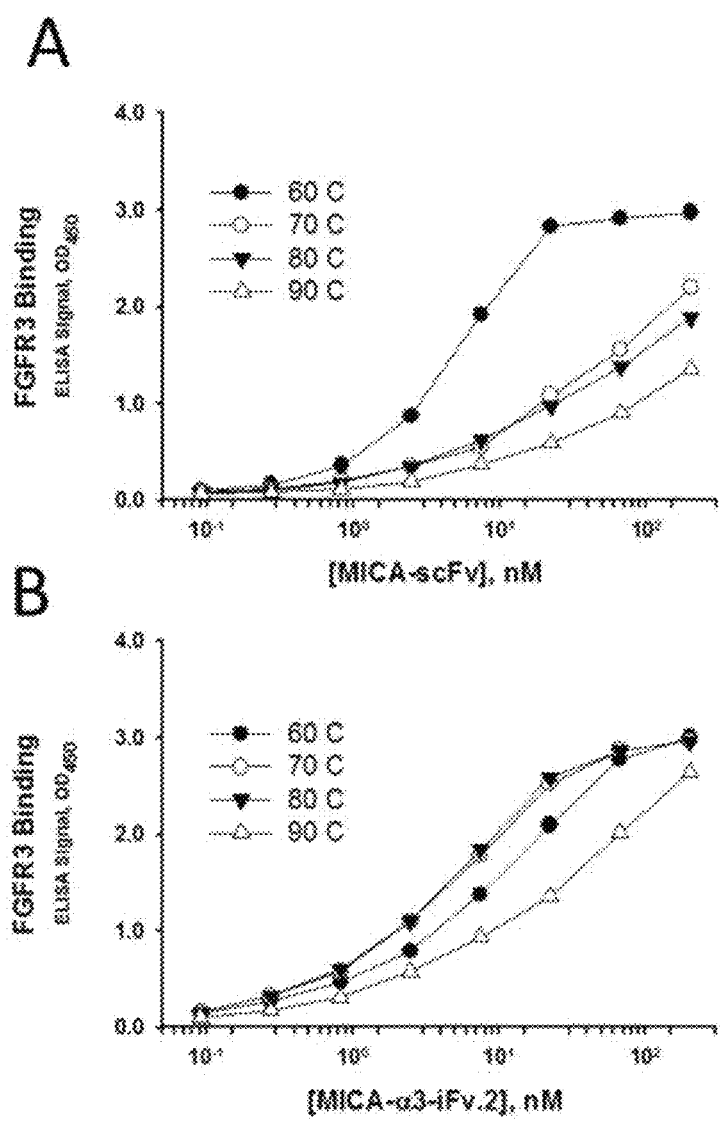

We tested and compared the thermal stability of sMICA-α3-iFv.2 to that of sMICA-scFv. Both proteins were subjected for 1 hr to increasing temperatures from 60-90° C. and then allowed to equilibrate to room temperature for 1 hour before being assayed for binding properties by ELISA. The results in FIG. 7 showed that MICA-α3-iFv.2 can be subjected to temperatures as high as 80° C. with no loss in specific binding to FGFR3. The traditional MICA-scFv lost binding activity at 70° C. This result indicated that soluble MICA containing the invented iFv format is significantly more stable than terminal fusions of a traditional scFv (Miller, B. R., Demarest, S. J., Lugovskoy, A., Huang, F., Wu, X., Snyder, W. B., Croner, L. J., Wang, N., Amatucci, A., Michaelson, J. S., and Glaser, S. M. (2010) Stability engineering of scFvs for the development of bispecific and multivalent antibodies, *Protein engineering, design & selection: PEDS* 23, 549-557; Weatherill, E. E., Cain, K. L., Heywood, S. P., Compson, J. E., Heads, J. T., Adams, R., and Humphreys, D. P. (2012) Towards a universal disulphide stabilised single chain Fv format: importance of interchain disulphide bond location and vL-vH orientation, *Protein engineering, design & selection: PEDS* 25, 321-329).

Figure 8:
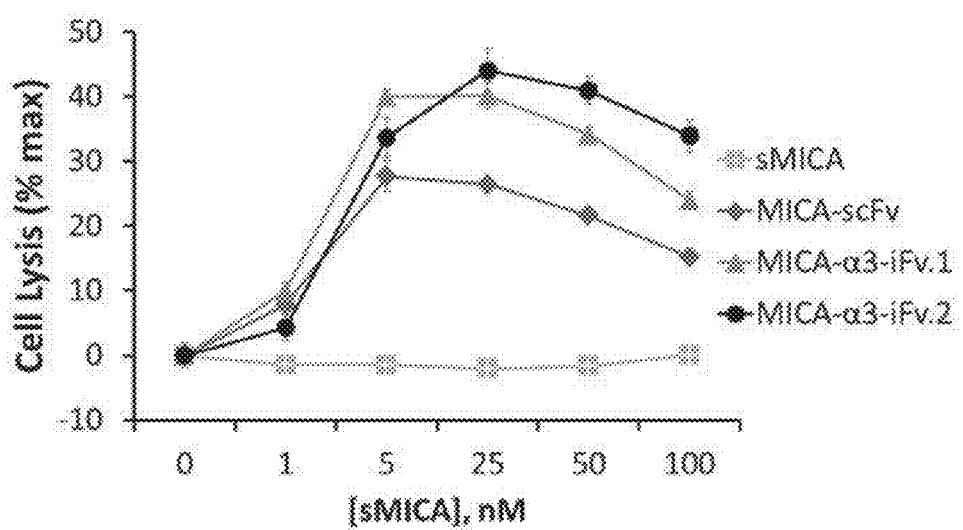

The ability of MICA-α3-iFv to redirect NK cell-mediated lysis of FGFR3-expressing target cells was demonstrated in vitro in a calcein-release assay. The Natural Killer (NK) cell line, NKL, was co-cultured with calcein-loaded P815 target cells ectopically expressing FGFR3. The results in FIG. 8 showed that the two MICA-α3-iFv molecules induced significantly greater NK-mediated lysis compared to the traditional MICA-scFv fusion, while the non-targeted soluble MICA control had no killing activity. These results confirmed that the invented iFv bound FGFR3 on target cells and in the context of the complete parent protein molecule, soluble MICA, induced potent NK cell-mediated lysis.

Figure 9:
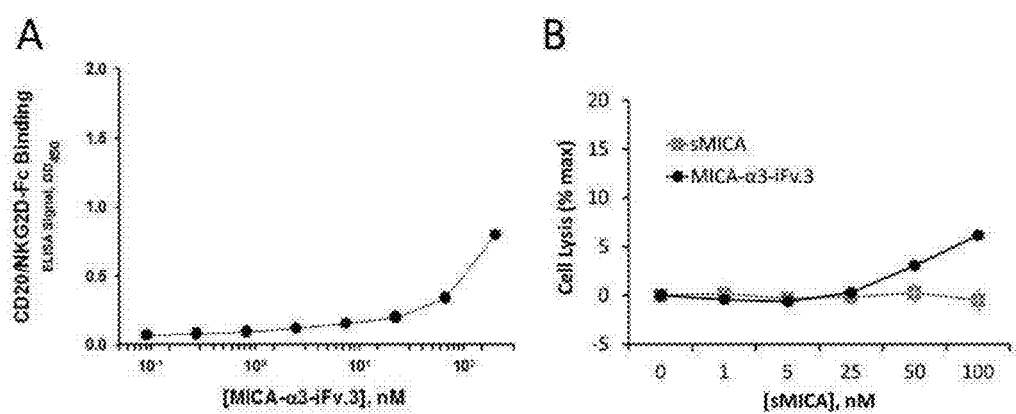

The applicability of the iFv format to other antibody variable domains was demonstrated by similarly constructing an α3-iFv.3 (SEQ ID NO.:8), which contained an iFv derived from a CD20-specific antibody (Du, J., Wang, H., Zhong, C., Peng, B., Zhang, M., Li, B., Huo, S., Guo, Y., and Ding, J. (2007) Structural basis for recognition of CD20 by therapeutic antibody Rituximab, *The Journal of biological chemistry* 282, 15073-15080). FIG. 9 shows that MICA-α3-iFv.3 was able to specifically bind wells coated with CD20 in a plate-based ELISA as described above and also induced NK-mediated lysis of Ramos cells expressing CD20 in a calcein-release assay.

Example 2 (Modified α1-α2 Domains of NKG2D Ligands)

Human proteins designated ULBP-1 through ULBP-6 are, like MICA and MICB, naturally occurring, stress-induced, cell surface ligands that bind NKG2D receptors on and activate human NK cells and certain T-cells (15; Cerwenka A, Lanier L L (2004). NKG2D ligands: unconventional MHC class I-like molecules exploited by viruses and cancer. *Tissue Antigens* 61 (5): 335-43. doi:10.1034/j.1399-0039.2003.00070.x. PMID 12753652). In addition, the cowpox virus protein OMCP is a secreted domain that like the α1-α2 domain of MIC proteins binds NKG2D. OMCP exhibits a very high affinity for NKG2D, apparently in order to block NKG2D's recognition of the natural stress ligands induced by the virus on its infected host cell (Eric Lazear, Lance W. Peterson, Chris A. Nelson, David H. Fremont. J Virol. 2013 January; 87(2): 840-850. doi: 10.1128/JVI.01948-12). While the ULBPs and OMCP are considered NKG2D ligands (NKG2DLs) that share the canonical α1-α2 domain structure, the sequence homology with MICA α1-α2 is less than 27%, and they all naturally lack an α3 domain for tethering targeting domains. We constructed a series of non-natural ULB and OMCP proteins by attaching the heterologous polypeptides that specifically targeted and killed FGFR3-expressing cells as the result of fusing to each of ULBP-1, ULBP-2, ULBP-3, ULBP-4, ULBP-6 and OMCP, a modified α3 domain of MICA into which a targeting iFv had been inserted. In addition, we modified the α1-α2 domain of MICA to enhance the affinity of α1-α2 domain for NKG2D and then attached to the modified α1-α2 domains heterologous molecules such as polypeptides. To produce the proteins consisting of ULBP and OMCP α1-α2 domains attached to modified α3-iFv domains we generated a baculoviral expression vector to accommodate the DNA fragments (SEQ ID NOs:9-14) that encoded the different α1-α2 domains of ULBP-1, ULBP-2, ULBP-3, ULBP-4, ULBP-6, and OMCP (SEQ ID NOs:15-20, respectively). The DNA fragments were amplified by PCR, digested using BlpI and NcoI restriction enzymes, and individually subcloned into the baculoviral expression vector, KLM44, replacing the MICA α1-α2 domain. KLM44 was a baculoviral expression vector derived from SW403 into which MICA-α3-iFv.2 had previously been cloned (example 1). The new NKG2DL-α3-iFv.2 constructs, containing the ULBPs and OMCP α1-α2 domain fusions to α3-iFv.2 (ULBP1-α3-iFv.2, ULBP2-α3-iFv.2, ULBP3-α3-iFv.2, ULBP4-α3-iFv.2, ULBP6-α3-iFv.2, and OMCP-α3-iFv.2; SEQ ID NO.:21-26, respectively), were co-transfected with baculoviral DNA into SF9 insect cells. Baculovirus was grown for two amplification cycles and used to express these His-tagged NKG2DL-α3-iFv.2 proteins in T.ni insect cells according to manufacturer's protocol (Invitrogen). The expression was carried out in a 100 mL volume for three days and the growth medium was harvested for purification of the secreted soluble protein using Ni-affinity chromatography. Monomeric proteins of correct molecular weight were purified to >90% purity as determined by SDS-PAGE. Functional characterization was carried out using binding ELISAs and in vitro target cell killing assays.

The 6 purified NKG2DL-α3-iFv.2 proteins were tested in a FGFR3-binding ELISA to confirm simultaneous binding to the FGFR3 target and the NKG2D receptor. FGFR3 in phosphate buffered saline (PBS) was coated onto Maxisorp plates at 2 ug/ml concentration. Each NKG2DL-α3-iFv.2 protein was titrated, allowed to bind FGFR3 for 1 hour, and washed to remove unbound protein. The bound NKG2DL-α3-iFv.2 protein was detected using NKG2D-Fc and anti-Fc-HRP conjugate. FIG. 10 shows that all 6 NKG2DL-α3-iFv.2 proteins bound potently to FGFR3, as expected, through interaction with the iFv.2 domain, and the NKG2D binding activity was retained by the attached NKG2DL α1-α2 domains, which demonstrated that the attached α3-iFv domain imparted functional FGFR3 binding activity to the ULBP and OMCP proteins that, like MIC proteins, bind NKG2D.

Figure 11:
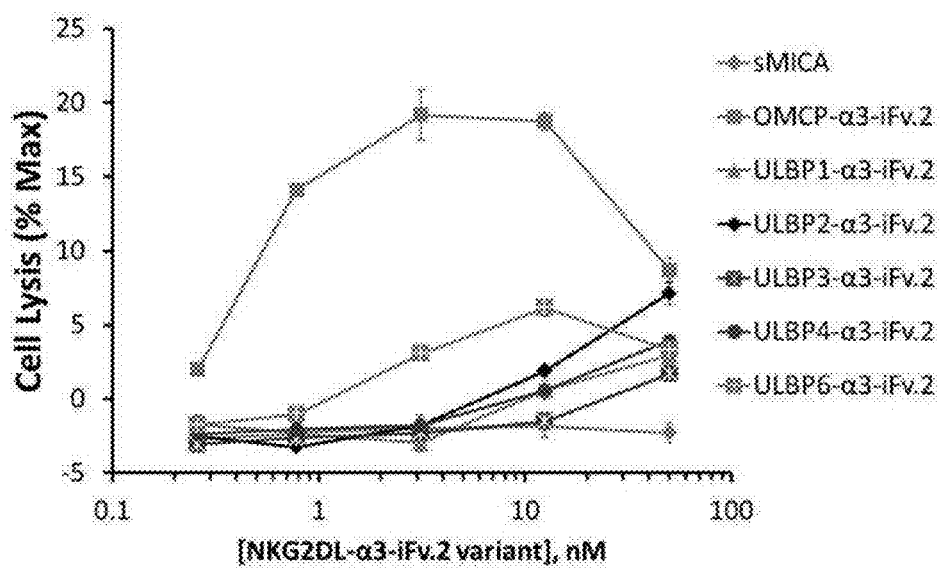

The ability of the NKG2DL-α3-iFv.2 proteins to redirect NK cell-mediated lysis of FGFR3-expressing target cells was demonstrated in vitro in a calcein-release assay. The Natural Killer (NK) cell line, NKL, was co-cultured with calcein-loaded P815 target cells ectopically expressing FGFR3. The results in FIG. 11 showed that OMCP-α3-iFv.2 induced the greatest NK-mediated lysis, while the other NKG2DL-α3-iFv.2 proteins all displayed specific killing activity with varying degrees of potency and amount of lysis. These results confirmed that the invented iFv imparts specific binding activity to other proteins that retained their own functional properties and induced different levels of cell-mediated lysis of iFv-targeted cells.

Example 3 (Modified α1-α2 Domains of NKG2D Ligands)

These are examples of attaching polypeptides to NKG2DLs which were modified to significantly enhance their binding affinity to the human NKG2D receptor. The α1-α2 domain of MIC proteins is an NKG2DL for the NKG2D receptor. This affinity is sufficient for physiologic activation of NK cells and stimulating lysis of cells expressing native full-length MIC proteins irreversibly tethered to the two-dimensional plasma membrane surface of a "target cell" (Bauer S, Groh V, Wu J, Steinle A, Phillips J H, Lanier L L, Spies T., Science. 1999 Jul. 30;285(5428):727-9.). However, because engineered soluble MIC proteins of the instant invention reversibly bind specific target antigens on the surface of a target cell, the binding affinity of the engineered soluble MIC protein to NKG2D will directly affect the stability of the soluble MIC-dependent complex formed between NK cells and cells expressing target antigens. Especially if the affinity between sMICA and NKG2D is increased by a substantially slower dissociation rate or off-rate of the modified sMICA from NKG2D, the NK cell-based killing would be expected to be greater at lower densities of soluble MIC molecules bound to a target cell. Prior to the instant invention there had not been identified any α1-α2 mutations that alter the killing activity of soluble MIC proteins or significantly reduce the binding off-rate to enhance affinity of MIC proteins to NKG2D. A computational design effort showed that three mutations in the α1-α2 domain of wild-type MICA: N69W, K152E, and K154D (WED-MICA) in combination can moderately affect NKG2D binding affinity by affecting the stability of unbound MICA and thereby its association rate or on-rate of binding to NKG2D (Lengyel C S, Willis L J, Mann P, Baker D, Kortemme T, Strong R K, McFarland B J. J Biol Chem. 2007 Oct. 19;282(42):30658-66. Epub 2007 Aug. 8); Subsequent extensive computational design work by the same group scanning by iterative calculations 22 amino acid positions of MICA theoretically in contact with NKG2D, according to the published structural descriptions (Li P, Morris D L, Willcox B E, Steinle A, Spies T, Strong R K., Nat Immunol. 2001 May; 2(5):443-451), showed experimentally that when combined with the earlier designed 3 changes, further rational, iterative computational design of MICA qualitatively changed its affinity for NKG2D from weak (Kd~2.5 μM) to moderately tight (Kd=51 nM) with a total of seven combined mutations (Henager, Samuel H., Melissa A. Hale, Nicholas J. Maurice, Erin C. Dunnington, Carter J. Swanson, Megan J. Peterson, Joseph J. Ban, David J. Culpepper, Luke D. Davies, Lisa K. Sanders, and Benjamin J. McFarland, 2102, Combining different design strategies for rational affinity maturation of the MICA-NKG2D interface. Protein Science 21:1396-1402). In contrast, the experimental approach described in the instant invention experimentally selected amino acid modifications of MICA that slowed the off-rate between the α1-α2 domain of MICA and NKG2D, commencing with a MICA stabilized by the 3 WED changes of Lengyel et al (Lengyel C S, Willis L J, Mann P, Baker D, Kortemme T, Strong R K, McFarland B J., J Biol Chem. 2007 Oct. 19;282(42):30658-66. Epub 2007 Aug. 8).

This example of the instant invention relates to modifying the NKG2D binding affinity of soluble MIC proteins through engineering specific mutations at selected amino acid positions within the α1-α2 domain that influence the off-rate binding kinetics and thereby alter the NK cell-mediated killing activity of the invented non-natural, targeted MIC molecules.

Figure 12:
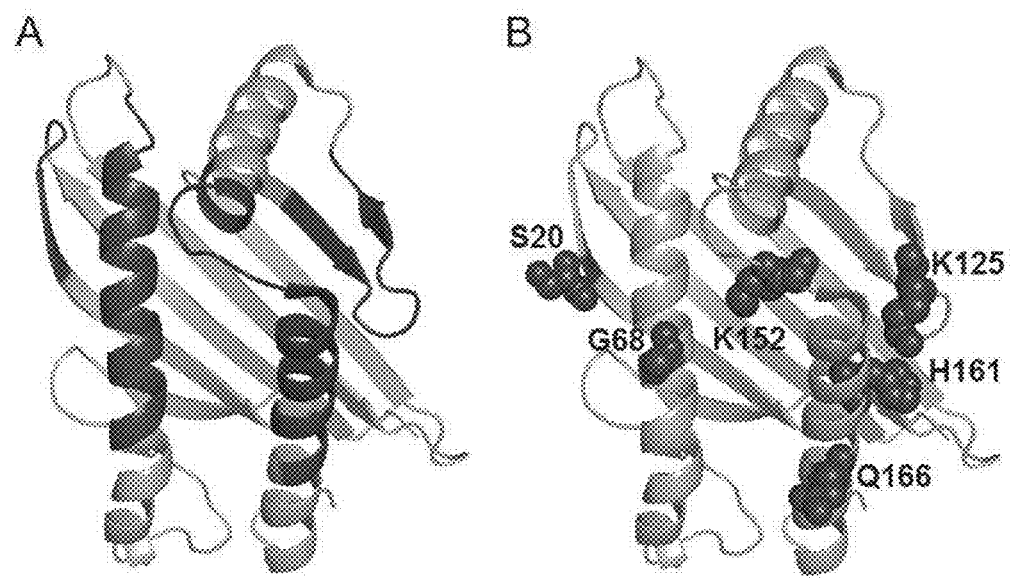

To engineer soluble non-natural α1-α2 domains with altered affinity to NKG2D 57 residues in the α1-α2 domain were chosen for extensive mutagenesis (FIG. 12). Synthetic DNA libraries coding for the α1-α2 domain and containing NNK mutagenic codons at each of the 57 amino acid positions were synthesized, individually cloned as fusions to the pIII minor coat protein of M13 phage, and phage particles displaying the mutagenized α1-α2 variants were produced in SS320 E. coli cells according to standard methodologies (Andris-Widhopf, J., Steinberger, P., Fuller, R., Rader, C., and Barbas, C. F., 3rd. (2011) Generation of human Fab antibody libraries: PCR amplification and assembly of light- and heavy-chain coding sequences, Cold Spring Harbor protocols 2011). The α1-α2 phage libraries were sorted for increased binding affinity using recombinant biotinylated NKG2D as the target antigen and cycled through iterative rounds of intentionally prolonged binding, prolonged washing, and eluting of the phage clones in order to select high affinity variants enriched for slow dissociation- or off-rates. A set of specific amino acid mutations occurred at high frequencies at 6 positions in α1-α2 and were selected as preferred amino acid substitutions with enhanced NKG2D binding affinity (FIG. 12, Table 1).

TABLE 1

Selected affinity mutations at the indicated 6 amino acid positions of the α1-α2 domain of MIC. The amino acids of SEQ ID NOs.: 35 at each of the 6 positions are shown in bold in the first row of the table. The identified affinity mutations are listed in decreasing frequency from top to bottom. All amino acids are represented by the single letter IUPAC abbreviations.

| S20 | G68 | K125 | E152 | H161 | Q166 |
|-----|-----|------|------|------|------|
| P | L | L | T | R | F |
| T | F | R | V | S | S |
| D | S | F | G | A | H |
| A | A | T | F | K | Y |
| L | Y | A | Y | G | W |
| N | I | N | A | L | V |
|   | E | V | Q | F | L |
|   | T | Y | D | Y | M |
|   | W | I | I |   |   |
|   |   | S | N |   |   |
|   |   |   | S |   |   |
|   |   |   | H |   |   |
|   |   |   | M |   |   |
|   |   |   | P |   |   |

We synthesized DNA polynucleotides (SEQ ID NOs. 27-30) encoding the α1-α2 domains of 4 representative variants 15, 16, 17, 18 that contained different combinations of specific discovered mutations (Table 2).

TABLE 2

Figure 13:
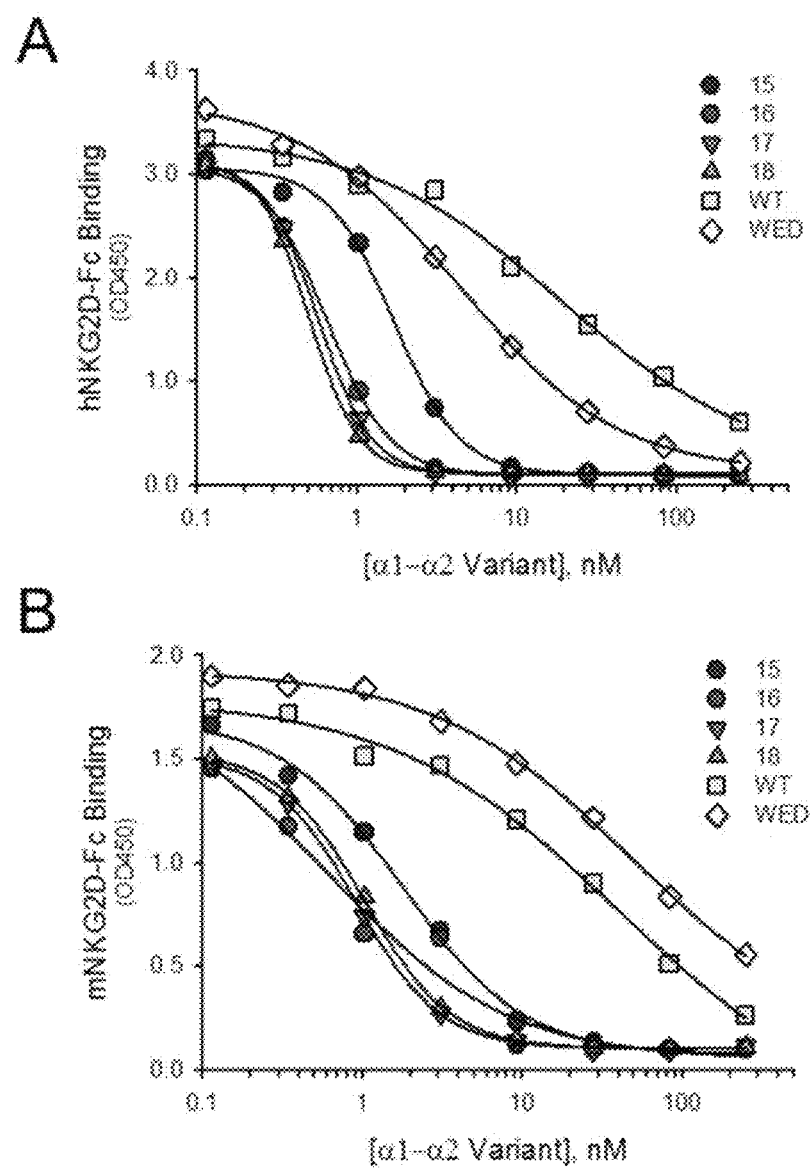
Figure 14:
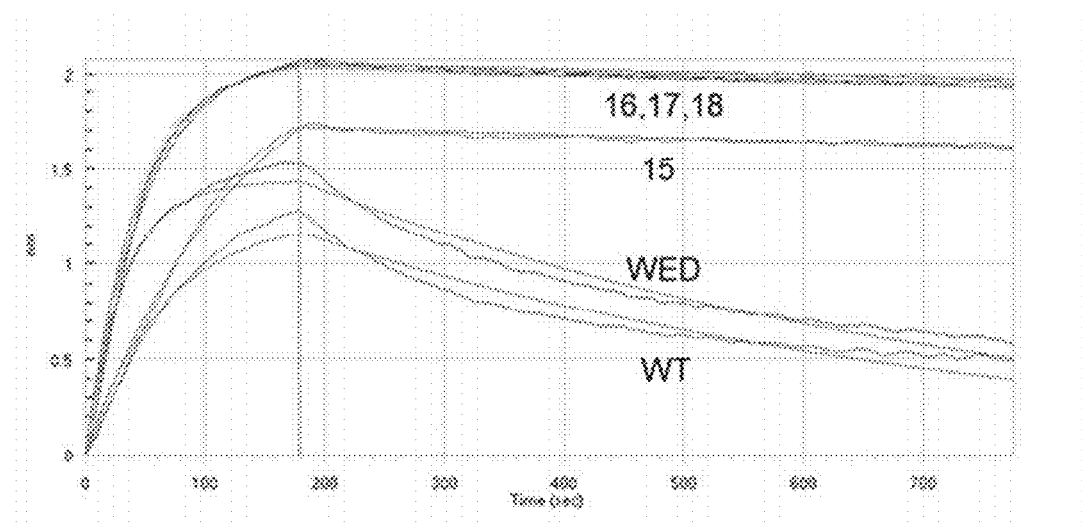
Figure 15:
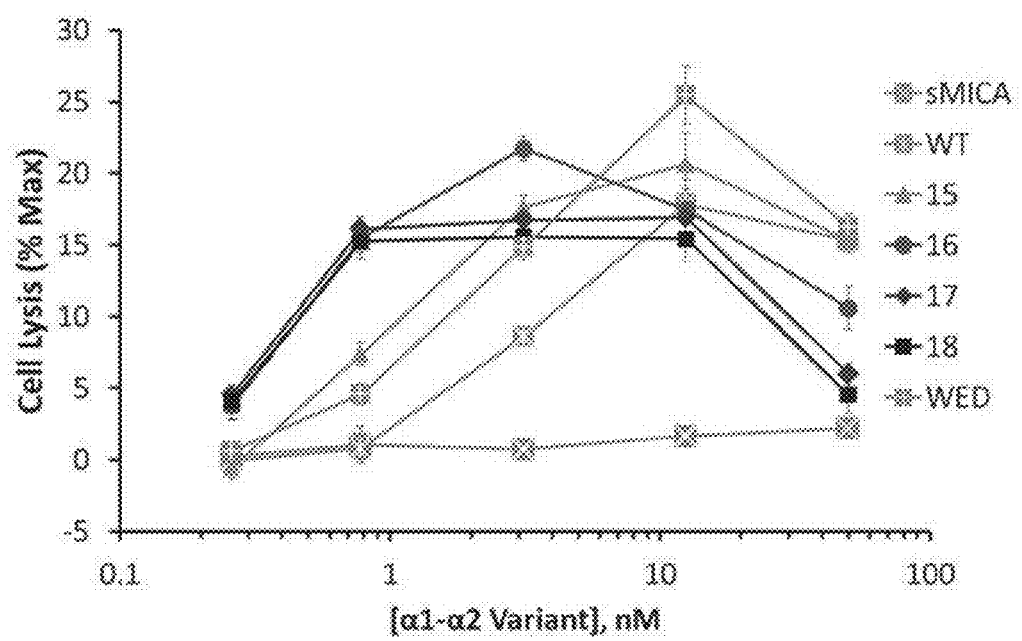

Sequences of specific α1-α2 domain variants. The specific amino acid substitutions for variants 15, 16, 17, and 18 (SEQ ID NOS.: 31-34, respectively) are listed relative to the amino acids of SEQ ID NO.: 35 in bold. All amino acids are represented by the single letter IUPAC abbreviations.

| Variant | SEQ ID NO.: | S20 | G68 | K125 | H161 |
|---|---|---|---|---|---|
| 15 | 31 | S | G | N | R |
| 16 | 32 | S | G | L | R |
| 17 | 33 | S | L | L | R |
| 18 | 34 | P | L | L | R |

To the NKG2DLs in the above example, we directly attached heterologous molecules such as a polypeptide to each of these 4 modified α1-α2 NKG2DLs using a linker peptide. Four His-tagged proteins (SEQ ID NOs.: 31-34) consisting of modified NKG2DLs with attached heterologous molecules were expressed in insect cells and purified to characterize their NKG2D binding affinities and kinetic binding parameters. Using a competitive binding ELISA, we determined the relative NKG2D binding affinities of the 4 modified α1-α2 variants. A soluble wild type (WT) NKG2DL, sMICA protein, was coated in all wells of a maxisorp ELISA plate to provide a binding partner for the human NKG2D-Fc reagent. Solutions of the four α1-α2 variants as well as WT and WED-α1-α2 domains (SEQ ID NO.: 35) were titrated in the ELISA wells and allowed to competitively inhibit 2 nM human NKG2D-Fc binding to the WT sMICA coated on the plate. The level of human NKG2D-Fc that bound to the WT NKG2DL on the plate was detected using an anti-Fc-HRP antibody. FIG. 13, Panel A, shows variants 16, 17, and 18 exhibited $IC_{50}$ values of 0.7, 0.6, 0.5 nM while variant 15 exhibited an $IC_{50}$ value of 1.7 nM, all possessing significantly better binding to NKG2D, 27, 32-, 38- and 11-fold better, than WT NKG2DL, respectively, as well as substantially better than WED-MICA (Table 3).

TABLE 3

Equilibrium and kinetic binding parameters for α1-α2 variants. $IC_{50}$ values were derived from 4-parameter fits to the competition binding titrations (FIG. 12) and the kinetic binding parameters were derived from single exponential fits to the binding kinetics (FIG. 13). Equilibrium binding constants ($K_d$) were derived from the kinetic binding parameters using the equation $K_d = k_{OFF}/k_{ON}$.

| | | Kinetic Binding Parameters | | |
|---|---|---|---|---|
| α1-α2 Variant | $IC_{50}$ (nM) | $k_{ON}$ ($M^{-1}$ $s^{-1}$) | $K_{OFF}$ ($s_{-1}$) | $K_d$ (nM) |
| WT | 19.4 | $1.3 \times 10^5$ | $1.8 \times 10^{-3}$ | 13.8 |
| WED | 4.4 | $2.9 \times 10^5$ | $1.7 \times 10^{-3}$ | 5.9 |
| 15 | 1.7 | $0.7 \times 10^5$ | $1.1 \times 10^{-4}$ | 1.5 |
| 16 | 0.7 | $2.0 \times 10^5$ | $0.9 \times 10^{-4}$ | 0.5 |
| 17 | 0.6 | $2.0 \times 10^5$ | $0.7 \times 10^{-4}$ | 0.4 |
| 18 | 0.5 | $2.3 \times 10^5$ | $0.9 \times 10^{-4}$ | 0.4 |

Importantly, the relative $IC_{50}$ differences also translated to better binding to murine NKG2D-Fc (FIG. 13, Panel B), and demonstrated the ability to improve binding of soluble, modified α1-α2 domains across human and non-human NKG2D receptors, an important property for preclinical drug development.

In order to understand the kinetic basis for the altered affinities, both the on-rates and off-rates for the α1-α2 variant NKG2DLs binding to surface coated biotinylated human NKG2D were measured using biolayer interferometry (Octet) at 100 nM of each of the modified α1-α2 proteins. Consistent with results from the $IC_{50}$ ELISAs, variants 16, 17 and 18 each displayed significant reductions in the off-rate (18-fold relative to WT), which is largely responsible for the affinity increase (~30-fold relative to WT α1-α2)(FIG. 14; Table 3). Although variant 15 displayed a similar slow off-rate as did 16, 17, and 18, its on-rate was decreased, resulting in an affinity stronger than WT but weaker variants 16, 17 and 18. Because the only difference between variant 15 (SEQ ID NO.:31) and 16 (SEQ ID NO.:32) was K125N versus K125L, the mutation at position 125 clearly altered the on-rate while the decreased off-rate was attributed to the H161R mutation. Therefore, while the selected set of NKG2DL mutations (Table 1) was used to increase the α1-α2 affinity for NKG2D through significant off-rate reduction, certain substitutions also altered the on-rate resulting in a range of incremental affinity increases that we showed in this invention to have differential activity in the NK cell-mediated killing assays as described below.

The ability of the α1-α2 affinity variants to redirect NK cell-mediated lysis of FGFR3-expressing target cells was demonstrated in vitro in a calcein-release assay. The human Natural Killer (NK) cell line, NKL, was co-cultured with calcein-loaded P815 target cells ectopically expressing FGFR3 and titrated with soluble modified MIC proteins. The results in FIG. 15 showed that the killing activities of the FGFR3-specific soluble MIC variants correlated with their engineered α1-α2 affinities. Specifically, variants 16, 17, and 18 exhibited ~15-fold more killing than WT at 0.78 nM. The WED-MICA (SEQ ID NO.:35) was only slightly better than WT. Therefore, the invention describes amino acid substitutions within the α1-α2 domain that increased the NKG2D binding affinity by reducing the off-rate of soluble MIC protein binding to human NKG2D and consequentially led to the predictably increased killing potency. WED-MICA, which exhibited somewhat greater affinity than WT MICA to NKG2D (FIG. 13, Panel A) by increasing on-rate rather than reducing off-rate (FIG. 14), did not exhibit substantial improvement of target cell killing (FIG. 15). Furthermore, as shown in FIG. 13, Panel B, WED-MICA exhibited substantially poorer binding to murine NKG2D than even WT MICA, while variants 15, 16, 17, and 18 each exhibited greater affinity for both human and murine NKG2D, FIG. 13, Panels A and B.

affinity variants enriched for slow dissociation- or off-rates. A set of specific amino acid mutations at 9 positions in the α1-α2 domain were selected as preferred sites of amino acid substitutions with enhanced NKG2D binding affinity. We synthesized DNA polynucleotides encoding the α1-α2 domains of 8 representative variants (SEQ ID NOs: 55-62) that contained different combinations of specific mutations (Table 4).

Table 4. The non-natural α1-α2 domain variants selected for increased affinity to natural NKG2D receptor and the MICwed variant described previously (McFarland et al., 2003). The positions of the indicated amino acid changes referenced to the residue positions in SEQ ID NO.: 42 and the common names of the variants and their SEQ ID NOs are provided.

TABLE 4

| a1a2 variant | SEQ ID NO. | aa# in wt MICA: |  |  |  |  |  |  |  |  |
|---|---|---|---|---|---|---|---|---|---|---|
|  |  | 20 | 68 | 69 | 125 | 152 | 154 | 158 | 161 | 166 |
| wt MICA | 42 | S | G | N | K | K | K | H | H | Q |
| MICwed | 55 | S | G | W | K | E | D | H | H | Q |
| DSM20 | 56 | S | A | W | L | Q | D | R | H | F |
| DSM25 | 57 | S | G | W | L | E | D | H | R | S |
| DSM27 | 58 | S | G | W | L | K | K | H | R | S |
| DSM28 | 59 | S | G | N | L | K | K | H | R | S |
| DSM42 | 60 | S | G | W | L | E | D | H | R | Q |
| DSM48 | 61 | S | G | W | L | A | D | I | R | A |
| DSM49 | 62 | T | Q | W | K | F | D | R | T | T |

These α1-α2 NKG2DL affinity variants 15, 16, 17, and 18 enhanced the binding affinity of the attached polypeptide to the NKG2D receptor and thereby enhanced NK cell-mediated lysis of targeted cells, FIG. 15.

Example 4 (Non-natural α1-α2 Domains of NKG2D Ligands and the Cognate Non-natural NKG2D Receptors to Which They Bind)

Figure 16:
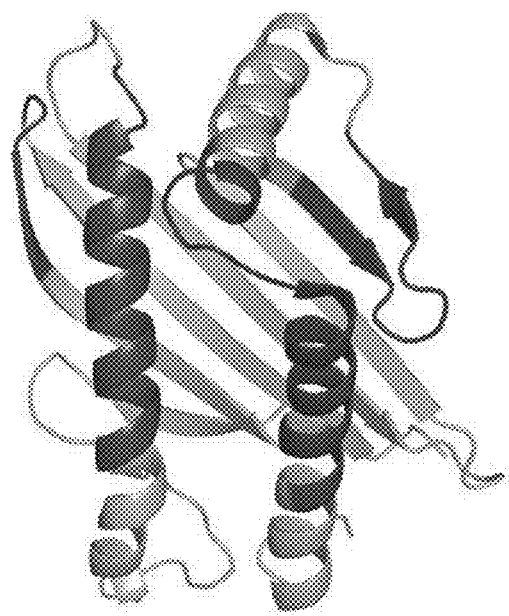

The α1-α2 domain of MICA and other NKG2D ligands bind the NKG2D receptor at a known specific site (Li et al 2001; Benjamin J. McFarland, Tanja Kortemme, Shuyuarn F. Yu, David Baker, and Roland K. Strong. Symmetry Recognizing Asymmetry: Analysis of the Interactions between the C-Type Lectin-like Immunoreceptor NKG2D and MHC Class I-like Ligands. Structure, Vol. 11, 411-422, April, 2003) and drive activation of the NKG2D receptor-bearing immune cell, which consequentially kills target cells displaying MICA or other ligands. We utilized phage display to engineer non-natural α1-α2 domains of MICA by extensive mutagenesis at 57 specific sites likely to be involved in binding to NKG2D (FIG. 16). Synthetic DNA libraries coding for the α1-α2 domain and containing NNK mutagenic codons at each of the 57 amino acid positions were synthesized, individually cloned as fusions to the pIII minor coat protein of M13 phage, and phage particles displaying the mutagenized α1-α2 variants were produced in SS320 *E. coli* cells according to standard methodologies (Andris-Widhopf, J., Steinberger, P., Fuller, R., Rader, C., and Barbas, C. F., 3rd, 2011. Generation of human Fab antibody libraries: PCR amplification and assembly of light- and heavy-chain coding sequences, *Cold Spring Harbor protocols* 2011). The α1-α2 phage libraries were sorted for increased binding affinity using recombinant biotinylated NKG2D as the target antigen and cycled through iterative rounds of intentionally prolonged binding, prolonged washing, and eluting of the phage clones in order to select high The DNA polynucleotides encoding the 8 variant α1-α2 domains were amplified with PCR primers (SEQ ID NO.s: 63-64). Using Blp1 and Sap1 restriction enzymes, each was subcloned into a His-tagged α1-α2-α3-Fv fusion expression construct (SEQ ID NO.:65) to replace the sequence encoding the natural (wt) α1-α2 sequences with the mutated α1-α2 sequences. The 9 fusion proteins (SEQ ID NO.s: 66-74) were expressed in 293 cells (Expi293™ Expression System, Life Technologies, Thermo Fisher, Inc.) and affinity purified using Ni-affinity chromatography (HisTrap HP, GE Healthcare Life Sciences).

To construct NKG2D receptor proteins, we synthesized DNA encoding the extracellular domain ("ectodomain") of the wild type receptor (SEQ ID No.:75) and used PCR primers (SEQ ID NO.s: 76-77) and XbaI and BamHI sites to clone the synthetic DNA into an N-terminal His-avitag expression vector (SEQ ID NO.: 78). The His-avitag-natural NKG2D (SEQ ID NO.:79) was expressed transiently in 293 cells and purified using Ni-affinity chromatography. Following purification, the NKG2D proteins were site-specifically biotinylated using BirA to attach a biotin group onto the avitag sequence (BirA biotin-protein ligase standard reaction kit, Avidity, LLC, Aurora, Colo.).

In order to characterize and compare the kinetic binding parameters of the natural and 8 variant α1-α2 domains to natural NKG2D, we measured their binding to surface coated biotinylated natural NKG2D ectodomain using bio-layer interferometry (Octet) at 100 nM of each of the α1-α2-α3-Fv fusion proteins. Results are displayed in Table 5.

Table 5: Kinetic parameters of the wild type (wt or natural) and 8 variant α1-α2 domain α3-Fv fusion proteins binding to the natural NKG2D. MICwed-Fv was here studied in 2 separate Octet analyses, once comparing to the wt α1-α2 domain α3-Fv fusion and the other compared to 7 other non-natural α1-α2 domain α3-Fv fusions. The common names of each α1-α2 domain variants and the SEQ ID NO.s of their α3-Fv fusion proteins are provided along with their affinity (Kd) values in molar (M), on rates (kon) in inverse molar-seconds (1/Ms), and dissociation- or off-rates (kdis) in inverse seconds.

TABLE 5

| α1α2 variant | SEQ ID NO.: | Kd (M) | kon (1/Ms) | kdis (1/s) |
| --- | --- | --- | --- | --- |
| wt MICA-Fv | 66 | 1.38E-08 | 1.30E+05 | 1.80E-03 |
| MICwed-Fv run A | 67 | 5.90E-09 | 2.90E+05 | 1.70E-03 |
| MICwed-Fv run B | 67 | 1.55E-08 | 2.01E+05 | 3.12E-03 |
| MICv20-Fv | 68 | 8.51E-11 | 3.59E+05 | 3.05E-05 |
| MICv25-Fv | 69 | 6.16E-11 | 4.67E+05 | 2.88E-05 |
| MICv27-Fv | 70 | 4.11E-10 | 2.08E+05 | 8.54E-05 |
| MICv28-Fv | 71 | 3.30E-10 | 2.46E+05 | 7.03E-05 |
| MICv42-Fv | 72 | 1.09E-10 | 3.47E+05 | 3.78E-05 |
| MICv48-Fv | 73 | 2.44E-10 | 5.95E+05 | 1.45E-04 |
| MICv49-Fv | 74 | 7.46E-10 | 3.70E+04 | 2.76E-05 |

As shown in Table 5, the selected α1-α2 domain mutations as fusions to heterologous polypeptides α3-Fv of SEQ ID NO.s: 68-74 increased the α1-α2 domain affinity for natural NKG2D through significant reduction of the off-rate. The off-rates ranged from 20- to more than 100-fold slower than those of wt (SEQ ID NO.:66) and the previously described MICwed α1-α2 domain variant (SEQ ID NO.:67).

Figure 17:
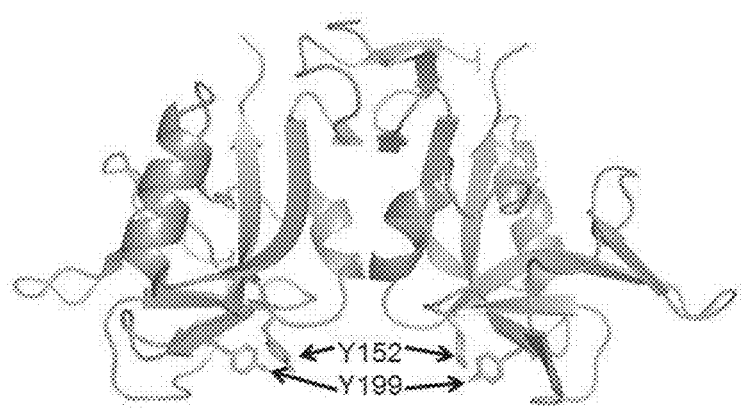

In this example of the instant invention, we further demonstrated as described below, that a non-natural α1-α2 domain (DSM25, SEQ ID NO.:57, Table 4) that as an α1-α2-α3-Fv fusion had high affinity for and very slow off-rate from natural NKG2D (Table 2; SEQ ID NO.:69), exhibited tight binding affinity to a non-natural NKG2D receptor containing a specific mutation that abolished its binding to natural NKG2D ligands. It had been demonstrated by others that mutations at tyrosine 152 and tyrosine 199 in human NKG2D, the equivalent of positions 73 and 120 of the NKG2D ectodomain (SEQ ID NO.:75 and FIG. 17) abolish binding to the natural ligand, MICA (David J. Culpepper, Michael K. Maddox1, Andrew B. Caldwell, and Benjamin J. McFarland. Systematic mutation and thermodynamic analysis of central tyrosine pairs in polyspecific NKG2D receptor interactions. Mol Immunol. 2011 January; 48(4): 516-523).

To construct the non-natural NKG2D receptor proteins, we used PCR primers (SEQ ID NO.s:76-77) to clone the DNA encoding the natural NKG2D ectodomain (SEQ ID NO.:75) and insert it into the N-terminal His-avitag expression vector SEQ ID NO.:78 to produce His-avitag-NKG2D (SEQ ID NO.:79). Site-directed mutagenesis was performed on the natural NKG2D ectodomain DNA construct to introduce Y152A, Y199A, or Y152A plus Y199A mutations and created three non-natural variants of human NKG2D (SEQ ID NO.s: 80-82, respectively). The natural NKG2D and 3 non-natural NKG2D mutants with His-avitags were expressed transiently in 293 cells and purified using Ni- affinity chromatography. Following purification, the NKG2D proteins were site-specifically biotinylated using BirA to attach a biotin group onto the avitag sequence (BirA biotin-protein ligase standard reaction kit, Avidity, LLC, Aurora, Colo.).

To generate fusions of α3-Fc heterologous polypeptides to α1-α2 domain of MICwed (SEQ ID NO.:55) and DSM25 α1-α2 domain (SEQ ID NO.: 57) the DNA polynucleotides encoding the α1-α2 domains were amplified using PCR primers (SEQ ID NO.s: 63-64). Using XbaI and NcoI restriction enzymes, each was subcloned into a α1-α2-α3-Fc fusion expression construct (SEQ ID NO.:83) to replace the sequence encoding the natural (wt) α1-α2 sequences with the mutated α1-α2 sequences. The 3 fusion proteins, MICA-Fc (SEQ ID NO.: 84), MICwed-Fc (SEQ ID NO.: 85), and MICv25-Fc (SEQ ID NO.: 86) were expressed in 293 cells (Expi293™ Expression System, Life Technologies, Thermo Fisher, Inc.) and affinity purified using Protein A affinity chromatography (cat. no. 20334, Pierce Biotechnology, Rockford, Ill.).

Figure 18:
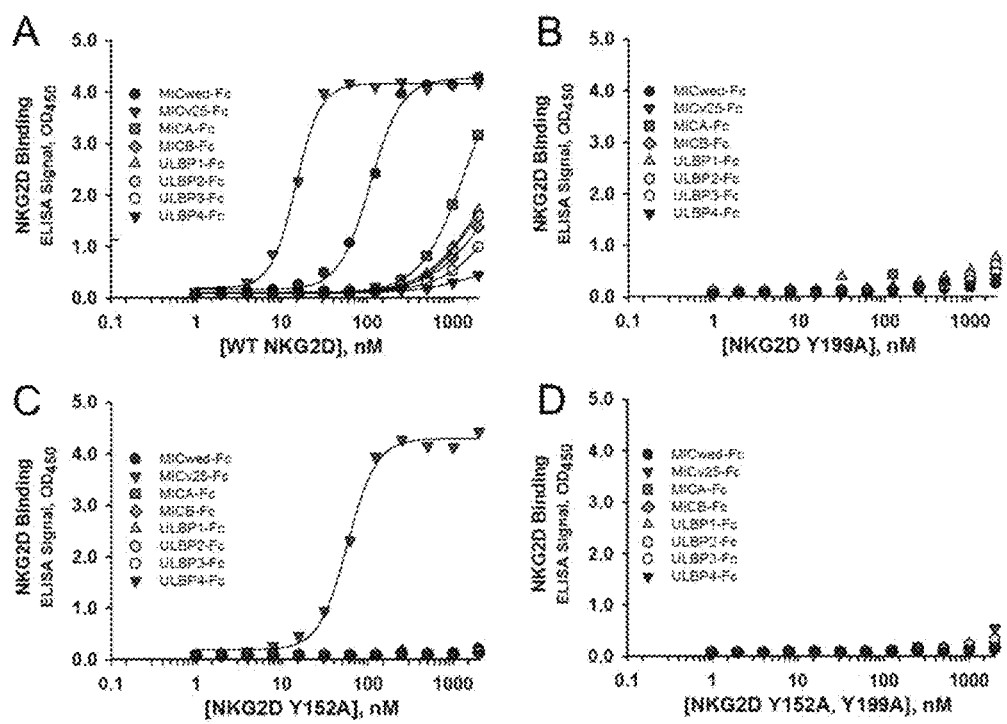
Figure 21:
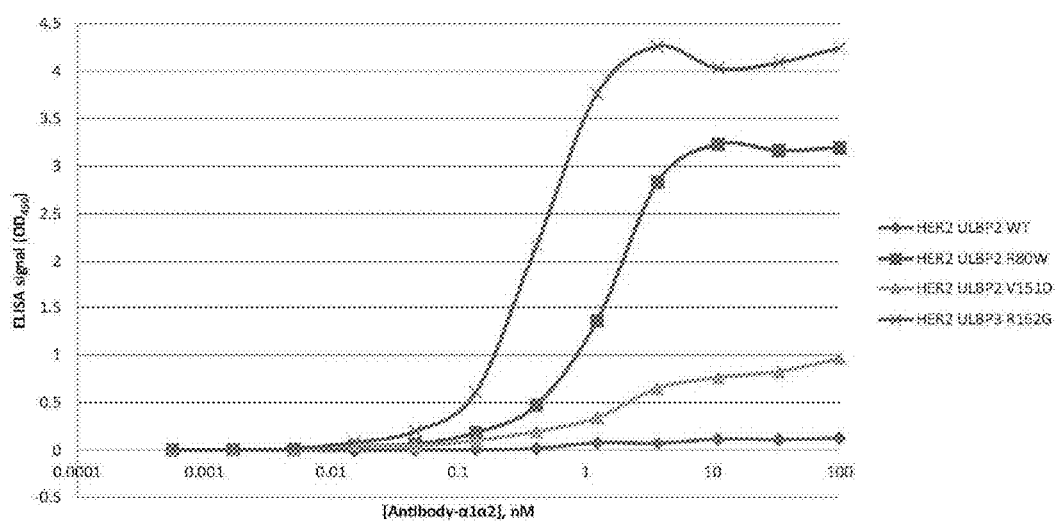
FIG. 21. Fusions of ULBP2 and ULBP3 α1-α2 domain variants to the heavy chain of a HER2-specific antibody showed enhanced NKG2D binding affinity. Modified ULBP2 α1-α2 domain variants R80W (SEQ ID NO: 87) and V151D (SEQ ID NO: 88) and modified ULBP3 variant R162G (SEQ ID NO: 89) displayed enhanced NKG2D binding relative to their C-to-S natural ULBP fusions (SEQ ID NOs: 16 and 17, respectively).
Figure 22:
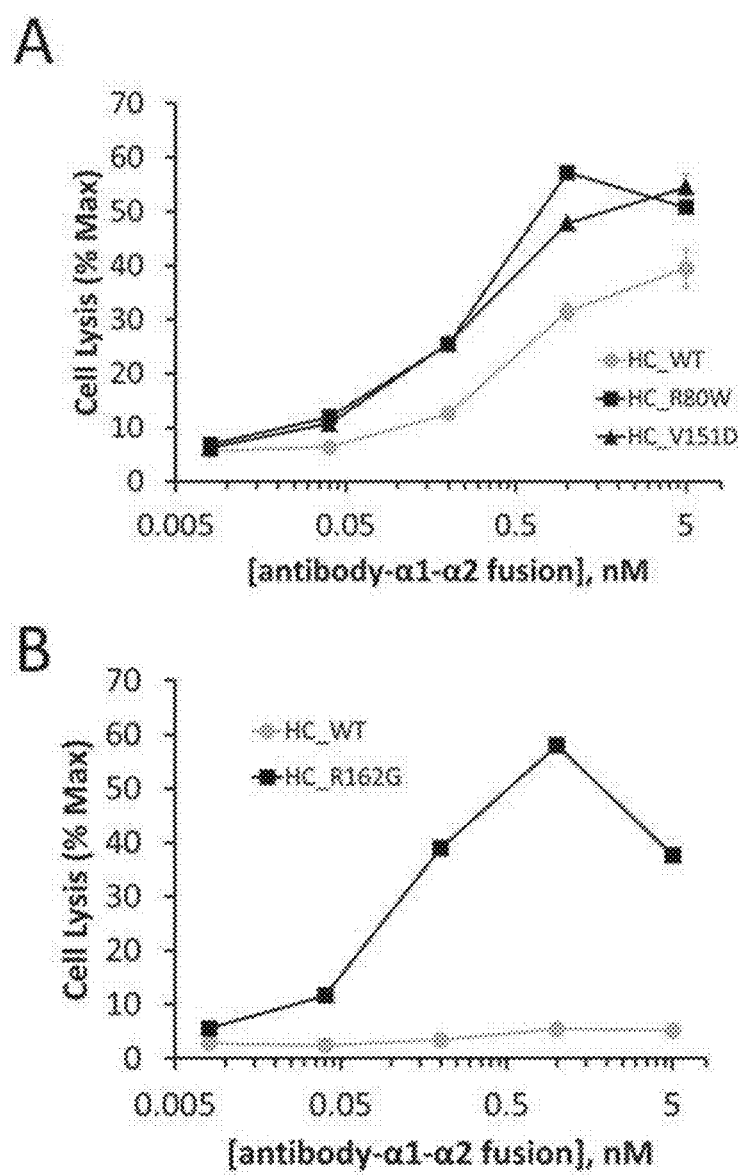
FIG. 22. Fusions of ULBP2 and ULBP3 α1-α2 domain variants to the heavy chain of a HER2-specific antibody-mediated showed specific lysis of SKBR3 target cells by NKL cells. Modified ULBP2 α1-α2 domain variants R80W (SEQ ID NO: 87) and V151D (SEQ ID NO: 88) displayed enhanced target cell killing relative to the C8S native ULBP2 (SEQ ID NO: 16) fusion (WT) (A). Modified ULBP3 variant R162G (SEQ ID NO: 89) displayed enhanced target cell killing relative to the C103S native ULBP3 (SEQ ID NO: 17) fusion (WT) (B).

In addition to purifying the above 3 Fc-fusion proteins NKG2D ligand-Fc fusion proteins MICB-Fc, ULBP1-Fc, ULBP2-Fc, ULBP3-Fc, and ULBP4-Fc were purchased from R&D Systems, Inc. (Minneapolis, Minn.). Binding of the different α1-α2 domain-Fc fusions to both natural and non-natural NKG2D ectodomain proteins was analyzed using a plate-based ELISA method. All of the natural and non-natural α1-α2 domain-Fc fusions were coated overnight at 4° C. onto separate wells of Maxisorp 96 well plates using a coating concentration of 2 µg/ml in phosphate-buffered saline (PBS). The plates were washed 3-times in PBS/0.05% Tween20 at 20-22° C., and blocked with 0.5% bovine serum albumin for 2 hours. The biotinylated natural and non-natural NKG2D receptor proteins were titrated against the plate-bound NKG2D ligands for 2 hours at 20-22° C., washed 3 times with PBS/0.05% Tween20 at 20-22° C., and the bound NKG2D proteins subsequently detected using a streptavidin-HRP secondary detection step and developed with 1-Step Ultra TMB Elisa. The natural form of the ectodomain of NKG2D (SEQ ID NO.:75) was capable of binding all α1-α2 domain-Fc fusions tested (FIG. 18, Panel A). The non-natural MIC-v25 α1-α2 domain ligand bound with the highest affinity ($EC_{50}$=14 nM), which was 8-fold better than MICwed and more than 100-fold better than all natural α1-α2 domain ligands tested (FIG. 18, Panel A). All ligands tested, both natural and non-natural α1-α2 domains, lost binding to the Y199A (SEQ ID NO.:81; FIG. 18, Panel B) and to the double Y152A plus Y199A (SEQ ID NO.:82; FIG. 18, Panel D) mutant NKG2D receptors. However, of all the natural and non-natural α1-α2 domain ligands tested, only the non-natural α1-α2 domain (SEQ ID NO.:57) of MICv25-Fc (SEQ ID NO.:86) retained binding to the Y152A mutant NKG2D ectodomain (SEQ ID NO.:80) with an EC50 of 50 nM (FIG. 18, Panel C).

While the binding specificity of natural NKG2D shows preference for the high affinity non-natural ligands, its potent binding to the natural NKG2D ligands, which are present on certain healthy tissues and many stressed tissues, creates an extreme risk for toxicity using current NKG2D CAR approaches (VanSeggelen et al. 2015). The Y152A non-natural NKG2D receptor specifically bound to only the protein comprised of the high affinity non-natural α1-α2 domain engineered for a markedly decreased off-rate. This prototypical example highlighted the ability of non-natural α1-α2 domains to bind non-natural NKG2D receptors, thus provided for selective control of non-natural NKG2D CARs using bispecific proteins containing the invented non-natural α1-α2 domain of NKG2D ligands.

Example 5 (Modified α1-α2 Domains of NKG2D Ligands)

This embodiment relates to additional α1-α2 NKG2DL affinity variants derived through engineering the α1-α2 domains of ULBP proteins. ULBP proteins contain α1-α2 domains, which are NKG2D ligands capable of binding to the NKG2D receptor (Cerwenka A, Lanier L L (2004). NKG2D ligands: unconventional MHC class I-like molecules exploited by viruses and cancer. *Tissue Antigens* 61

(5): 335-43. doi:10.1034/j.1399-0039.2003.00070.x. PMID 12753652). This affinity of NKG2D binding is sufficient for physiologic activation of NK cells and stimulating lysis of cells expressing native full-length ULBP proteins naturally and irreversibly tethered to the two-dimensional plasma membrane surface of a "target cell" (Cerwenka A, Lanier L L (2004). NKG2D ligands: unconventional MHC class I-like molecules exploited by viruses and cancer. *Tissue Antigens* 61 (5): 335-43. doi:10.1034/j.1399-0039.2003.00070.x. PMID 12753652). However, because engineered soluble α1-α2 domains fused to heterologous polypeptides in certain embodiments of the instant invention reversibly bind specific target antigens on the surface of a target cell, the binding affinity of the engineered ULBP α1-α2 domains to NKG2D will directly affect the stability of the artificial synapse formed between NK cells and cells expressing target antigens, as already shown by engineered soluble MIC proteins (Examples 2-4). In order to diversify the repertoire of engineered non-natural α1-α2 domains as NKG2D ligands, ULBP proteins were used as a substrate or starting point for phage display-based engineering of their NKG2D binding affinity. Despite the structural homology observed between ULBPs and MICA (Radaev, S., Rostro, B., Brooks, A G., Colonna, M., Sun, P D. (2001) Conformational plasticity revealed by the cocrystal structure of NKG2D and its class I MHC-like Ligand ULBP3. *Immunity* 15, 1039-49.), the sequence homology is <50% for the ULBP α1-α2 domains relative to MICA. Thus, we sought the identities of codon positions in ULBP α1-α2 domains that improve NKG2D binding affinity.

To engineer soluble, non-natural α1-α2 domains from ULBP proteins, ULBP2 and ULBP3 were chosen for phage display and selection of mutants with high affinity NKG2D binding. Sixty amino acid positions in the α1-α2 domain of ULBP2 (SEQ ID NO: 16), and thirty-six amino acid positions in the α1-α2 domain of ULBP3 (SEQ ID NO: 17), were chosen for extensive mutagenesis. In addition, conservative cysteine-to-serine mutations were made at C8S in ULBP2 (SEQ ID NO: 16) and C103S in ULBP3 (SEQ ID NO: 17) eliminating unpaired free cysteines in order to increase stability and function of the NKG2D ligands with attached polypeptides as well as to improve phage panning processes. Synthetic DNA libraries coding for these cysteine to serine modified α1-α2 domains, and containing NNK mutagenic codons at each of the selected amino acid positions, were synthesized, individually; cloned as fusions to the pIII minor coat protein of M13 phage; and phage particles displaying the mutagenized α1-α2 ULBP2 or ULBP3 variants were produced in SS320 *E. coli* cells according to standard methodologies (Andris-Widhopf, J., Steinberger, P., Fuller, R., Rader, C., and Barbas, C. F., 3rd. (2011). Generation of human Fab antibody libraries: PCR amplification and assembly of light- and heavy-chain coding sequences, *Cold Spring Harbor protocols* 2011). The α1-α2 phage display libraries were sorted for increased binding affinity to NKG2D using human NKG2D-Fc as the target protein, and cycled through iterative rounds of intentionally prolonged binding, prolonged washing, and eluting of the phage clones in order to select high affinity variants enriched for slow dissociation- or off-rates. For ULBP2, specific amino acid mutations were found at high frequencies at positions R80, V151, V152, and A153 in α1-α2, and were identified as preferred amino acid substitutions with enhanced NKG2D-binding affinity (FIG. 19, panel A; and Table 6).

TABLE 6

Selected affinity mutations at the indicated 4 amino acid positions of the α1-α2 domain of ULBP2. The amino acids of SEQ ID NO: 16 at each of the 4 positions are shown in bold in the first row of the table. The identified affinity mutations are listed in decreasing frequency from top to bottom. All amino acids are represented by the single letter IUPAC abbreviations.

| R80 | V151 | V152 | A153 |
|---|---|---|---|
| L | D | L | E |
| W | E | W | K |
| V | Q |   | G |
| F | K |   | P |
| I | N |   |   |
| S | R |   |   |
| A | T |   |   |
| E |   |   |   |
| P |   |   |   |
| T |   |   |   |

For ULBP3, specific amino acid mutations were found at high frequencies in different locations relative to ULBP2. Positions R162 and K165 in the α1-α2 domain of ULBP3 contained specific mutations that were identified as preferred amino acid substitutions with enhanced NKG2D-binding affinity (FIG. 19, Panel B; and Table 7). These modified non-natural α1-α2 domains derived from ULBP2 and ULBP3 can be used for enhanced NKG2D binding in multiple therapeutic formats as single proteins or fusions to heterologous peptides or polypeptides.

TABLE 7

Selected affinity mutations at the indicated 2 amino acid positions of the α1-α2 domain of ULBP3. The amino acids of SEQ ID NO: 17 at each of the 2 positions are shown in bold in the first row of the table. The identified affinity mutations are listed in decreasing frequency from top to bottom. All amino acids are represented by the single letter IUPAC abbreviations.

| R162 | K165 |
|---|---|
| G | S |
| A | P |
| Y | A |
|   | T |
|   | H |
|   | N |
|   | Q |
|   | G |

Example 6 (Binding and Cytolysis by Modified α1-α2 Domains of ULBPs Fused to Antibody Peptides)

The following example relates to attaching antibody polypeptides to NKG2DLs which were modified to significantly enhance their binding affinity to the human and murine NKG2D receptor. The α1-α2 domain of each ULBP protein is a natural ligand for the NKG2D receptor, i.e. an NKG2DL. Antibodies are highly stable glycoproteins made up of two large heavy chains and two small light chains (FIG. 1). There did not exist in the art an IgG antibody format that can directly activate immune cells using non-natural ULBP α1-α2 domains that bind more tightly than native ULBP domains to the NKG2D receptor. Furthermore, the ULBP α1-α2 domains provide alternative NKG2DLs to construct antibody fusions that may have differential in vivo properties relative to MICA α1-α2 domains. For example, an in vivo anti-drug antibody response to MICA α1-α2 domains within an antibody fusion would likely not react to or interfere with modified ULBP α1-α2 domains due to the low sequence homology between ULBP and MICA α1-α2 domains (FIG. 20). This example shows that fusions between the engineered ULBP α1-α2 NKG2D ligands (Table 6 and 7) and a heavy chain of an IgG molecule have enhanced NKG2D binding and target cell killing relative to natural ULBP α1-α2 NKG2D ligands. This further demonstrates the utility of fusions of modified α1-α2 domains to heterologous proteins or peptides.

To generate engineered α1-α2 domain fusions to antibodies, the DNA sequences encoding the C8S modified α1-α2 domains of ULBP2 (SEQ ID NO.: 16) variants R80W and V151D (SEQ ID NO.s: 87 and 88, respectively) and the C103S modified α1-α2 domain of ULBP3 (SEQ ID NO.: 17) variant R162G (SEQ ID NO.: 89) were synthesized and cloned as C-terminal fusions to the heavy chain sequence from the Her2-specific antibody (Carter, P., Presta, L., Gorman, C M., Ridgway, J B., Henner, D., Wong, W L., Rowland, A M., Kotts, C., Carver, M E., Shepard, H M. (1992) Proc Natl Acad Sci 15, 4285-9.). The resulting fusions were cloned into the mammalian expression vector pD2509 and expressed with the light chain of the parent antibody as paired full IgG antibodies. Transient expressions were carried out in HEK293 cells using the Expi293 expression system according to the manufacturer's protocol (Life Technologies), and purified using standard protein A affinity chromatography. Binding ELISAs performed on the ULBP2 and ULBP3 α1-α2 antibody heavy chain fusions demonstrated the modified ULBP2 fusions (HC_R80W and HC_V151D) and UBLP3 fusion (HC_R162G) bound with higher affinity to human NKG2D relative to their respective natural α1-α2 domains fused to the same heavy chain (FIG. 21, Panels A and B).

To characterize the target cell killing properties of the modified ULBP antibody fusions, the human Natural Killer (NK) cell line, NKL, was co-cultured with calcein-loaded SKBR3 target cells expressing Her2 and titrated with the engineered antibody fusion proteins. The results in FIG. 22, Panels A and B, showed that the enhanced cytolytic (killing) activities of the Her2-specific non-natural ULBP2 and non-natural ULBP3 α1-α2-antibody fusions reflected the enhanced affinities of their engineered α1-α2 domains for NKG2D. Specifically, ULBP2 variant fusions HC_R80W and HC_V151D, and the ULBP3 variant fusion HC_R162G, killed SKBR3 cells more effectively than antibody fusions containing either native α1-α2 domain. These data further showed that modified α1-α2 variant-antibody fusions are a universal platform for enabling IgG molecules to bind tightly to NKG2D and to direct antigen-specific cell lysis.

Example 7 (Constructing Orthogonal Non-natural α1-α2 Domains with Selective Binding to Y152A Non-natural NKG2D)

Means to selectively control CAR-T cell therapies are highly sought after to mitigate toxicity and improve efficacy against tumors (Gill and June, op cit). Previous attempts have been made to develop CARs using the ectodomain of CD16 which can then be engaged through the Fc domain of therapeutic monoclonal antibodies, allowing for antibody-based control of CAR-T targeting (Chang et al., op cit. However, CD16-based CAR-T cells can recognize all endogenous antibody molecules in blood and tissues, and the therapeutic antibodies used to control these cells will encounter interference from endogenous CD16 receptors on NK cells. Both of these features create problems with off-tumor toxicity and poor pharmacokinetics, respectively.

To address these issues we have engineered non-natural NKG2D CAR-T cells which lack binding to all natural NKG2D ligands and can be controlled through the binding of high-affinity non-natural α1-α2 domains as demonstrated in Example 4. An additional requirement is for the non-natural α1-α2 domains to retain high affinity for non-natural NKG2D, and avoid binding to natural NKG2D domains. Thus, engineered α1-α2 domains that exhibit strong selectivity for non-natural NKG2D receptors over natural NKG2D represent an ideal system for selective control of non-natural NKG2D CAR receptors, or any receptor or protein fused to non-natural NKG2D ectodomains that can be selectively engaged by non-natural α1-α2 domains.

We employed phage display to engineer orthogonal non-natural α1-α2 domains that exhibit selective binding to the Y152A NKG2D receptor. As a starting point, three non-natural α1-α2 domains with high affinity for natural NKG2D were selected as parent domains for further mutagenesis and screening by phage display. Synthetic DNA libraries were generated for the individual α1-α2 domain variants DSM25, ULBP2 R80W, and ULBP3 R162G (SEQ ID NO.s: 57, 87, and 89), whereby codons of amino acid residues that in the bound state are positioned in close proximity to the Y152 position on the NKG2D receptor were replaced with NNK codons. DSM 25 libraries consisted of NNK positions at residues 71-75 and 155-159, ULBP2 R80W libraries with NNK codons at positions 154-159, and ULBP3 R162G libraries with NNK codons at positions 155-159. Libraries were cloned as fusions to the pIII minor coat protein of M13 phage; and phage particles displaying the mutagenized α1-α2 domain variants were produced in SS320 *E. coli* cells according to standard methodologies (Andris-Widhopf, J., Steinberger, P., Fuller, R., Rader, C., and Barbas, C. F., 3rd. (2011). Generation of human Fab antibody libraries: PCR amplification and assembly of light- and heavy-chain coding sequences, *Cold Spring Harbor protocols* 2011). The α1-α2 phage display libraries were sorted for high binding affinity to the non-natural Y152A NKG2D receptor by selectively capturing phage clones bound to biotinylated Y152A NKG2D-Fc protein in the presence of non-biotinylated natural NKG2D-Fc competitor protein. Selective clones were enriched by cycling through multiple rounds of competitive selection with increasing concentrations of non-biotinylated natural NKG2D-Fc.

After four rounds of selection, phage clones were sequenced to identify specific mutations within the NNK mutagenic regions. Tables 8, 9, and 10 show the selected amino acid residues that were found to be prevalent for each α1-α2 domain resulting from the Y152A NKG2D selective screening.

TABLE 8

Selected mutations within DSM25 that resulted in Y152A-specific phage clones.

| K71 | D72 | L73 | R74 | M75 | T155 | H156 | Y157 | H158 | A159 |
|---|---|---|---|---|---|---|---|---|---|
| T | T | L | L | R | I | G | G | G | L |
| L | F | | | L | R | S | S | S | I |
| D | R | | | | H | R | L | L | R |
| | | | | | | W | | | |

TABLE 9

Selected mutations within ULBP2 R80W that resulted in Y152A-specific phage clones.

| M154 | S155 | F156 | H157 | Y158 | F159 |
|------|------|------|------|------|------|
| T    | M    | L    | E    | L    | W    |
|      | K    | M    | T    | V    | I    |
|      | W    |      | S    | I    |      |
|      | L    |      | Q    | T    |      |
|      | T    |      | Y    |      |      |
|      |      |      | R    |      |      |

TABLE 10

Selected mutations within ULBP3 R162G that resulted in Y152A-specific phage clones.

| F155 | F156 | K157 | M158 | V159 |
|------|------|------|------|------|
| D    | L    | I    | R    | R    |
| W    | M    | Y    | L    | I    |
| R    |      | V    | T    | W    |
| Y    |      | L    |      | K    |
| L    |      |      |      |      |

Figure 23:
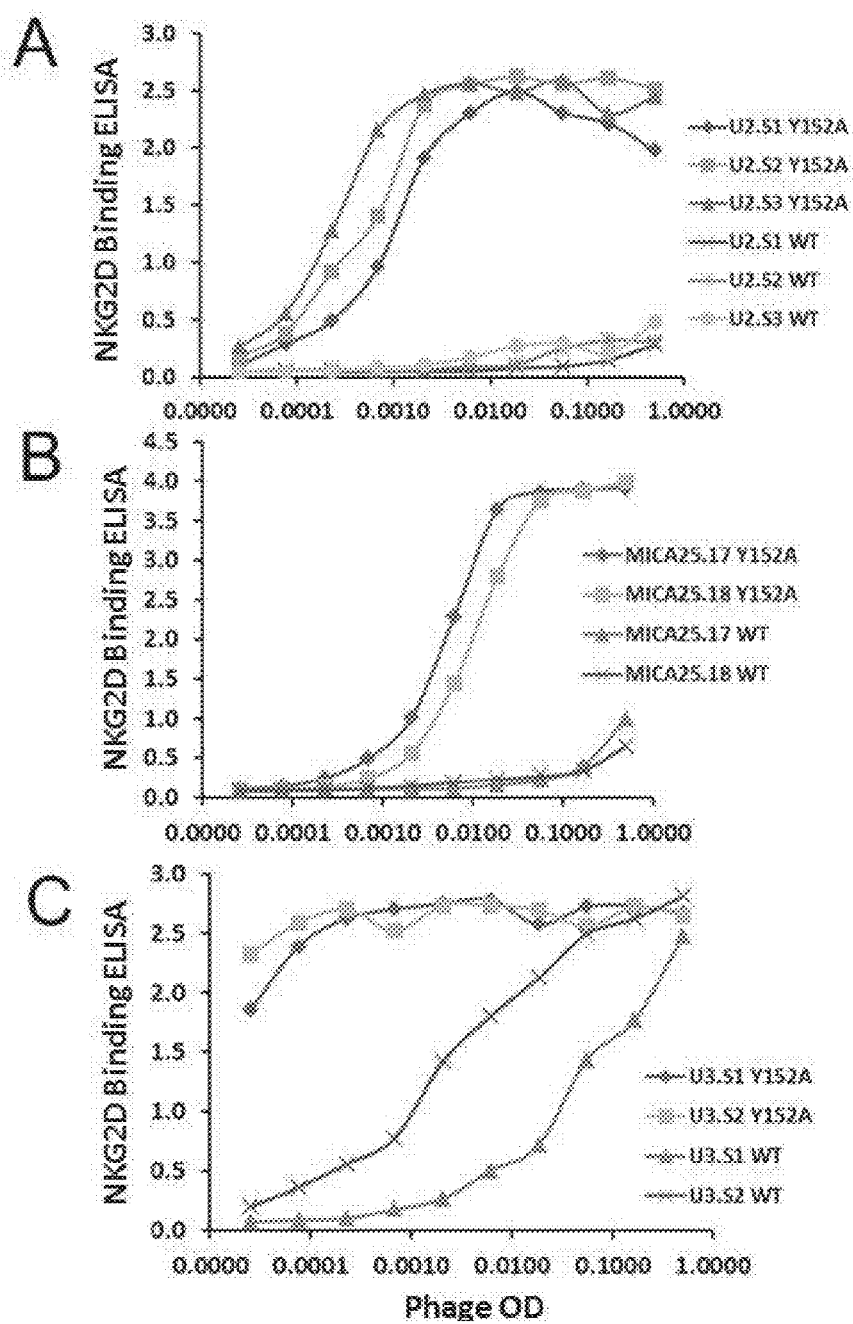
FIG. 23. Phage ELISA results of non-natural α1-α2 domains selected for binding to Y152A NKG2D-Fc. (A) Orthogonal ULBP2 clones, (B) Orthogonal MICA clones, and (C) Orthogonal ULBP3 clones.

To confirm the phage clones displayed proper selective binding, phages were produced for the individual clones: MICA25.17, MICA25.18, ULBP2.S1, ULBP2.S2, ULBP2.S3, ULBP3.S1 and ULBP3.S2 (SEQ ID NOs: 90, 91, 92, 93, 94, 95, and 96 respectively) and titrated against Y152A or natural NKG2D in binding ELISAs. FIG. 23, Panels A-C, demonstrated that all 7 phage clones displayed greater than 10-fold selective binding to non-natural Y152A NKG2D over natural or wild-type NKG2D.

Figure 24:
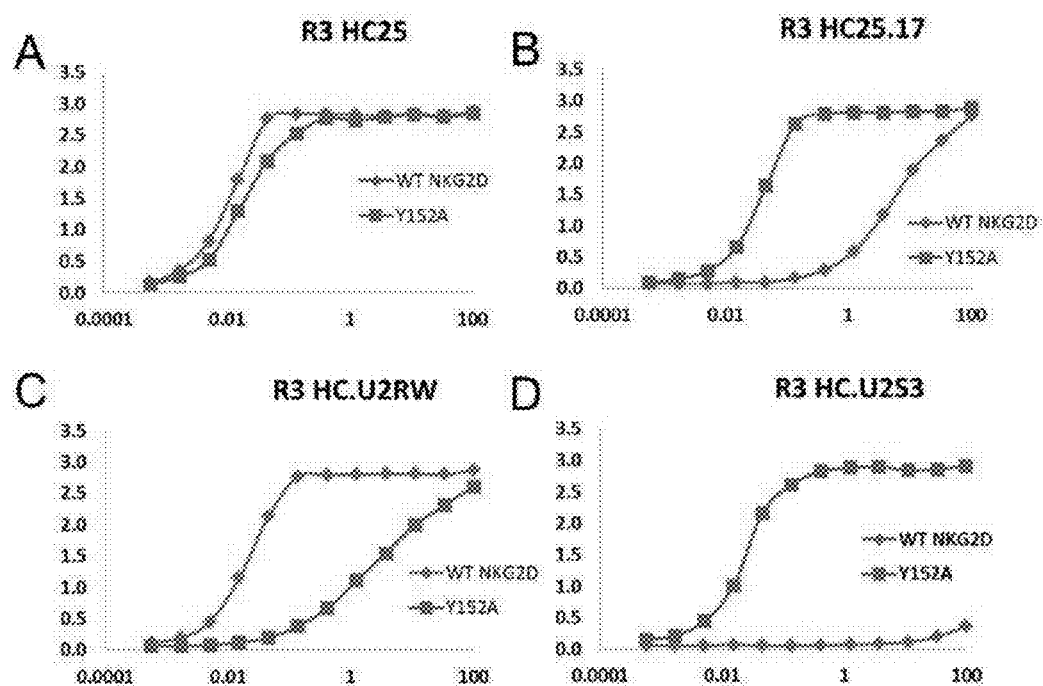
FIG. 24. ELISA results for R3 antibody fusions to non-natural α1-α2 domains selected for binding to Y152A NKG2D-Fc. (A) R3 HC25 antibody fusion is not selective for Y152A NKG2D. (B) R3 HC25.17 (SEQ ID NO.: 97) antibody fusion is selective for Y152A NKG2D over natural NKG2D-Fc. (C) R3 HC.U2RW antibody fusion is not selective for Y152A NKG2D over natural NKG2D-Fc. (D) R3 HC.U2S3 (SEQ ID NO.: 98) antibody fusion is selective for Y152A NKG2D over natural NKG2D-Fc.

To confirm the Y152A-selective α1-α2 domain variants retain specific binding properties within the context of antibody fusions, we cloned MICA25.17 and ULBP2.S3 as C-terminal fusions to the heavy chain of an FGFR3 specific antibody previously described (Qing et al, 2009. op cit; SEQ ID NO.s: 97 and 98, respectively). The resulting fusions were cloned into the mammalian expression vector pD2509 and co-expressed with the light chain of the parent antibody as paired full IgG antibodies (R3 HC25.17 and R3 HC.U2S3). Transient expressions were carried out in HEK293 cells using the Expi293 expression system according to the manufacturer's protocol (Life Technologies), and purified using standard protein-A affinity chromatography. ELISAs measuring the binding of R3 HC25.17 and R3 HC.U2S3 α1-α2 antibody heavy chain fusions to non-natural Y152A NKG2D and to natural NKG2D demonstrated their significantly greater binding affinity toward Y152A NKG2D relative to the natural NKG2D (FIG. 24, Panels B and D). In contrast, the antibody fusions to DSM25 and ULBP2 R80W exhibited preferred binding to natural NKG2D-Fc (FIG. 24, panels A and C). Collectively, these data demonstrated the invention of non-natural orthogonal α1-α2 domains that possessed high affinity binding to non-natural NKG2D receptors and significantly reduced binding affinity to the natural NKG2D receptor. Furthermore, fusions of orthogonal α1-α2 domains to antibody polypeptides retained their selective binding properties and can be used to redirect non-natural NKG2D receptors toward new antigens, for example in the context of CAR-T cells Example 8 (The Targeting and Killing Activity of CAR-T Cells with the Non-natural NKG2D Ectodomain are Controlled Using Orthogonal α1-α2 Domains Fused to Targeting Antibodies)

Figure 25:
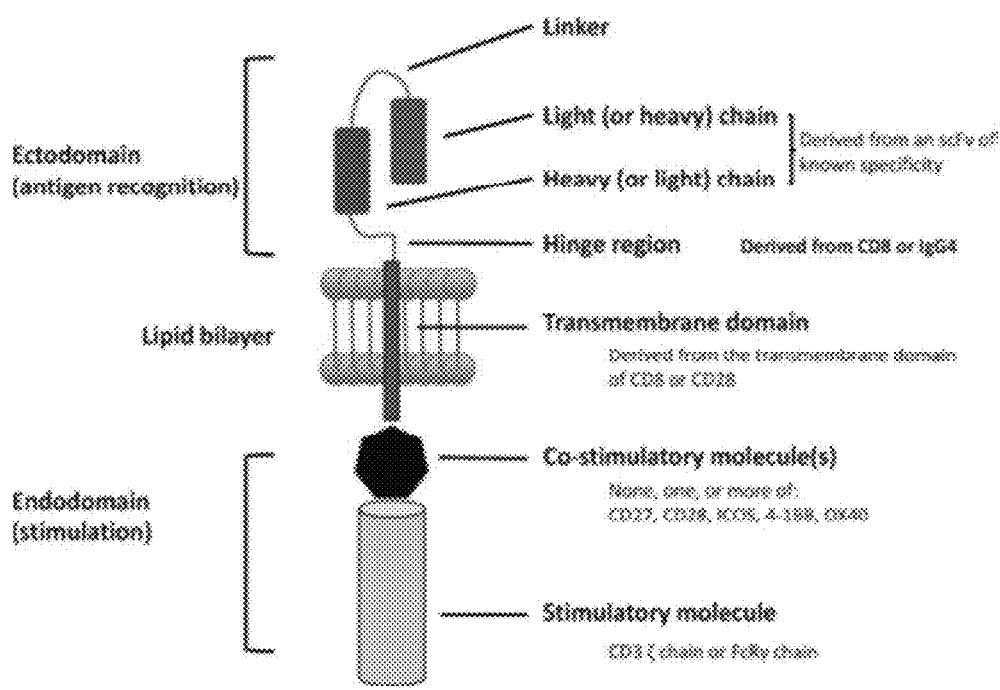
FIG. 25. Anatomy of a typical CAR (Gill & June, 2015, op cit).
Figure 26:
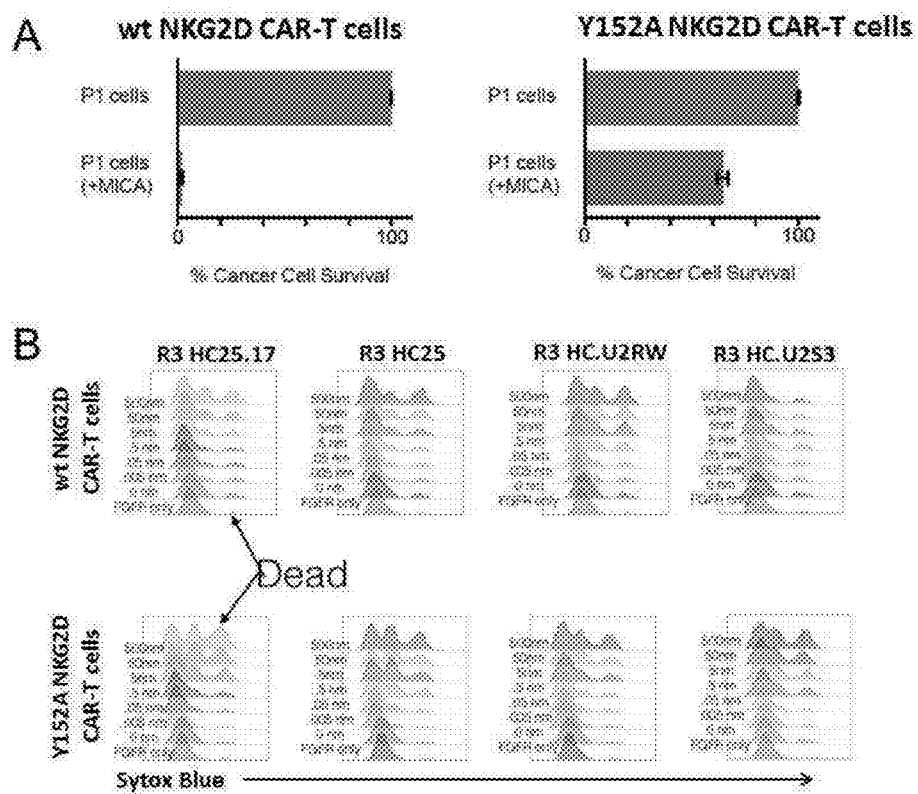
FIG. 26. In-vitro CAR-T assays for target cell killing. (A) Natural NKG2D CAR-T cells kill P1 target cells expressing natural MICA while Y152A NKG2D CAR-T cells are disabled and have reduced killing activity against MICA expressing targets. (B) The selective orthogonal antibody fusions, R3 HC25.17 (SEQ ID NO.: 97) and R3 HC.U2S3 (SEQ ID NO.: 98) selectively control the killing activity of Y152A NKG2D CAR-T cells against FGFR3 expressing cells.

To demonstrate selective control of CAR-T cells constructed with a chimeric receptor deploying the non-natural NKG2D ectodomain, we constructed CARs with either the natural NKG2D or the non-natural Y152A NKG2D ectodomains based on previous work using 4-1BB/CD3zeta CAR constructs (Campana U.S. Pat. No. 8,399,645) fusing the respective NKG2D ectodomains to the CD8 hinge region (FIG. 25) of CARs. These constructs were cloned into a lentiviral vector and expressed in primary human CD8-positive T-cells using lentiviral transduction. The resulting natural NKG2D CAR-T cells exhibited specific cell killing activity in vitro, consistent with recognition of the natural MICA ligand expressed on target cells. Specifically, FIG. 26, Panel A, showed that although natural NKG2D CAR-T cells killed P1 cells expressing natural MICA ligands, the non-natural Y152A NKG2D CAR-T cells were significantly disabled and exhibited much reduced killing of MICA expressing P1 cells. Furthermore, FIG. 26, Panel B, showed that the orthogonal α1-α2 antibody heavy chain fusions, R3 HC25.17 and R3 HC.U2S3, selectively activated the non-natural Y152A CAR-T cells to kill FGFR3 expressing P1 target cells, but were not capable of redirecting the killing activity of natural NKG2D CAR-T cells. This was in contrast to the R3 HC25 and R3 HC.U2R80W α1-α2 antibody heavy chain fusions which were not selective for non-natural Y152A NKG2D and activated both natural and non-natural CAR-T cells to kill P1 target cells. These data showed non-natural orthogonal α1-α2 domains engineered to bind selectively to non-natural Y152A NKG2D specifically activated non-natural Y152A NKG2D CAR-T cells while avoiding natural NKG2D receptors.

What is claimed is:

1. A non-natural NKG2D receptor, wherein said non-natural NKG2D receptor is a chimeric NKG2D receptor that comprises an ectodomain comprising the amino acid sequence of SEQ ID NO: 75 but in which the tyrosine at position 73 of SEQ ID NO: 75 has been replaced with alanine.

2. A cell that is a lymphocyte or NK cell comprising the non-natural NKG2D receptor of claim 1.

3. The cell of claim 2 that is a human T lymphocyte.

4. The cell of claim 2 that is a human NK cell.

5. A chimeric antigen receptor comprising a non-natural NKG2D receptor ectodomain comprising the amino acid sequence of SEQ ID NO: 75 but in which the tyrosine at position 73 of SEQ ID NO: 75 has been replaced with alanine.

6. A cell that is a lymphocyte or NK cell comprising the chimeric antigen receptor of claim 5.

7. The cell of claim 6 that is a human T lymphocyte.

8. The cell of claim 6 that is a human NK cell.

9. A non-natural, modified α1-α2 domain of a NKG2D ligand that (a) binds a non-natural NKG2D receptor ectodomain comprising the amino acid sequence of SEQ ID NO: 75 but in which the tyrosine at position 73 of SEQ ID NO: 75 has been replaced with alanine, and that (b) comprises the amino sequence of SEQ ID NO: 57 but in which one or more of the amino acids at positions 71, 72, 73, 74, 75, 155, 156, 157, 158, and 159 have been replaced, the amino acid sequence of SEQ ID NO: 87 but in which one or more of the amino acids at positions 154, 155, 156, 157, 158, and 159 have been replaced, or the amino acid sequence of SEQ ID NO: 89 but in which one or more of the amino acids at positions 155, 156, 157, 158, and 159 have been replaced.

10. The non-natural, modified α1-α2 domain of claim 9, further comprising an attached heterologous molecule or atom.

11. The non-natural, modified α1-α2 domain of claim 10, wherein the heterologous molecule is a peptide or a polypeptide.

12. The non-natural, modified α1-α2 domain of claim 11, wherein the polypeptide is an antibody or antigen-binding fragment thereof.

13. A non-natural, modified α1-α2 domain that comprises SEQ ID NO: 90, 91, 92, 93, 94, 95, or 96.

14. The non-natural, modified α1-α2 domain of claim 13 that comprises SEQ ID NO: 90.

15. The non-natural, modified α1-α2 domain of claim 13 that comprises SEQ ID NO: 91.

16. The non-natural, modified α1-α2 domain of claim 13 that comprises SEQ ID NO: 92.

17. The non-natural, modified α1-α2 domain of claim 13 that comprises SEQ ID NO: 93.

18. The non-natural, modified α1-α2 domain of claim 13 that comprises SEQ ID NO: 94.

19. The non-natural, modified α1-α2 domain of claim 13 that comprises SEQ ID NO: 95.

20. The non-natural, modified α1-α2 domain of claim 13 that comprises SEQ ID NO: 96.

21. A fusion protein comprising a non-natural, modified α1-α2 domain of claim 9 and an antibody or antigen-binding fragment of an antibody.

22. A fusion protein comprising a non-natural, modified α1-α2 domain of claim 13 and an antibody or antigen-binding fragment of an antibody.

23. A method of killing a cell comprising contacting the cell with a fusion protein comprising a non-natural, modified α1-α2 domain that comprises SEQ ID NO: 90, 91, 92, 93, 94, 95, or 96 fused to an antibody or antigen-binding antibody fragment, wherein the antibody or antigen-binding antibody fragment binds a target antigen on the cell, and also contacting the cell with a lymphocyte or NK cell comprising a chimeric antigen receptor comprising a non-natural NKG2D receptor ectodomain comprising the amino acid sequence of SEQ ID NO: 75 but in which the tyrosine at position 73 of SEQ ID NO: 75 has been replaced with alanine, to thereby kill the cell.

* * * * *